(12) United States Patent
Wallace et al.

(10) Patent No.: US 12,082,992 B2
(45) Date of Patent: Sep. 10, 2024

(54) INVERTING SLEEVE APPARATUSES AND METHOD FOR DRYING AND CLEANING THE EAR OR NOSE

(71) Applicant: 880 Medical LLC, Pleasanton, CA (US)

(72) Inventors: Michael P. Wallace, Pleasanton, CA (US); Michael A. Dotsey, Chester Springs, PA (US); Andrew Miller, Pleasanton, CA (US)

(73) Assignee: 880 Medical LLC, Pleasanton, CA (US)

( * ) Notice: Subject to any disclaimer, the term of this patent is extended or adjusted under 35 U.S.C. 154(b) by 0 days.

(21) Appl. No.: 18/480,486

(22) Filed: Oct. 3, 2023

(65) Prior Publication Data

US 2024/0108512 A1    Apr. 4, 2024

Related U.S. Application Data

(60) Provisional application No. 63/510,355, filed on Jun. 26, 2023, provisional application No. 63/412,649, filed on Oct. 3, 2022.

(51) Int. Cl.
*A61F 11/00* (2022.01)
*A61F 13/15* (2006.01)
*A61F 13/505* (2006.01)

(52) U.S. Cl.
CPC ...... *A61F 11/006* (2013.01); *A61F 13/15268* (2013.01); *A61F 13/15707* (2013.01); *A61F 13/505* (2013.01); *A61F 2013/15008* (2013.01)

(58) Field of Classification Search
CPC .............. A61F 11/006; A61F 13/15268; A61F 13/15707; A61F 13/505; A61F 2013/15008
See application file for complete search history.

(56) References Cited

U.S. PATENT DOCUMENTS

| | | |
|---|---|---|
| 6,994,387 B1 | 2/2006 | Ranger et al. |
| 2005/0049576 A1 | 3/2005 | Snell et al. |
| 2013/0226196 A1 | 8/2013 | Smith |
| 2017/0348014 A1 | 12/2017 | Wallace et al. |
| 2019/0133627 A1* | 5/2019 | Wallace ......... A61B 17/320725 |
| 2020/0129194 A1 | 4/2020 | Wallace et al. |
| 2020/0245983 A1 | 8/2020 | Chin et al. |
| 2020/0397478 A1 | 12/2020 | Bachch et al. |
| 2021/0016543 A1 | 1/2021 | Smith |
| 2021/0186543 A1 | 6/2021 | Wallace et al. |

* cited by examiner

*Primary Examiner* — Anh T Dang
(74) *Attorney, Agent, or Firm* — Shay Glenn LLP

(57) ABSTRACT

Methods and apparatuses for cleaning and/or drying a subject's ears and/or nose may include an inverting tubular swab region. These apparatuses may remove debris, such as ear wax & skin debris from the ear canal. These apparatuses are safer than traditional cotton swab. Also described herein are apparatuses configured for use in the nose, which may remove mucus (e.g., snot) from the nasal and sinus regions. These apparatuses may be configured for use with infants and toddlers as an alternative to air aspiration bulb/tool. Also described herein are methods of using any of these apparatuses as well as methods of making and packaging them.

22 Claims, 39 Drawing Sheets

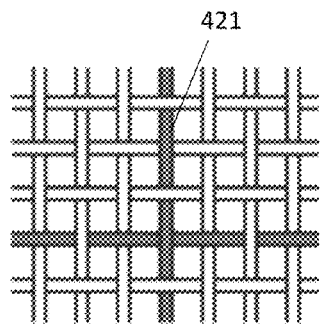 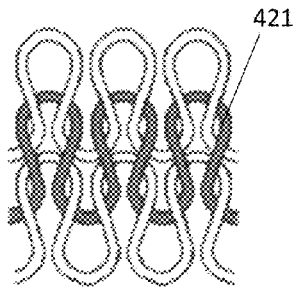 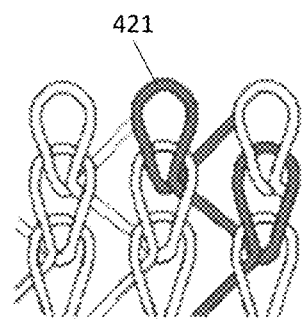
FIG. 4A  FIG. 4B  FIG. 4C
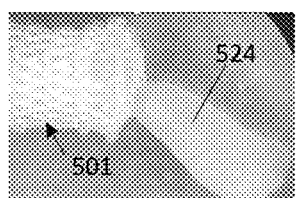 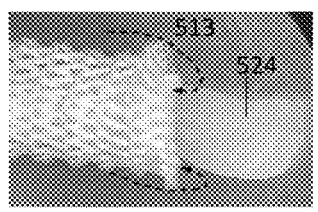 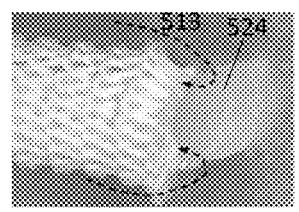 
FIG. 5A  FIG. 5B  FIG. 5C  FIG. 5D
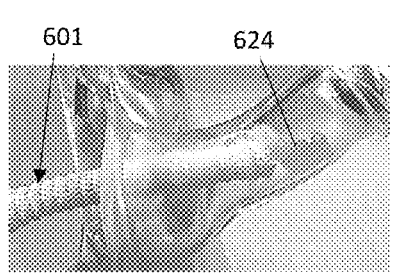 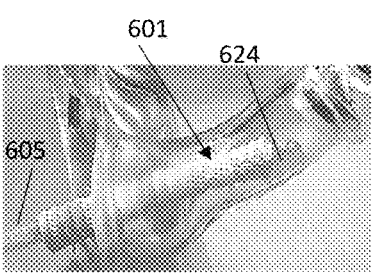 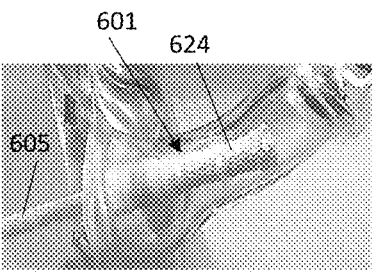
FIG. 6A  FIG. 6B  FIG. 6C

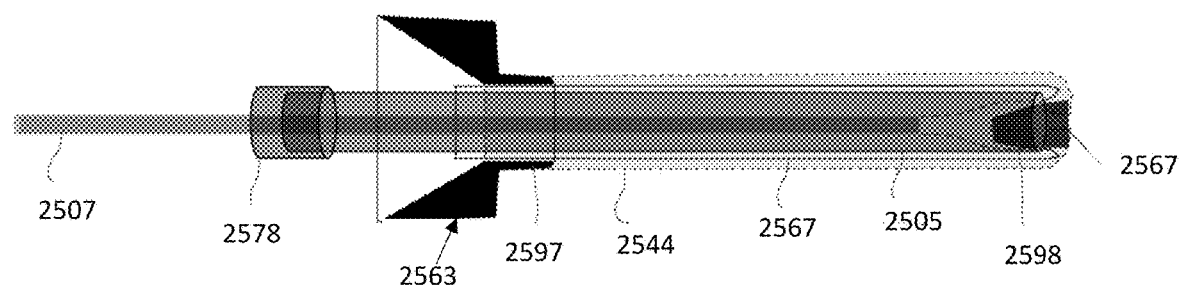
FIG. 25
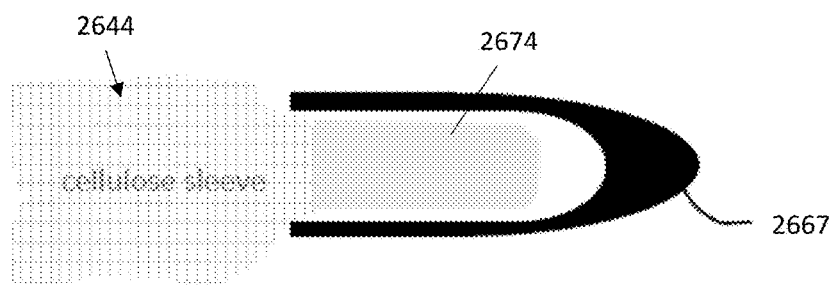
FIG. 26
  
FIG. 27A  FIG. 27B  FIG. 27C

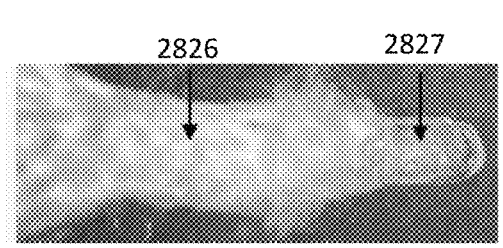
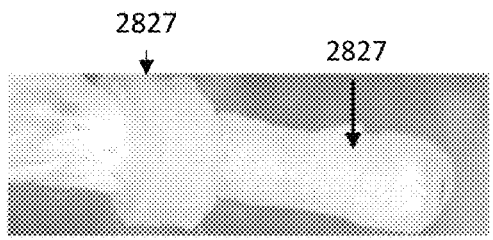
FIG. 28A  FIG. 28B
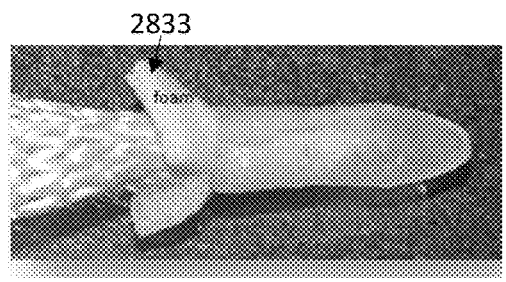
FIG. 28C
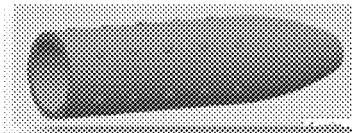 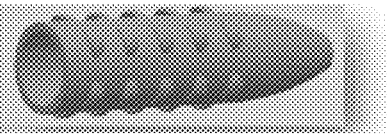
FIG. 29A  FIG. 29B
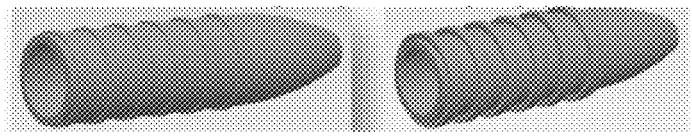
FIG. 29C  FIG. 29D
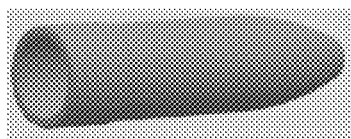 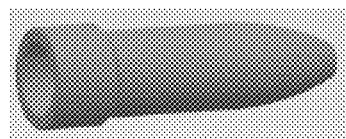
FIG. 29E  FIG. 29F
FIG. 29G

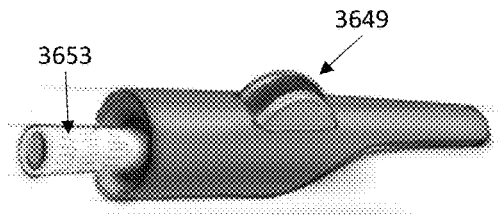
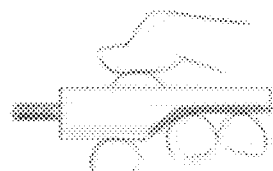
FIG. 36A  FIG. 36B
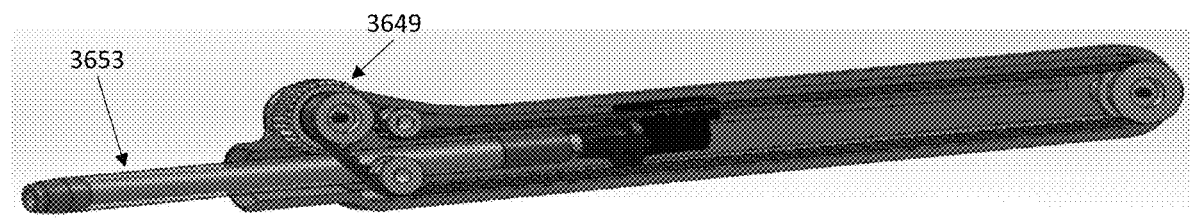
FIG. 36C
FIG. 36D

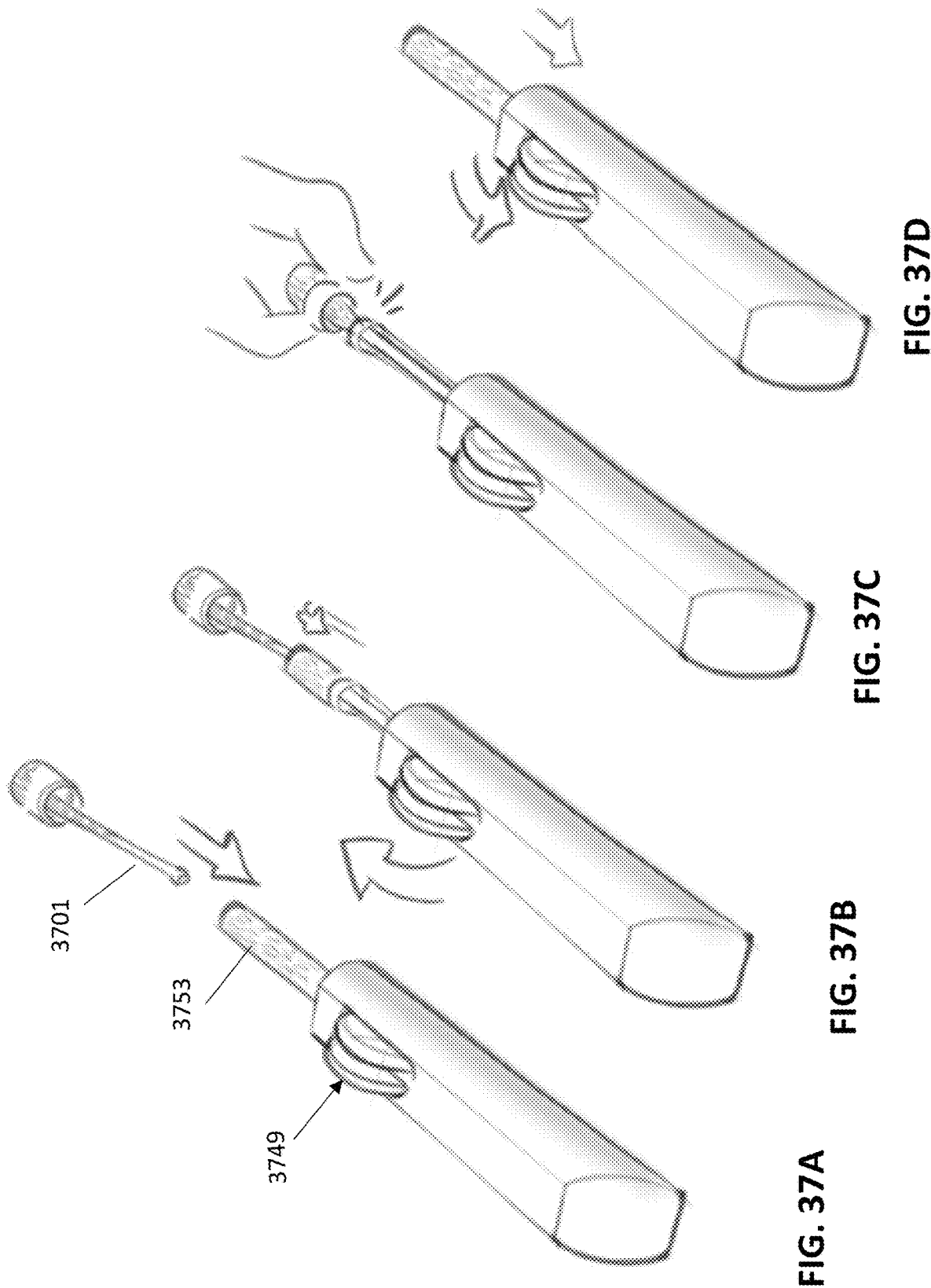

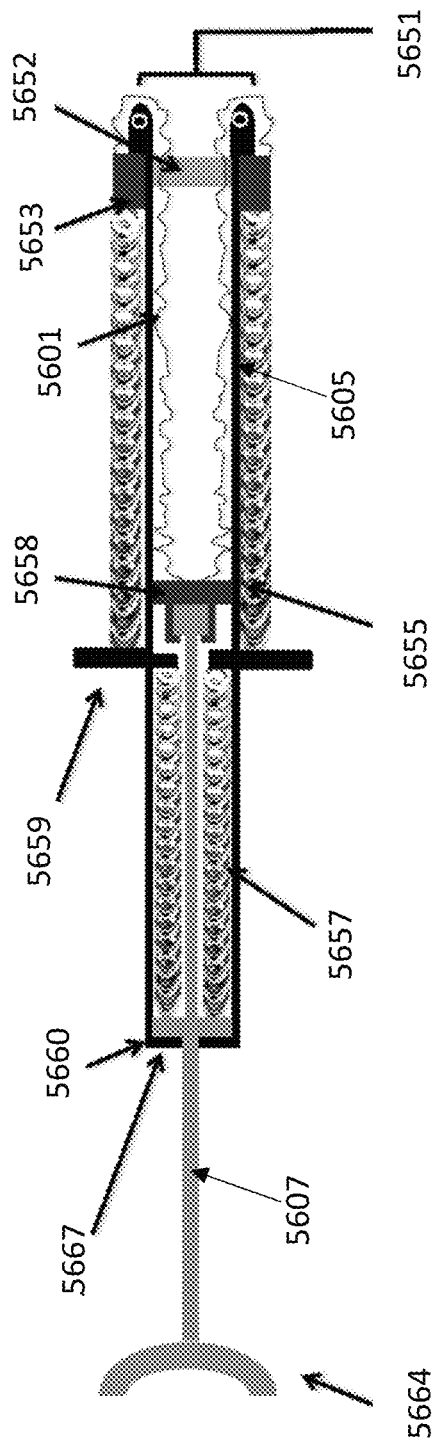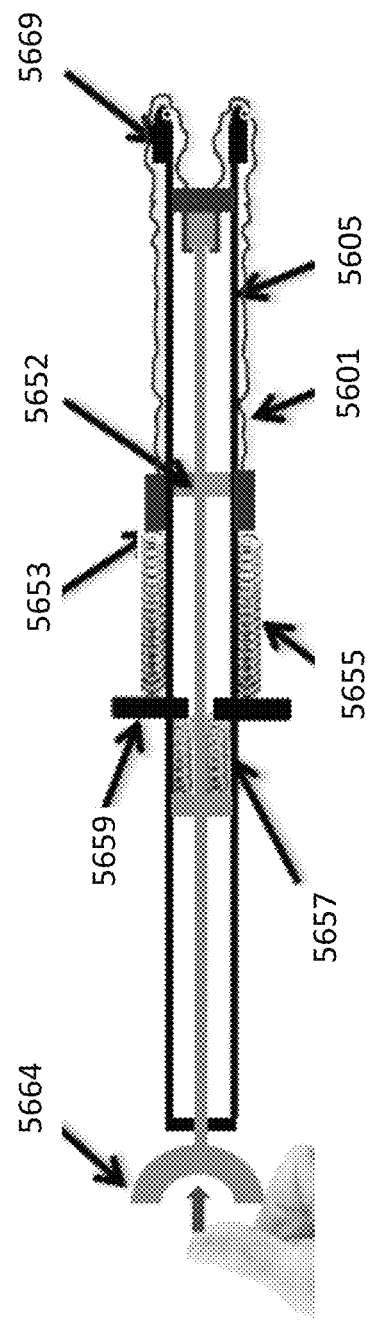
FIG. 56A
FIG. 56B

INVERTING SLEEVE APPARATUSES AND METHOD FOR DRYING AND CLEANING THE EAR OR NOSE

CLAIM OF PRIORITY

This patent application claims priority to U.S. Provisional Patent Application No. 63/412,649, titled "INVERTING SLEEVE EAR AND NOSE CLEANING TECHNOLOGY" and filed on Oct. 3, 2022, and U.S. Provisional Patent Application No. 63/510,355, titled "APPARATUS AND METHOD FOR DRYING AND CLEANING THE EAR OR NOSE," filed on Jun. 26, 2023, each of which is herein incorporated by reference in its entirety.

BACKGROUND

Cotton swabs or buds are wads of cotton wrapped around a short rod made of wood, rolled paper, or plastic, and are most commonly used for cleaning narrow regions of the human body such as the ears, although this is not recommended by physicians. These devices have been commercially available for over a hundred years, and were marketed for removal of ear wax (cerumen) and drying of the ear. However, in recent years swabs have been increasingly criticized as unsafe, as they may result in cerumen impaction, a buildup or blockage of cerumen in the ear canal, which can cause pain, hearing problems, ringing in the ear, or dizziness, and may require medical treatment to resolve. The use of cotton swabs in the ear canal is also one of the most common causes of perforated eardrum, requiring surgery to correct. Indeed, swabs are believed to be the leading cause of otitis externa in children.

Despite these risks, swabs remain highly popular with consumers, hoping to use them for removing wax and/or water to clean the ears. It would therefore be desirable to provide a device that can perform or improve upon the cleaning function of a cotton swab, while minimizing the risk associated with introducing such devices into the body.

Described herein are apparatuses and method for safely and effectively cleaning and/or drying an external body region, such as the ear or nose, that may address these needs. The apparatuses described herein may be used safely on a regular, e.g., daily, basis.

SUMMARY OF THE DISCLOSURE

In general, described herein are single-use and reusable inverting sleeve swab apparatuses (e.g., devices, systems, etc.) and methods of making and using them. In general, these apparatuses may include an invertible tube, formed of an absorbent material that may be drawn over itself to invert and remover material from the body (e.g., from the ears or nose). These apparatuses include single-use (e.g., disposable) inverting sleeve swabs that include a handle and low-cost cartridges/sleeve. These apparatuses also include a reusable inverting sleeve swab (e.g., multi-use cartridges/sleeves) that may be part of or configured for use with a handle or applicator. In general, these apparatuses may be used to dry the outside of the ear (concha, fossa trianglularis, scapha) and/or the inside of the ear canal, to aid in removal of ear wax and debris with risk of ear drum damage, and to safely exfoliate the inside of the ear. These apparatuses may be configured for one-handed and two-handed variations, and may generally work for a variety of different hand sizes. For example, these apparatuses may be configured to provide adequate affordance (e.g., grip) for one handed use and may provide the user with a high degree of depth control and safety. Further, these apparatuses are configured to be easy to use, including easy to install/remove an inverting sleeve and/or easy to reset, clean and re-use.

In general, the use of an inverting material on the swabs described herein provide advantage not possible with conventional (non-inverting) swabs or similar devices. For example, the use of an inverting swab material is much better at capturing material within the body orifice (e.g., ear, nose, etc.). The inverting sleeves described herein may, in particular, capture and entrap material for safe removal without compacting the material against a wall of the body orifice. The inverting sleeves described herein are also significantly softer, while providing sufficient structure (particularly at the distal end) and support insertion and removal. In addition, the material used for the inverting sleeve may be absorbent, allowing capture of liquid (e.g., water) as well as solid or gelatinous material (mucus, sebum, etc.).

For example, described herein are inverting swab apparatuses that may include: an elongate tubular shaft; an inverting swab sleeve comprising an inverted tube of material; a driver for driving inversion of the inverting swab sleeve over the elongate tubular shaft, wherein the driver comprises a reciprocating shaft; and a control for operating the driver.

In any of these apparatuses the control may be part of the reciprocating shaft.

The material may be absorbent. For example the inverting swab sleeve may be an absorbent cellulose fiber and/or cotton fiber. In some example the material is nonabsorbent, and may be abrasive. For example, the inverting swab sleeve may be a nonabsorbent material comprising a polypropylene material, a nylon material, and/or a polyethylene terephthalate (PET) material.

For example, an inverting swab apparatus may comprise: an elongate tubular shaft; an inverting swab sleeve comprising a knitted, woven or braided inverted tube of absorbent material; a driver for driving inversion of the inverting swab sleeve over the elongate tubular shaft, wherein the driver comprises a reciprocating shaft slidably positioned within the elongate tubular shaft; and a control for moving the driver relative to the elongate tubular shaft.

In some examples the inverting swab apparatus comprises: an elongate tubular shaft; an inverting swab sleeve comprising an inverted tube of absorbent material; a driver for driving inversion of the inverting swab sleeve over the elongate tubular shaft, wherein the driver comprises a reciprocating shaft slidably positioned within the elongate tubular shaft; and a control for moving the driver relative to the elongate tubular shaft.

The driver may be configured to move relative to the elongate tubular shaft to pull and invert the inverting swab sleeve. Any appropriate driver may be used. For example, the driver may be a tube, rod, fiber, filament, etc.

The control may comprise a grip, such as a finger grip. The control may be a button, slider, puller, etc. For example, the control may comprise one or more of: a slider, a knob, a roller, a dial, or a button.

The reciprocating shaft of the driver may be slidably positioned within the elongate tubular shaft. For example the reciprocating shaft of the driver may be configured to reciprocate within a length of the elongate tubular shaft. The reciprocating shaft of the driver may be coupled to the inverting swab sleeve and may be slidably coupled within the elongate tubular shaft. The inverting swab sleeve may be configured to invert over the elongate tubular shaft.

In some examples the driver does not directly (or permanently) connect to the inverting swab sleeve. For example the driver, including the reciprocating shaft, indirectly couples with the inverting swab sleeve to drive movement of the inverting swab sleeve to invert. For example, the drive may include an inverting conveyor tube configured to engage the inverting swab sleeve; the inverting conveyer tube may itself roll and invert over elongate tubular shaft as the reciprocating shaft is moved. The inverting conveyor tube may be coupled to a first end region of the reciprocating shaft at both a first end region of the inverting conveyor tube and at a second end region of the inverting conveyer tube. The second end of the inverting conveyer tube may be coupled to the first end region by one or more tethers. In some examples, the inverting swab sleeve may comprise an engagement cap at the first end that is configured to engage with the inverting conveyer tube. The inverting swab sleeve may be curved at a distal end.

Any of these apparatuses may include a cuff at the first end of the inverting swab sleeve. The cuff may be configured to provide a surface or region to allow resetting of the inverting swab sleeve. In some examples the reciprocating shaft may be pulled (e.g., proximally) to cause inverting of the inverting swab sleeve at the distal end of the device. The inverting swab sleeve may be returned to an initial (start) position by pulling proximally on the cuff. Thus, the cuff may include an engagement site to allow a user to pull (or ins some cases push) the inverting swab sleeve so that it reverts back over itself at the distal end of the device. In some cases the cuff may include attachments to one or more tethers that may couple to a control (in some cases the same control that is coupled to the driver, or alternatively a separate control) to pull and/or push the cuff.

In general, the inverting swab sleeve may be formed of any particular material. For example, the inverting swab sleeve may be formed of a fabric material that is knitted, woven, braided, or the like. In some examples, the inverting swab sleeve may be formed of a plurality of lengths of filament lengths. These lengths of filament may be part of one or more filaments that are knitted, braided, woven, etc. The lengths of filament may be formed of a natural material (e.g., plant fiber, such as cotton, etc.) or synthetic (e.g., polymeric material, metallic material, etc.). The lengths of filament may be formed of a single fiber or strand or multiple strands or fibers. The inverting swab sleeve may be formed of an absorbent material, such as a material configured to absorb water and/or oils. For example, the inverting swab sleeve may be formed of lengths of filament comprising an absorbent cellulose fiber.

Any of these apparatuses may include a bulb region on the elongate tubular shaft. The bulb region may form an enlarged outer width (outer diameter) at a distal end region of the device, and may be configured to limit the insertion depth of the apparatus. For example, the bulb region may be configured to limit insertion into a subject's ear to a relatively shallow depth. In some examples the bulb is positioned at a distal end region of the elongate tubular shaft. The bulb may be positioned near the distal end or proximate to the distal end by an offset distance (e.g., between about 1 mm and about 30 mm, between about 1 mm and about 25 mm, between about 1 mm and about 20 mm, between about 1 mm and 15 mm, between about 1 mm and 10 mm, etc.).

In general, these apparatuses may be configured for insertion into a small body orifice, such as the ear, nose, etc. Thus, the apparatus may be dimensioned for insertion into most people's ears, nose, etc. For example, the inverting swab sleeve may have a diameter of between 3 mm and 15 mm (e.g., between 3 mm and 14 mm, between 3 mm and 13 mm, between 3 mm and 12 mm, between 3 mm and 11 mm, between 3 mm and 10 mm, between 3 mm and 9 mm, between 3 mm and 8 mm, etc.) in the deployed configuration. The inverting swab sleeve may be configured so that the diameter is variable, and/or is configured to expand/contract. In some cases the deployed outer diameter of the inverting swab sleeve is configured to change as it is inverted over the elongate tubular shaft.

The inverting swab sleeve may be any appropriate length, for example, between about 1 and 15 cm long (e.g., between about 1.5 and 14 cm long, etc.). The length of the inverting swab sleeve may refer to the swab sleeve in the fully deployed (e.g., fully inverted) configuration.

In some examples the inverting swab sleeve comprises a pull stick coupled to the first end. In some examples the inverting swab sleeve is configured to be removably coupled to the driver and the elongate tubular shaft.

The inverting swab apparatuses described herein may be configured for use with two hands or with one hand. In one example a user may grasp the inverting swab apparatus by the outer tube shaft (elongate tubular shaft), e.g., with the fingers, and may pull on the control, distally, to invert the swab sleeve so that it rolls over itself and into (or in some examples out of) the elongate tubular shaft.

Also described herein are apparatuses that are configured to be operated with one hand. In some cases, these apparatuses may be configured so that the device includes a control that can be operated with the same hand as the hand holding the device. For example, the apparatus may include a handle portion that includes a handle body onto which a control (e.g., slider, dial, roller, etc.) is connected. The handle may be held, e.g., in the palm of the user's hand, while the control may be activated by one or more fingers and/or thumb.

Although many of the devices described herein are primarily mechanical and may actuate the movement of the inverting swap purely mechanically by mechanical means, e.g., manually, in some examples the apparatus may be actuated by a powered means, such as a motor or other electrically powered driver.

For example, described herein are inverting swab apparatuses (e.g., systems) that may include a re-usable swab actuator and one or more (e.g., a plurality of) disposable inverting swab sleeves that may be removably coupled to the swab actuator. In some examples the inverting swab system may include: a swab actuator comprising: an elongate tubular shaft; a driver, the driver comprising: a reciprocating shaft; an inverting conveyor tube configured to roll and invert over the elongate tubular shaft as the reciprocating shaft is moved; one or more tethers coupling a first end of the inverting conveyor tube to a first end region of the reciprocating shaft, wherein a second end of the inverting conveyor tube is coupled to the first end region; and a control for operating the driver to reciprocate the reciprocating shaft relative to the elongate tubular shaft to roll and invert the inverting conveyer tube. In some examples the inverting conveyer tube may be configured as the inverting swab sleeve, and may be inserted into the body region (e.g., ear, nose, etc.) directly. However, this may limit the number of uses of the apparatus. Alternatively, in some examples the apparatus may also include one, or a plurality of, inverting swab sleeves that are configured to be used with the swab actuator; multiple different inverting swab sleeves may be used with the swab actuator so that the swab actuator is durable/reusable, while the inverting swab sleeves may be limited-use (e.g., single use) and/or disposable. For example, an inverting swab sleeve may be an inverted tube that is configured to be removably engaged with the inverting conveyer tube of the swab actuator.

For example, an inverting swab system may include: a swab actuator comprising: an elongate tubular shaft; a driver, the driver comprising: a reciprocating shaft slidably positioned within the elongate tubular shaft; an inverting conveyor tube configured to roll and invert over the elongate tubular shaft as the reciprocating shaft is moved; one or more tethers coupling a first end of the inverting conveyor tube to a first end region of the reciprocating shaft, wherein a second end of the inverting conveyor tube is coupled to the first end region; and a control for operating the driver to reciprocate the reciprocating shaft relative to the elongate tubular shaft to roll and invert the inverting conveyer tube over the elongate tubular shaft; and an inverting swab sleeve comprising an inverted tube that is configured to removably couple to the swab actuator.

In some examples the inverting swab system includes: a swab actuator comprising: an elongate tubular shaft; a driver, the driver comprising: a reciprocating shaft; an inverting conveyor tube configured to roll and invert over the elongate tubular shaft as the reciprocating shaft is moved; one or more tethers coupling a first end of the inverting conveyor tube to a first end region of the reciprocating shaft, wherein a second end of the inverting conveyor tube is coupled to the first end region; and a control for operating the driver to reciprocate the reciprocating shaft relative to the elongate tubular shaft to roll and invert the inverting conveyer tube; and an inverting swab sleeve comprising an inverted tube and an engagement cap coupled to first end of the inverted tube, wherein the inverting conveyer tube is configured to removably engage with the engagement cap of the inverting swab sleeve.

The swab actuator may include a handle configured to be held by a user's hand. The handle may include a housing enclosing some or all of the swab actuator components (e.g., reciprocating shaft, tethers, control components, etc.). The reciprocating shaft may be slidably positioned within the elongate tubular shaft. In some examples the reciprocating shaft may be coupled to the inverting conveyor tube on one end (e.g., a distal end region) and may also be coupled to the control.

In general, the inverting swab sleeve may be configured to be removably attached to the swab actuator so that it may be inserted into the body orifice (e.g., ear, nose, etc.) and actuated to invert over itself to absorb and/or remove material from the body orifice. For example, the inverting swab sleeve may be configured to securely, but removably, attached to the swab actuator and to invert over the inverting conveyor tube as it rolls and inverts over the elongate tubular shaft. The inverting swab sleeve may include an engagement cap at the first end of the inverted tube that is configured to engage with the inverting conveyer tube. The engagement cap may have a shape that is configured to securely, but releasably, attach to the drive of the swab actuator, and in some cases the inverting conveyer tube of the swab actuator. The engagement cap may insert into (and be captured by) the inverting conveyer tube. For example, the engagement cap may be at one end of the inverting swab sleeve and may have tapered shape that inserts into the lumen of the inverting conveyer tube. Thus, in some examples the engagement cap has a bullet shape. In some examples, the engagement cap comprises a plurality of projections on an outer surface of the engagement cap. Because the inverting conveyer tube inverts into itself when driven by the control, it may capture the end of the inverting swab sleeve (in some examples, the engagement cap that may be on the end of the inverting swab sleeve), and the attachment maybe increasingly secure as the device is actuated, which may prevent the inverting swab sleeve from disengaging from the swab actuator when in use, e.g., preventing it from disengaging when in the body orifice.

In any of the apparatuses described herein, the inverting swab sleeve and/or the elongated tubular shaft may be bent or curved along a length of a distal end of the inverting swab sleeve. The elongated tubular shaft can be straight or bent and may have one or more sections of high, medium and/or low stiffness sections along its length, to help the tube track safely into the patients targeted anatomy (e.g., ear canal). In some examples, the distal end region and/or a mid-region of the elongated tube shaft may have a lower bending stiffness a compared with the rest of the elongated tubular shaft. To vary tube bending stiffnesses along its length, materials (e.g., polymers) of different stiffness/durometers can be assembled, and/or the tube may have sections along its length that have a pattern of cuts (e.g., a laser cut pattern), such as, for example, an interrupted helical cut pattern or other pattern, to make the stiff tube selectively more flexible. As mentioned above, the inverted tube of the inverting swab sleeve comprises one of: a knit, a weave or a braid. In some examples the inverted tube of the inverting swab sleeve comprises an absorbent cellulose fiber. Any of these apparatuses may be configured to include a bulb region on the elongate tubular shaft. The bulb region may be further configured to limit insertion of the system into a subject's ear. For example, the bulb region may have a region of larger radial diameter that is positioned at a distal end region of the elongate tubular shaft (and/or at the distal end). In some cases the bulb region may be offset from the distal end of the elongate tubular shaft.

Any appropriate control may be used as the control of the swab actuator. For example, the control may include one or more of: a slider, a knob, a roller, a dial, or a button.

The inverting swab sleeve may be any appropriate size (length, diameter, etc.). For example, the inverting swab sleeve may have a diameter of between 3 mm and 10 mm, which may be stretchable (e.g., expandable/contractable), including as the inverting swab sleeve extends over the inverting conveyor tube and/or any bulb region. In some examples the inverting swab sleeve device is between about 1.5 and 15 cm long.

The inverting swab sleeve may include a cover (e.g., loading tube) that may protect the swab sleeve until it is ready to be used, and may also help in coupling the swab sleeve to the swab actuator (e.g., the inverting conveyer tube of the swab actuator). For example, a loading tube may cover the inverting swab sleeve, and may be included with the swab sleeve. In some examples the loading tube comprises a centering securement configured to releasably hold an engagement cap at a distal end of the inverted tube in a radially centered region of the loading tube. Any of these apparatuses may include a cuff at the second end of the inverted tube of the inverting swab sleeve.

Also described herein are disposable swabs (disposable inverting swab sleeves, also referred to herein as swab sleeves) for use with the one-handed apparatuses. These swab sleeves may be separate from the system including both the swab actuator and the swab sleeve. For example, an inverting swab sleeve device for use with a swab actuator, the device comprising: an inverting swab sleeve comprising an inverted tube of material configured to fit into an ear canal; and an engagement cap coupled to first end of the inverted tube of absorbent material, wherein the inverted tube is inverted over the engagement cap so that the engagement cap is within the inverted tube, further wherein the engagement cap is configured to engage with the swab actuator.

The inverting swab sleeve may include an inverted tube of absorbent material, such as but not limited to a cellulose fiber material. In general, as mentioned above, the swab sleeve may be formed of any appropriate material, including non-absorbent materials. The inverting swab sleeve may be formed as one or more lengths of filaments (either lengths of the same filament or multiple different filaments), and may be knitted, woven, braided, etc.

The inverting swab sleeve may have any appropriate length and diameter. For example, the inverting swab sleeve may have a diameter of between about 3 mm and 10 mm. In some examples the inverting swab sleeve device may have a length of between about 1.5 and 15 cm long. Any of these apparatuses may include a loading tube covering the inverting swab sleeve. The loading tube may comprise a centering securement configured to releasably hold the engagement cap in a radially centered region of the loading tube. The centering securement may include a projection configured to hold the engagement cap in the radially centered region of the loading tube. For example, the centering securement may comprise a tapered distal end region configured to hold the engagement cap in the radially centered region of the loading tube. The engagement cap may be any appropriate material, such as (but not limited to) a polymeric material. As mentioned, the engagement cap may comprise any appropriate shaped (e.g., tapered/bullet shape, etc.). The engagement cap may have a plurality of projections on an outer surface of the engagement cap; for example, the plurality of projections may comprise one or more of: ridges, bumps, rings, or dimples. The inverting swab sleeve (e.g., inverting swab sleeve device) may include a cuff at the second end of the inverted tube of absorbent material. The cuff may be formed of a low durometer material. For example, the cuff may comprise a tapered and funnel-shaped inner diameter.

For example, an inverting swab sleeve device for use with a swab actuator may include: an inverting swab sleeve comprising an inverted tube of absorbent material; an engagement cap coupled to first end of the inverted tube of absorbent material, wherein the inverted tube is inverted over the engagement cap so that the engagement cap is within the inverted tube; and a cuff at a second end of the inverted tube of absorbent material.

In some examples an inverting swab sleeve device for use with a swab actuator includes: an inverting swab sleeve comprising an inverted tube of knitted, woven or braded absorbent material configured to fit into an ear canal; and an engagement cap coupled to first end of the inverted tube of absorbent material, wherein the inverted tube is inverted over the engagement cap so that the engagement cap is within the inverted tube, further wherein the engagement cap is configured to engage with the swab actuator; and a cuff at a second end of the inverted tube of absorbent material.

Also described herein are inverting swab apparatuses, which may be specifically configured for insertion into an ear. For example, an inverting swab apparatus for insertion into an ear may include: an elongate tubular shaft comprising a first grip region; an inverting swab sleeve comprising an inverted tube of wax-removing material inverting over a distal end of the elongate tubular shaft; and a reciprocating shaft slidably positioned within the elongate tubular shaft, the reciprocating shaft having a second grip region at a proximal end, wherein the reciprocating shaft is coupled to a first end of the inverting swab sleeve at a distal end region, further wherein the inverting swab sleeve is configured to roll and invert over the elongate tubular shaft when the reciprocating shaft is moved proximally relative to the elongate tubular shaft.

For example, an inverting swab apparatus for insertion into an ear may include: an elongate tubular shaft comprising a first grip region; an inverting swab sleeve comprising a knit, woven or braided inverted tube of an absorbent material inverting over a distal end of the elongate tubular shaft; and a reciprocating shaft within the elongate tubular shaft, the reciprocating shaft having a second grip region at a proximal end, wherein the reciprocating shaft is coupled to a first end of the inverting swab sleeve at a distal end region, further wherein the inverting swab sleeve is configured to roll and invert over the elongate tubular shaft when the reciprocating shaft is moved proximally relative to the elongate tubular shaft.

An inverting swab apparatus for insertion into an ear may include: an elongate tubular shaft comprising a first grip region; an inverting swab sleeve comprising a knit, woven or braided tube of absorbent material inverting over a distal end of the elongate tubular shaft; a reciprocating shaft within the elongate tubular shaft, the reciprocating shaft having a second grip region at a proximal end, wherein the reciprocating shaft is coupled to a first end of the inverting swab sleeve at a distal end region, further wherein the inverting swab sleeve is configured to roll and invert over the elongate tubular shaft when the reciprocating shaft is moved proximally relative to the elongate tubular shaft; and a cuff at a second end of the inverting swab sleeve.

The elongate tubular shaft may be bent or curved at a distal end region. The bend/curvature may be configured or adapted for use within the patient's ear.

In any of these apparatuses the swab may include a cuff at a second end of the inverting swab sleeve; the cuff may be use for manual retraction of inverting sleeve. For example, the swab sleeve may be inserted into an ear, and the reciprocating shaft may be pulled proximally to roll and invert the swab sleeve over the elongate tubular shaft, pulling in material from the ear. Once fully inverted, the device may be removed from the ear and inverted back over itself by pulling on the cuff to manually reset the swab sleeve. In general, the cuff may be relatively soft and compliant. For example, the cuff may comprise a low durometer material (e.g., a material having a durometer of less than 80 on the Shore 00 scale (e.g., between 10 and 70 on the ShoreA scale, etc.). In any of these examples the cuff may include a tapered and funnel-shaped inner diameter.

As mentioned, the inverting swab sleeve may be formed of a plurality of lengths of filament lengths, and may be, e.g., a knit, a weave or a braid. The inverting swab sleeve may comprise an absorbent material, for example, the inverting swab sleeve may comprise an absorbent cellulose fiber. Any of these apparatuses may include a bulb region on the elongate tubular shaft configured to limit insertion of the apparatus into a subject's ear. For example, the bulb may be positioned at a distal end region of the elongate tubular shaft.

In any of these apparatuses, the inverting swab sleeve is configured to be reset by sliding a second end of the inverting swab sleeve proximally after the reciprocating shaft has been moved proximally to a fully extended position. Any of these examples may include a stop configured to prevent the reciprocating shaft from extending proximally beyond a fully extended position.

Also described herein are methods of using any of these apparatuses. For example, described herein are method of using any of these apparatuses to clean an ear, comprising:

inserting an inverting swab sleeve into the ear, wherein the inverting swab sleeve comprises a tube of material that is inverted into itself; moving a shaft coupled to the inverting swab sleeve to roll and invert the inverting swab sleeve into itself to capture wax material from the ear; and removing the inverting swab sleeve from the ear.

For example, a method may include: inserting an inverting swab sleeve into the ear, wherein the inverting swab sleeve comprises a tube of material that is inverted into itself; moving a shaft coupled to the inverting swab sleeve to roll and invert the inverting swab sleeve into itself to capture wax material from the ear; and removing the inverting swab sleeve from the ear. Any of these methods may be used in any other body region, such as the nose, belly button, between the toes, behind the ears, etc.

Any of these methods may include loading the inverting swab sleeve onto a swab actuator.

In general, inserting the inverting swab sleeve may comprise inserting the inverting swab sleeve unit a bulb region prevents further insertion. In some examples the method may include loading the inverting swab sleeve onto a swab actuator by capturing an engagement cap that is coupled to first end of the inverting swab sleeve in an inverting conveyer tube of the swab actuator. In some examples inserting the inverting swab sleeve comprises inserting an absorbent inverting swab sleeve into the ear.

In any of these examples moving the shaft comprises operating a control of a driver to move the shaft. For example, moving the shaft comprises using a single hand to move the shaft and to hold the inverting swab sleeve in the ear.

In some cases operating the control comprises moving a slider.

Also described herein are nasal inverting swab apparatus. These apparatuses may be the same as the apparatuses described above, but may be adapted for use in the ear. For example, in some variations the apparatus includes: an elongate tubular shaft; an inverting swab sleeve comprising an inverted tube; a driver for driving inversion of the inverting swab sleeve over the elongate tubular shaft, wherein the driver comprises a reciprocating shaft, further wherein a first end of the inverting swab sleeve is coupled to the reciprocating shaft; a first bias to a first end of the inverting swab sleeve; a second count-bias coupled to a second end of the inverting swab sleeve, wherein the second counter-bias is configured to be displaced by applying force to the reciprocating shaft so release of the displacement pulls the inverting swab so that it rolls and inverts over the elongate tubular shaft; and a control for operating the driver. The elongate tubular shaft may comprise one or more ports for aspiration and/or irrigation. In some examples the controller comprises a pusher/puller control at a proximal end of the reciprocating shaft.

In some examples, an inverting swab apparatus may comprising: an elongate tubular shaft; an absorbent material at a distal end of the elongate tubular shaft; an inverting swab sleeve comprising an inverted tube extending over an external surface of the elongate tubular shaft and absorbent material and inverting over a distal end of the elongate tubular shaft; and a driver for driving inversion of the inverting swab sleeve over the distal end of the elongate tubular shaft, wherein the driver comprises a reciprocating shaft. The inverting swab sleeve may comprise a knitted, woven or braided tube.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1A shows the inverting sleeve swab apparatus ready for use. FIG. 1B shows the inverting sleeve swab apparatus being re-set.

FIG. 3A shows an example of filaments of an absorbent material (e.g. cellulose fiber, such as Rayon) that may be used to form the swab sleeve material. The filaments are shown under 40× magnification. FIG. 3B shows an example of a portion of a swab sleeve formed from a knitted absorbent material (e.g., tubular knit of absorbent/superabsorbent filaments). FIG. 3C shows a lower-resolution example of a swab sleeve formed from a knitted absorbent material. FIG. 3D shows another example of a swab sleeve formed from a knitted non-absorbent material formed as a tubular knit of a nylon monofilament (shown inverted).

FIGS. 4A-4C illustrate examples of filament patterns that may be used to form a swab sleeve of an inverting sleeve swab apparatus. FIG. 4A shows an example of a woven filament pattern. FIG. 4B shows an example of a weft knitted filament pattern. FIG. 4C shows an example of a warp knitted filament pattern.

FIGS. 5A-5D illustrate an example of an inverting sleeve swab apparatus ingesting a wax material.

FIGS. 6A-6C illustrate an example of an inverting sleeve swab apparatus removing a wax material from within a transparent model of an ear canal.

FIG. 25 illustrates one example of an inverting swab sleeve assembly loaded onto a swab actuator.

FIG. 26 schematically illustrates an engagement cap for use with an inverting swab sleeve.

FIGS. 27A-27C show exemplary cross-sectional profiles for variations of an engagement cap for an inverting swab sleeve assembly.

FIGS. 28A-28C illustrate examples of engagement cap regions for an inverting swab sleeve assembly.

FIGS. 29A-29G schematically illustrate examples of engagement cap regions for an inverting swab sleeve assembly.

FIGS. 36A-36D illustrate another example of an inverting swab system including a rotary control.

FIGS. 37A-37D schematically illustrate operation of an inverting swab system similar to that shown in FIGS. 36A-36D.

FIGS. 56A-56B schematically show an example of an inverting swab apparatus including a spring (bias) for deploying the device.

DETAILED DESCRIPTION

Described herein are inverting swab apparatuses that may provide a safer and more effective swab than traditional swabs for use in the ears, nose or other body regions. These apparatuses may be used to remove moisture (e.g., drying), oil, and moderate built up of wax (e.g., ear wax) or debris from the body, including from the ear canal. These apparatuses (devices, systems, etc.) are safer than traditional swabs because they do not compact the material against the wall of the body region (e.g., ear canal). In addition, they may be sized and configured to prevent harm from insertion and operation within the body. Although many of the examples described herein are specific to use in the ear, the inverting swab apparatuses described herein are not limited to use in the ear, but may be used within the nose or other body region. For example, when used in the nose, they may help in resisting congestion, and may remove or relieve snot, phlegm and/or mucus from the body. In some cases these apparatuses may be adapted for use in infants and/or toddlers, in order to remove mucus as an alternative to air aspiration. Also described herein are apparatuses for removing a material, such as a stone (e.g., kidney stone, gall stone, bladder stone, urinary tract stone, etc.) from a body.

As will be described in greater detail herein, these apparatuses may be configured as reusable and/or disposable components, and may be configured for one handed and/or two handed use, and may generally work with a variety of hand sizes. In general, these apparatuses may provide sufficient grip for one handed use and may generate sufficient force for operation of the device to invert and remove material. In addition, these apparatuses may be configured for use at a variety of different depths into a body region, and may limit the insertion depth to enhance safety. In general, these apparatuses are configured so as to be both effective and easy to operate.

Figure 1A:
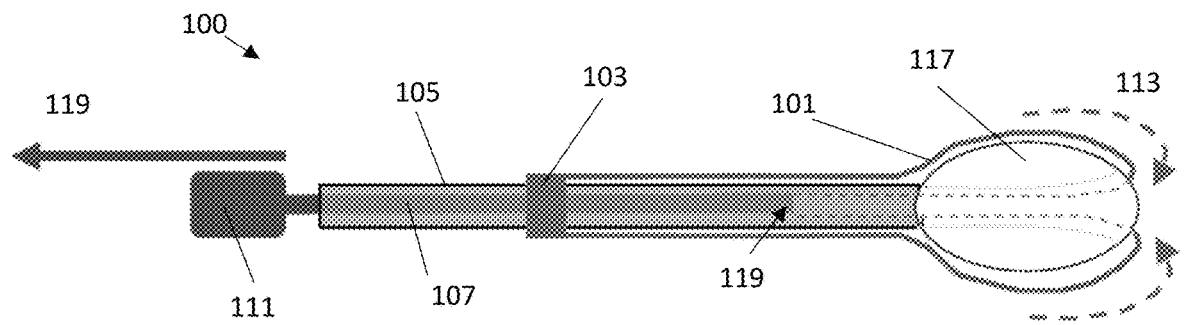
FIGS. 1A and 1B illustrate an example of an inverting sleeve swab apparatus.
Figure 1B:
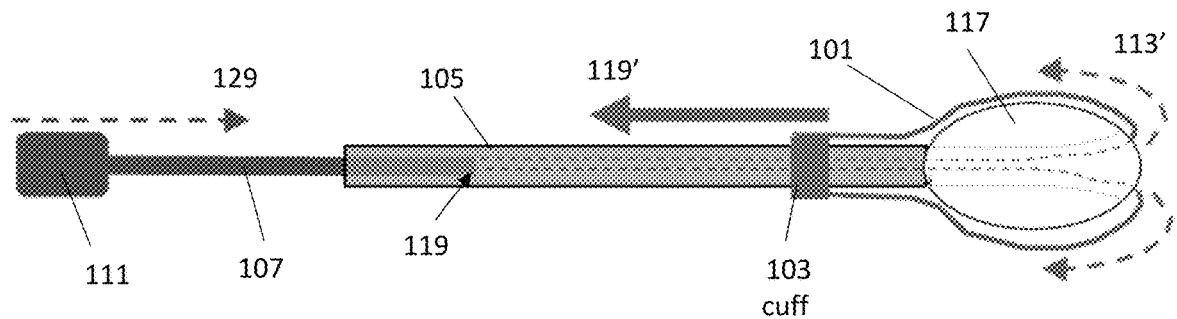

FIGS. 1A-1B illustrate a first example of inverting swab apparatus having an inverting swab sleeve. In this example the inverting swab apparatus 100 has an elongate tubular shaft 105 that extends, e.g., between about 4-25 cm (e.g., between about 5-23 cm, between about 5-20 cm, between about 5-18 cm, between about 5-15 cm, between about 5-13 cm, between about 5-10 cm, etc.). In general, the elongate tubular shaft may support an inverting swab sleeve 101. The elongate tubular shaft may be referred to as an outer tube shaft in some examples, as it is outside of the driver (e.g., reciprocating shaft 107) which is coaxially positioned within the elongate tubular shaft. In some examples the tubular shaft may form an outer surface of the device, which may be gripped; alternatively in some examples it may be inside or partially inside a housing and/or covered by the inverting swab sleeve.

The inverting swab sleeve 101 extends distally over the elongate tubular shaft 105 and inverts at the distal end into itself, to extend back towards the proximal end. The inverting swab sleeve may be referred to as simply the swab sleeve, and may be functionally connected to the driver (reciprocating shaft 107) that is slideably positioned within the elongate tubular shaft. The opposite end of the inverting swab sleeve may be freely sildeable over the elongate tubular shaft 1015 and may include an optional cuff 103 at the distal end. The cuff may form an engagement site that may be pulled (or optionally, pushed) to reset or "reactivate" 119' the inverting swab sleeve to an initial configuration.

In FIGS. 1A-1B, the proximal end of the device includes a control (inverting control) 111, which is coupled to the driver 107 and is configured as a puller in this example. The control 111 may be shaped and configured for gripping by the user's fingers. In some examples the inverting control may be part of the driver 107, e.g., as a region at the proximal end of the driver that can be pulled by the user. Thus, the apparatus does not need to have a separate inverting control 111, though it may be beneficial to provide a gripping region.

The inverting swab example shown in FIG. 1A also includes a bulb region 117 at the distal end region. The bulb region (which may be referred to simply as the bulb) may be formed integrally with the elongate tubular shaft 105, or it may be separately attached to the elongate tubular shaft 105. In some examples the bulb is a rounded protrusion having an outer diameter that is greater than the outer diameter of the outer shaft. The bulb 117 may be rounded or curved. In general, the swab sleeve may extend over the bulb. The slightly larger diameter of the bulb may prevent the swab sleeve 101 from pulling completely over the distal end of the device and inverting fully into itself. In some examples the bulb may also prevent or limit over-insertion of the swab 100. The bulb may be at the distal end region of the swab 100 device as shown in FIGS. 1A-1B, or it may be proximally offset. However, as described in FIG. 2, below, the bulb is optional, and the inverting swab may not include a bulb.

The inverting swab sleeve 101 may couple at one end (or one end region) to the driver 107 (e.g., reciprocating shaft). In some examples the inverting swab sleeve may be attached to the driver at an attachment interface 119. In some examples the attachment interface is an adhesive and/or mechanical attachment. For example the swab sleeve may be crimped to the driver 107. In some examples the attachment interface may be an adhesive and the swab sleeve 101 may be glued to the driver (e.g., shaft 107).

FIGS. 1A-1B also illustrate operation of the inverting swab device 100. In general, the inverting swab device 100 have an initial, undeployed configuration (similar to that shown in FIG. 1A) and a deployed configuration (similar to that shown in FIG. 1B), in which the inverting swab sleeve has been nearly fully (or in some cases, fully) deployed and inverted over itself at the distal end of the device. The inverting swab 100 may start in the undeployed configuration (or may be set or reset to the undeployed configuration) so that the swab sleeve 101 is minimally inverted over itself and extends over the outer tubular shaft 105 (and optional bulb 117). The control (inverting control 111) is in an undeployed configuration; in FIG. 1A, the inverting control 111 at the distal end of the driver 107 is distally positioned near the proximal end of the outer tubular shaft 105.

In this example, the device may be activated by pulling the control 111 proximally 119, typically while holding onto a portion of the outer tubular shaft 105 (e.g., a grip region between the end of the swab sleeve and the proximal end of the outer tubular shaft). Pulling the control 111 proximally moves the driver 107 proximally which in turn pulls the portion of the flexible swab sleeve 101 that is within the outer tubular shaft (e.g., the end coupled to the driver) proximally and causes the swab sleeve to invert 113 into itself, siding over the distal end region of the device, as it is pulled into the outer tubular shaft. In this example the device is driven over the bulb region 117 and the cuff 103 at the end of the swab sleeve slides freely over the outer tubular shaft. The rolling and inverting at the distal end region of the inverting swab may rub against an inner surface of the body region, such as within the ear canal, and may absorb fluid and may collect material (including wax, debris, particulate material, etc.) from within the body region that may be trapped and captured by the inverting swab sleeve as it rolls into the body. The amount of fluid absorption and/or the degree of rubbing or scrapping may be determined by the materials used to form the swab sleeve 101 and/or by the structure of the swab sleeve, such as the density or morphology of the weave, braid, and/or knit, as well as the diameter of the lengths of filaments forming the weave, braid and/or knit.

In FIG. 1B the inverting swab 100 is shown nearly completely inverted. In some cases, the inverting swab may be reset or reactivated, e.g., by pulling the cuff 103 proximally 119' while either allowing the driver 107 and attached control 111 to passively reset and slide distally or by actively moving them distally. Resetting the swab sleeve 101 in this manner may re-invert the swab sleeve 113' over the distal end of the device and may eject any material that was captured by the swab sleeve. Thus, this step may be performed outside of the body, for example.

Figure 2:
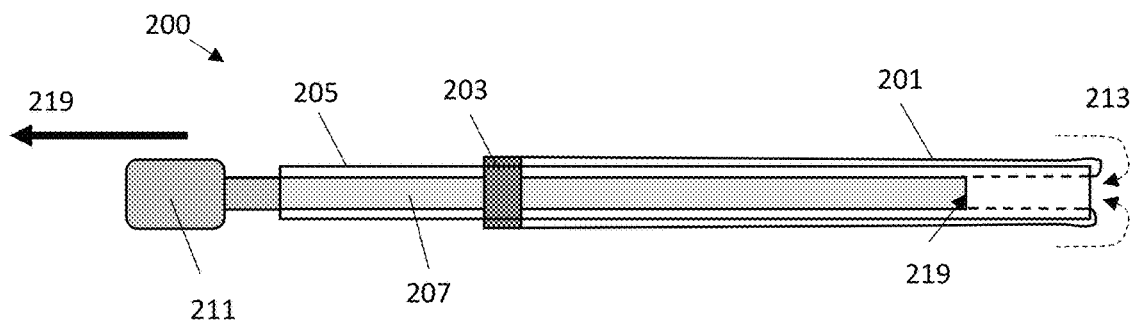
FIG. 2 shows an example of an inverting sleeve swab apparatus.

FIG. 2 shows another example of an inverting swab 200 that includes most of the elements of the inverting swab shown in FIGS. 1A-1B, except for the optional bulb 117. For example, in FIG. 2 the device includes an elongate tubular shaft 205 and a driver 207 coaxially and slidably arranged within the elongate tubular shaft. The driver 207 in this example is configured to include a reciprocating shaft. The distal end of the shaft may be configured as a control or may be coupled to a control 211 (e.g., inverting control) such as a puller or grip region for activating movement 219 of the inverting swab sleeve 201. The inverting swab sleeve 201 is attached (e.g., at an attachment interface 219) to the distal end region of the driver 207 within the lumen of the elongate tubular shaft 205. The opposite end of the swab sleeve 201 extends over the outer surface of the elongate tubular shaft 205 and, in this example, ends in a cuff region 203. The inverting swab device shown in FIG. 2 may be operated as shown in FIGS. 1A-1B; pulling the proximal end of the driver 207 (e.g., pulling the control 211) pulls the first (internal) end of the swab sleeve 201 proximally, inverting the swab sleeve over itself as it rolls 213 over the distal end of the device and is drawn into the lumen of the elongate tubular shaft 205.

In any of the inverting swabs described herein, the inverting swab sleeve may be relatively compliant, and may be sufficiently flexible so that it can be pulled over and inverted into itself. The swab sleeve is generally tubular and may extend to an un-inverted length of between about 1 cm to about 15 cm or longer (e.g., between about 1 cm to about 15 cm, between about 1 cm to 14 cm, between about 1 cm to 13 cm, between about 1 cm to 12 cm, between about 1 cm to 11 cm, between about 1 cm to 10 cm, between about 1 cm to 9 cm, between about 1 cm to 8 cm, between about 1 cm to 7 cm, etc.). The swab sleeve may be sufficiently compliant (e.g., soft) and flexible so that it may stretch and compress. In some examples the swab sleeve has a relaxed diameter of between about 2 mm and 20 mm (e.g., between about 3 mm and 15 mm, between about 3 mm and 12 mm, between about 3 mm and 10 mm, between about 3 mm and 9 mm, between about 3 mm and 8 mm, between about 3 mm and 7 mm, between about 3 mm and 6 mm, between about 3 mm and 5 mm, etc.). The swab sleeve may be constructed to have an inner diameter (when tensioned) that has similar or slightly larger diameter than the elongated tube outer diameter. Sizing the swab sleeve diameter in this way may help prevent the swab sleeve from binding down on the elongated tube and/or inverting conveyor tube when actuated by the user.

The swab sleeve may be formed of a plurality of lengths of filament that may be woven, knitted, braided, etc. In some examples the swab sleeve may be non-woven. In some examples the swab sleeve is formed as a flat woven, flat laminated, flat braided of flat knitted structure that is rolled and sewn/fused into a tubular shape. Alternatively, the swab sleeve may be formed directly as a tubular structure, such as a tubular braid or knit structure.

In general, the swab sleeve may be formed of one or more filaments of any appropriate material and may be laminated and/or coated. In some examples the swab sleeve may be absorbent (e.g., water absorbent and/or oil absorbent). For example, the swab sleeve may be configured as a knitted, braided or woven structure having a pattern that forms channels or pores to allow wicking of liquid into the pattern to retain fluid. Alternatively or additionally, the swab sleeve may be formed of an absorbent (fluid-absorbent) material, such as cellulose. For example, the swab sleeve may be formed of a hydrophilic material, such as (but not limited to) Cellulose Nanofibril Hydrogels. In some examples, the swab sleeve may be formed of fibers of Rayon, Lyocell, and/or Tencel. The swab sleeve may be formed of a cellulose yarn of any appropriate size (e.g., between about 50-500 denier). In some examples the swab sleeve may be formed of a natural fiber, such as a cotton fiber (e.g., bulk cotton, cotton yarns, cotton plied yarns, etc.). The filaments forming the swab sleeve may be single-filaments or compound filaments (e.g., formed of 2 or more, e.g., between 2-10 filaments twisted together). For example, the swab sleeve may be formed of a cotton yarn having a size of between about 2-90 Ne size (e.g., between about 10 and 30 ne, etc.).

In some examples the swab sleeve may be formed of a monofilament or multifilament polymeric material, such as a plastic like PET, nylon, or Polypropylene. Alternatively or additionally, the swab sleeve may be formed of a metallic material (e.g., Nitinol, stainless steel, etc.). Mixtures of any of these materials may be used. In some examples the filament size may range between about 0.0005" to 0.010" diameter.

For example, in some examples the swab sleeve may be formed of a cotton material that can be first plied or twisted around a nylon or PET monofilament. This structure may then be knitted, braided or woven. For example, in some cases the swab sleeve may be formed as a co-knit with a Nylon monofilament (which may help with grabbing wax, and debris) and a cotton filament (which may enhance water absorption). Thus, in some examples the swab sleeve may be formed of a combination of cotton yarn (e.g., which may enhance moisture absorbance and softness) and a Nylon monofilament (which may enhance the ability to grab and/or pull out debris, wax and other materials).

In some examples, the swab sleeve may be formed as a tubular knit structure having a plurality of loops formed by a stich lengths such the loops can protrude between about 0.1 and 5.0 mm (e.g., between about 0.1 mm to 1 mm, or greater) away from the distal end of the inverting tube or bulb as it inverts. Protrusion of the knit loop may aid in grabbing debris, mucus, wax, etc., and/or may increase the contact between the swab sleeve and the body region to increase contact for absorbing fluid (e.g., water) from within the body.

Figure 3A:
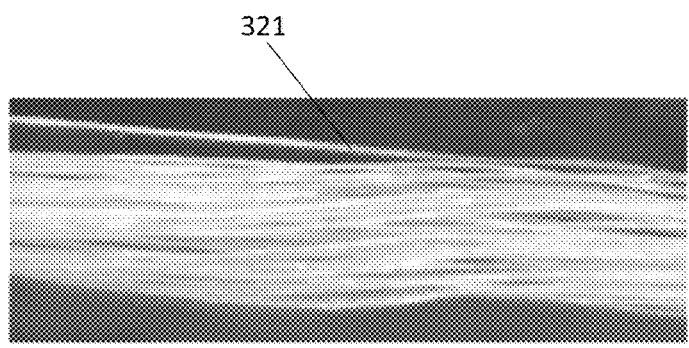
FIGS. 3A-3D illustrate examples of the swab sleeve material.
Figure 3B:
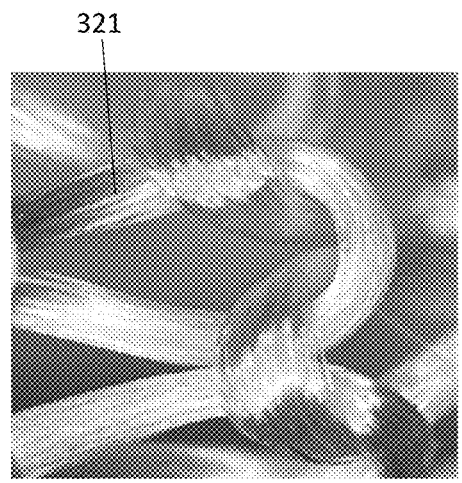
Figure 3C:
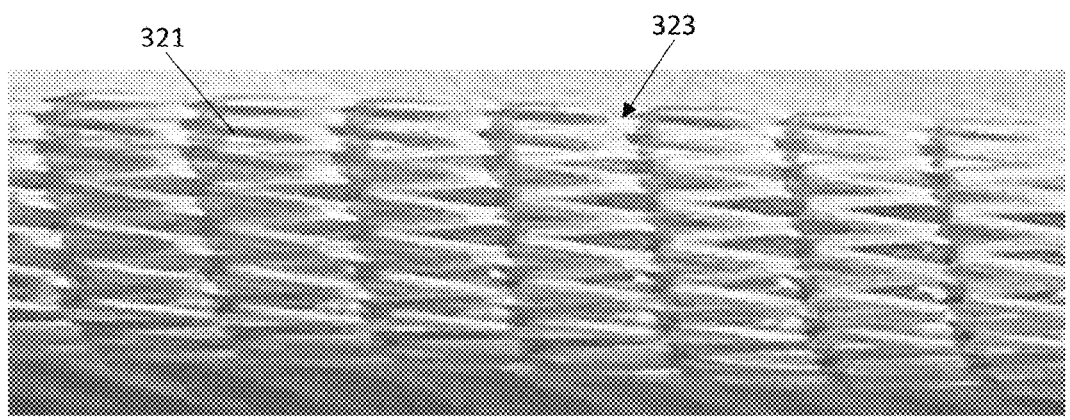

FIGS. 3A-3D illustrate examples of filaments 321 (shown in an enlarged view in FIG. 3A) and patterns of knitted filaments (shown in FIGS. 3B-3C). In FIG. 3A the filaments 321 are cellulose fiber (Rayon) filaments under 40× magnification. The filaments may be combined to form a multi-filament length that may be woven, braided or, in FIGS. 3B-3D, knitted. FIG. 3B shows an enlarged view of a portion of a tubular knit filament 321 formed of the cellulose fibers shown in FIG. 3A. FIG. 3C shows the knitted tube 323 forming the swab sleeve.

Figure 3D:
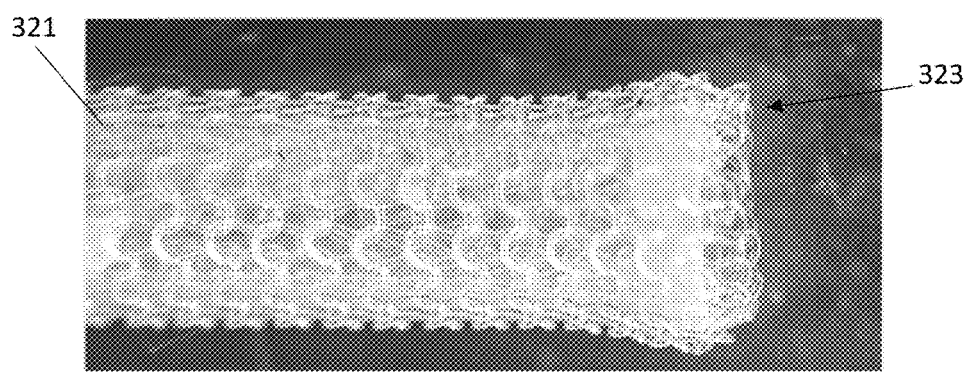

FIG. 3D illustrates an example of a tubular knit of nylon monofilament (shown inverted over a PTFE tube, which may form the outer tubular shaft and/or bulb region).

FIGS. 4A-4C illustrate examples of woven (FIG. 4A) and knitted (FIGS. 4B-4C) patterns that may be used to form a swab sleeve. In FIG. 4A the woven fabric shows a plurality of filaments 421 woven in a pattern. The filaments may be the same material or different materials. In this example the weave is approximately 90 degrees relative to non-parallel filaments. Alternatively in some examples the angle between the filaments may be less than 90 degrees, forming a braided material for the swab sleeve.

FIGS. 4B and 4C show examples of knitted materials forming the swab sleeve. In FIG. 4B the knit is a weft knitted fabric formed by knitting a filament 421 in the pattern shown. Alternatively, virtually any other knitted pattern may be used, including a warp knitted pattern, shown in FIG. 4C.

FIGS. 5A-5D illustrate an example of a swab sleeve of any of the device described herein ingesting a solid material (e.g., a wax material) when actuated so that the swab sleeve is inverting and rolling into the device. FIG. 5A shows the swab sleeve 501 adjacent to a piece of wax (e.g., ear wax) material 524. The swab sleeve may be actuated so that it rolls into itself, as shown in FIGS. 5B-5D, showing the progression of the ingestion of the wax material 524 as the swab sleeve is rolled into itself to invert 513. By FIG. 5D, the wax material has been completely ingested.

A similar illustration is shown in FIGS. 6A-6C, showing the distal end of device, including the saw sleeve 601, inserted into a transparent model of an ear canal that is sized approximately equivalent to a human ear canal. In FIG. 6A the swab sleeve 601 is inserted partially into the ear canal, and a wax material 624 is shown present against the wall (and partially blocking) the ear canal model. In this example, as the swab sleeve is inserted distally into the ear canal, or after it has been inserted, the swab sleeve is actuated so that it rolls into itself; as it rolls and inverted over the distal end, the swab sleeve material rubs gently against the walls of the ear canal, engaging with the wax material 624, as shown in FIGS. 6B and 6C, capturing the wax material with the swab sleeve within the lumen of the outer tubular shaft 605.

Figure 7:
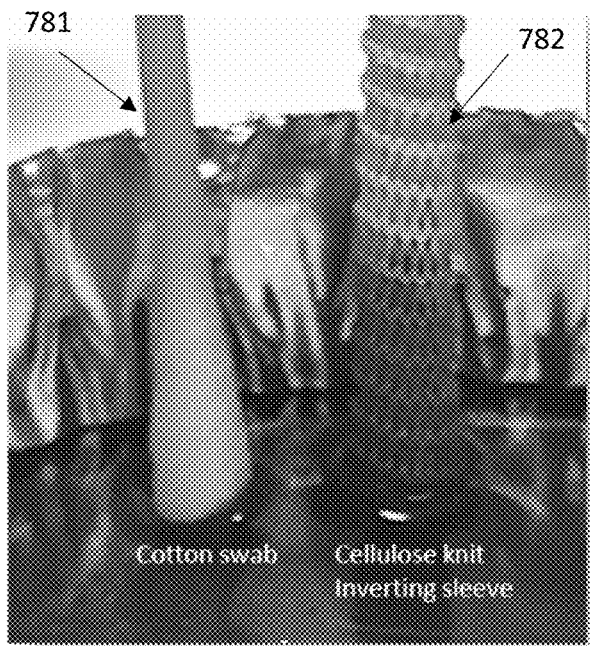
FIG. 7 shows a comparison of the absorption of an inverting sleeve swab apparatus as compared to a commercially available cotton swab. In this example, the inverting sleeve swab apparatus as described herein absorbed fluid five fold (5×) faster than the cotton swab.
Figure 8:
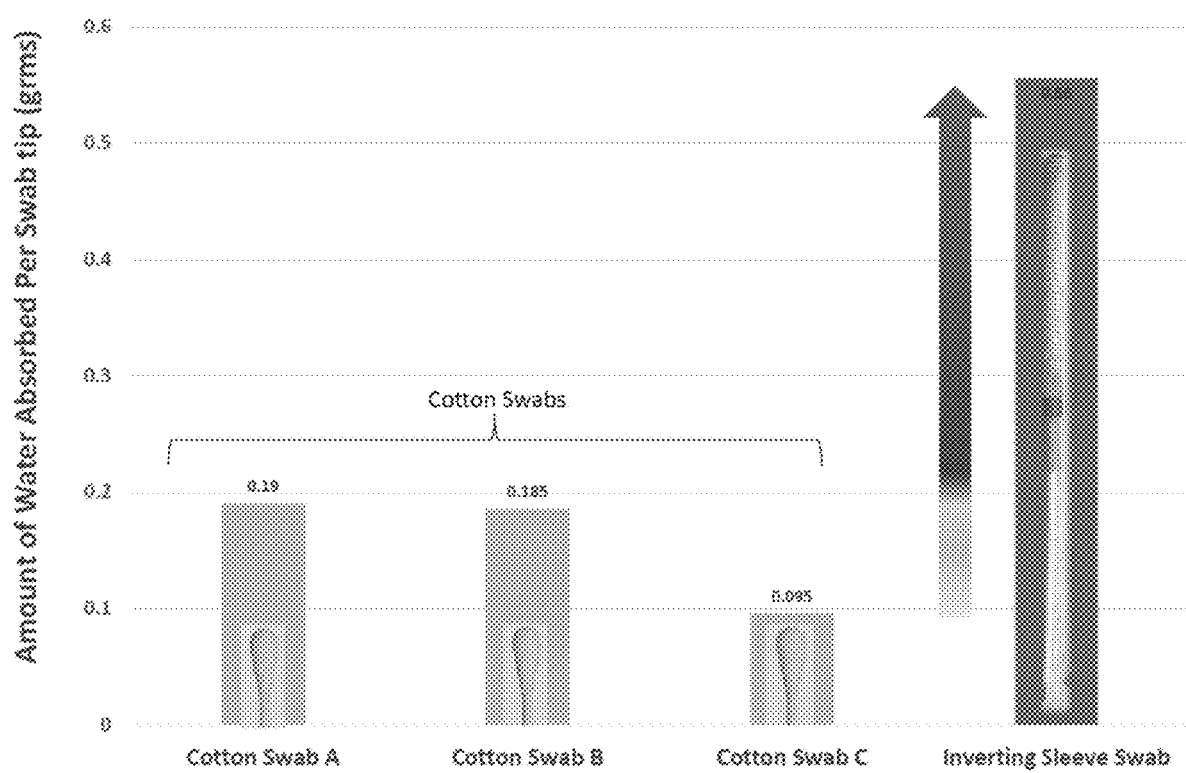
FIG. 8 is a graph comparing the amount of fluid (e.g., water) absorbed by various commercially available cotton swabs as compared with an inverting sleeve swab apparatus as described herein. The inverting sleeve swab apparatus was many times more absorbent than the cotton swabs.

In addition to solid materials, these apparatus may be particularly useful for removing liquid material, and may be absorbent (e.g., super absorbent). For example, FIGS. 7 and 8 show a comparison between an inverting swab device (e.g., having a swab sleeve) 782 as described herein and a traditional cotton swab 781. In FIG. 7 the traditional cotton swab 781 is shown side-by-side with the swab sleeve of an inverting swab device 782 in which the ends of each are in contact (and partially submerged) within a pool of water that has be dyed to show absorption into the devices. The inverting swab device is shown in a static state, in which the swab sleeve is not rolled into the device (which would be expected to increase the absorbent surface area), but is held in the same position. When inserted for equivalent lengths of time, the water absorbency of the swab sleeve as compared to the cotton swab was significantly greater, even in the static condition shown in FIG. 7 and apparent by the blue staining shown extending up the length of the swab sleeve. In contrast, the cotton swab has absorbed only a small amount of fluid. In general, the swab sleeve in these examples (particularly when formed of a cellulose fiber) may absorb fluid more than five times more quickly than a cotton swab, even in the static configuration. This rate may be even faster in when rolling the swab sleeve, increasing the effective surface area.

FIG. 8 shows a comparison between the total amount of water absorbed per swab tip by a traditional cotton swab versus an inverting swab sleeve. In FIG. 8, three different commercially available cotton swabs were used and compared to an inverting swab sleeve as described herein. The inverting swab sleeve absorbed more than twice the total amount of fluid as compared with the most absorbent of the cotton swabs (e.g., between 2.8 and 5.3 times as much fluid, on average).

Examples

Figure 9:
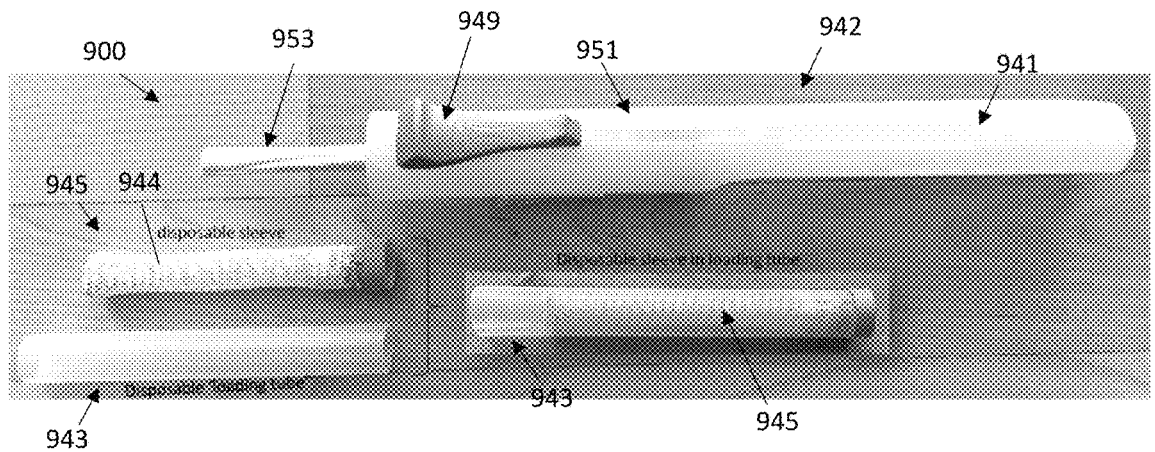
FIG. 9 shows an example of an inverting swab system.

FIG. 9 illustrates another example of an inverting swab apparatus. In this example the inverting swab may be part of a system including a reusable swab actuator and a disposable (e.g., single-use) inverting swab sleeve assembly. In FIG. 9, the system 900 (inverting swab system) includes a swab actuator having a handle region 941 with a handle body 951 housing a driver (not visible in FIG. 9) that includes a reciprocating shaft that is coupled to, and drives movement of, an inverting convey tube 953. The inverting conveyer tube is configured to roll and invert over the elongate tubular shaft as the reciprocating shaft is moved. The inverting conveyor tube is configured to releasably engage with an inverting swab sleeve assembly (e.g., a disposable inverting swab sleeve assembly 945) that may be loaded/unloaded onto the inverting conveyor tube. Thus, the inverting conveyor tube 953 of the device may be reciprocally rolled and inverted into itself (and into the elongate tubular shaft or rolled in an opposite direction and un-inverted out of itself (and out of the elongate tubular shaft) by operating a control 949 on the swab actuator.

Figure 10A:
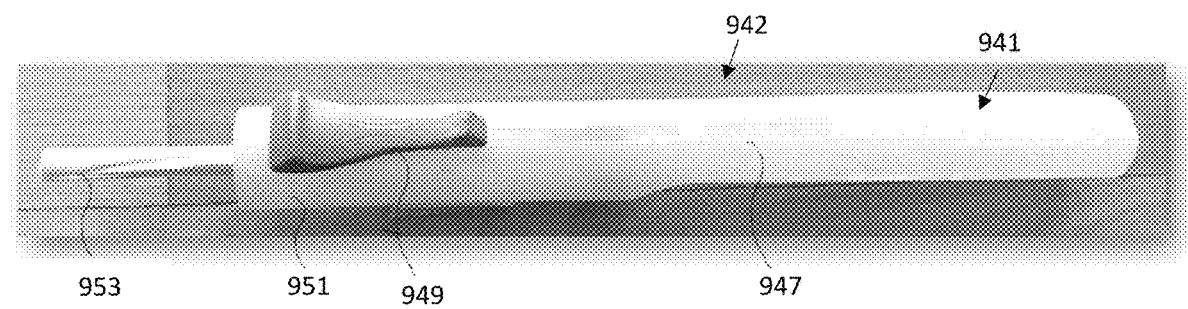
FIG. 10A shows an example of the swab activator of the system shown in FIG. 9.
Figure 10B:
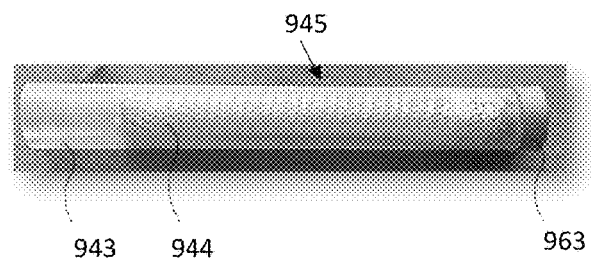
FIG. 10B shows an example of the inverting swab sleeve assembly of the system shown in FIG. 9.

The system 900 shown in FIG. 9 also includes a disposable inverting swab sleeve assembly 945 that may be housed within a loading device (e.g., loading tube 943), as shown. FIGS. 10A and 10B illustrate examples of the components of the system 900 shown in FIG. 9. FIG. 10A shows the swab actuator 942 including a handle 941 having a handle body 951. The handle may be shaped and configured to be held in a user's hand for singe-hand operation of the inverting swab. In FIGS. 9 and 10A the swab actuator includes a control 949 that is configured as a slider that may slide along the length of the handle body within a slot or channel 947 in order to reciprocate the inverting conveyor tube 953. In FIGS. 9 and 10A the swab actuator is shown without a swab sleeve 945 attached. FIG. 10B shows an example of a swab sleeve assembly 945 that may be removably engaged with the swab actuator. In FIG. 10B the inverting swab sleeve assembly 945 includes the flexible inverting sleeve 944 formed as a knit tube of absorbent filaments. The disposable swab sleeve also includes a sleeve cuff 963 attached to one end of the knit tube forming the swab sleeve. The disposable swab sleeve may also include an engagement cap (not shown in FIG. 10B) for assisting in coupling the disposable swab sleeve to the inverting conveyor tube. In FIG. 10B the disposable inverting swab sleeve assembly 945 is also shown enclosed in a loading tube 943 that may protect the inverting swab sleeve and may provide a structure to hold and support the inverting swab sleeve 944 while loading and/or unloading. The loading tube may be open at one or both ends. The swab sleeve 944 may be any of the swab sleeves described herein.

Figure 11A:
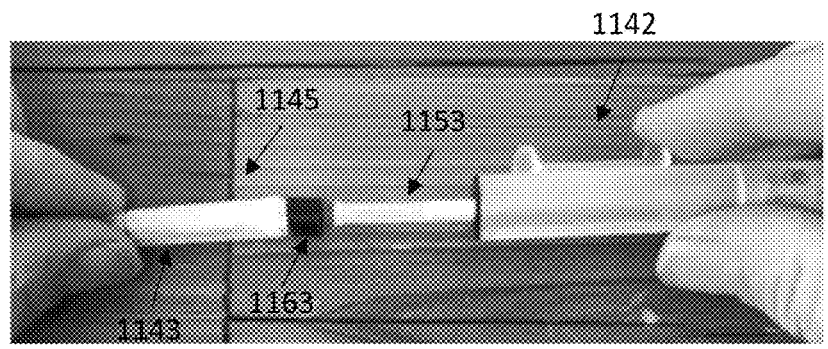
FIGS. 11A-11D illustrate one method of loading an inverting swab sleeve assembly onto a swab activator for a system such as the inverting swab system shown in FIG. 9.
Figure 11B:
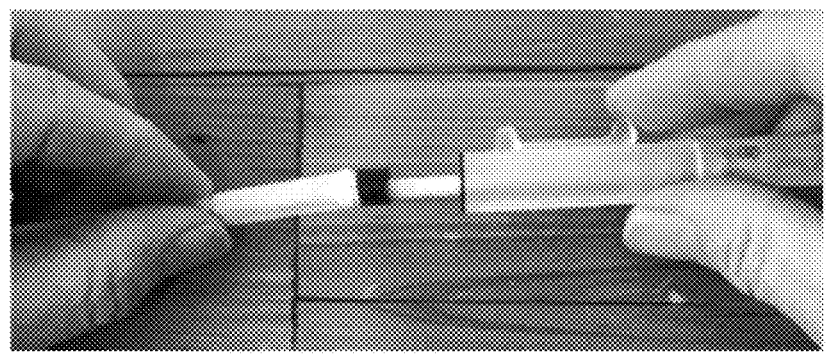
Figure 11C:
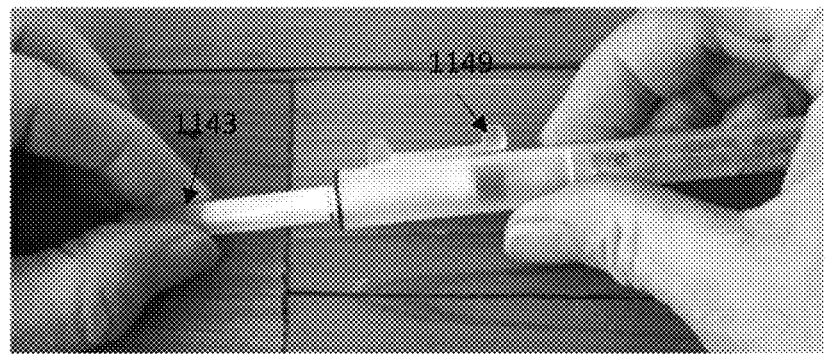
Figure 11D:
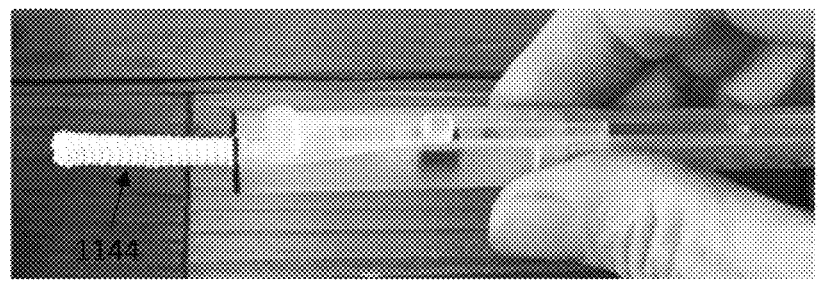
Figure 24A:
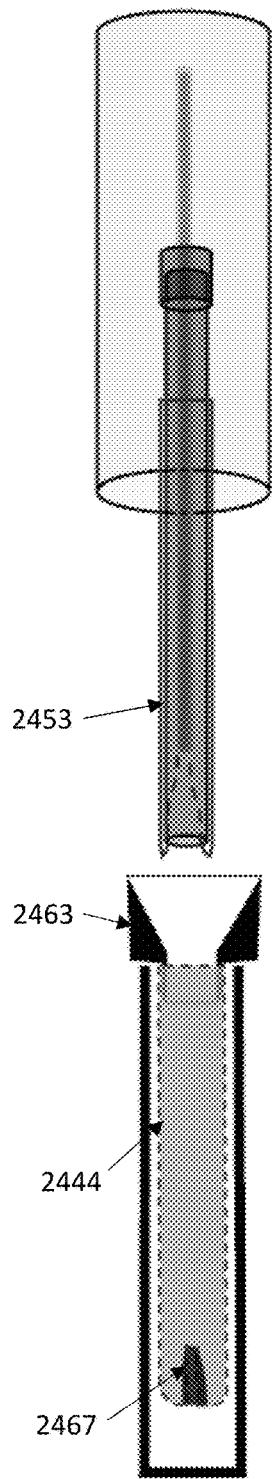
FIG. 24A-24C schematically illustrate coupling of an inverting swab sleeve assembly to a distal end of a swab actuator as described herein.
Figure 24B:
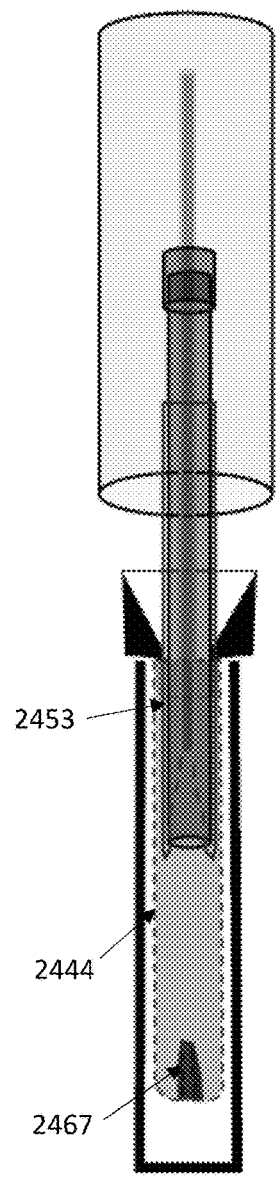
Figure 24C:
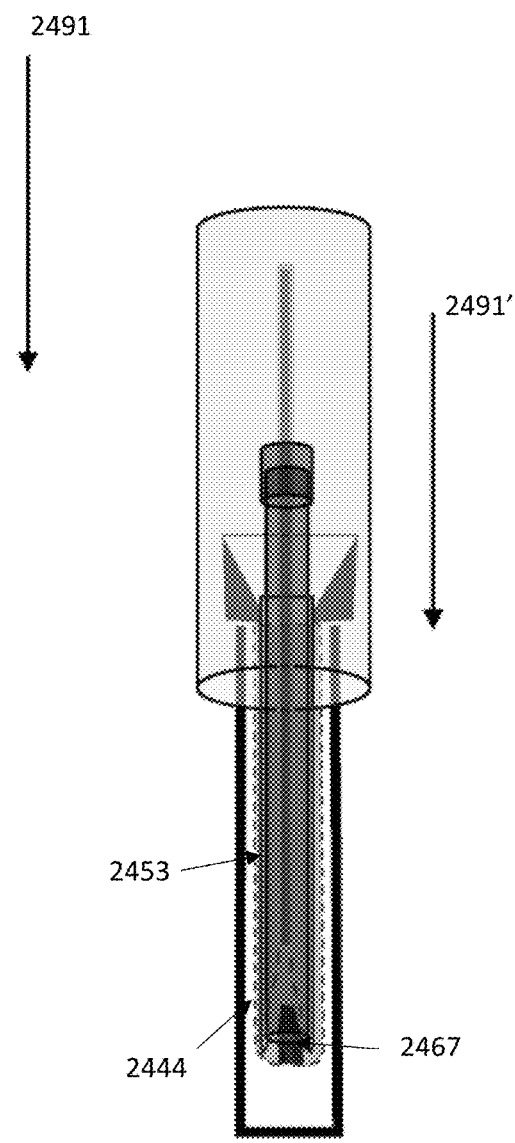

FIGS. 11A-11D illustrate one example of a method of loading an inverting swab sleeve assembly 1145 onto a swab actuator 1142, for a system similar to that shown in FIGS. 9 and 10A-10B. In FIG. 11A the inverting swab sleeve assembly 1145 within a loading tube is positioned so that the cuff 1163 of the inverting swab sleeve assembly 1145 is aligned with the inverting conveyor tube 1153 of the swab actuator 1142. As shown in FIG. 11B, the inverting conveyor tube may then be inserted through the cuff and into the lumen of the swab sleeve 1144, until the inverting conveyor tube is fully inserted, as shown in FIG. 11C. Optionally the inverting conveyor tube may be actuated to invert into itself by operating the control 1149, shown as a slider on the body of the handle of the swab actuator 1142 in this example. This may engage with the more distal end of the swab sleeve 1144, e.g., by engaging with an engagement cap as illustrated in FIGS. 24A-24C. Once the disposable inverting swab sleeve is coupled as shown in FIG. 11C, the loading tube 1143 may be removed, e.g., by pulling and sliding it distally away from the inverting swab sleeve, so that the device is ready to be inserted into the body and actuated, as shown in FIG. 11D.

Figure 12A:
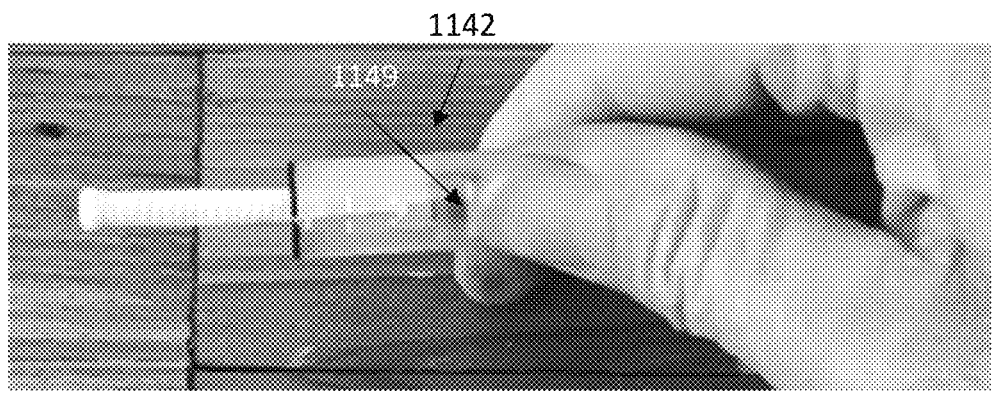
FIGS. 12A-12C illustrate operation of an inverting swab system similar to that shown in FIG. 9.
Figure 12B:
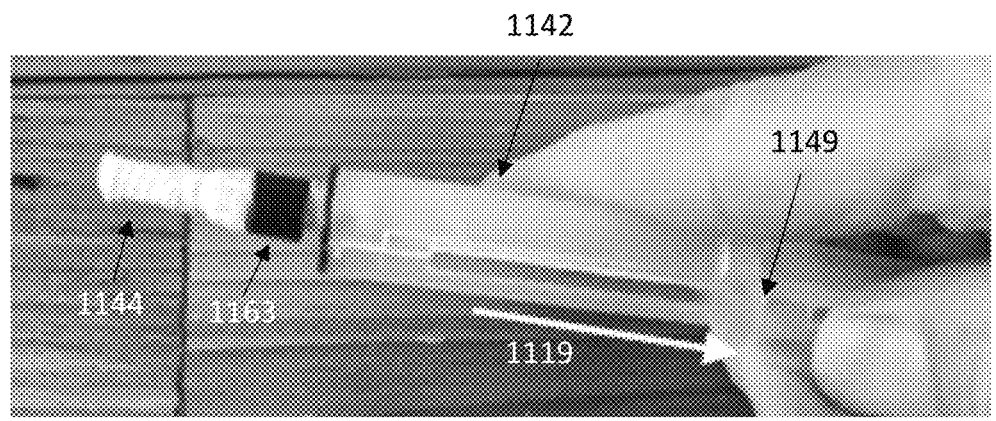
Figure 12C:
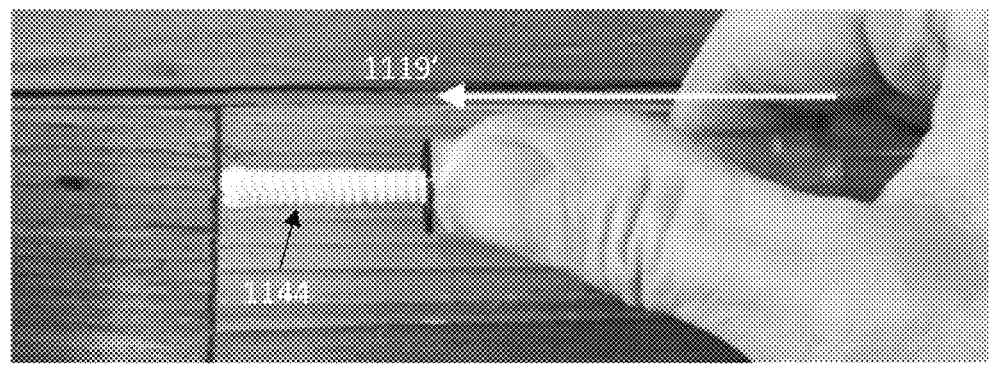

FIGS. 12A-12C illustrate operation of the system, which may be inserted into a body orifice. In FIG. 12A the slider (control 1149) may be slid proximally 1119 when the distal end of the device (e.g., the swab sleeve) is inserted into the body (e.g., into the ear canal). This will roll the inverting conveyor tube which in turn will pull and invert the swab sleeve 1144, drying and removing material from within the body. FIG. 12B shows the control (slider 1149) being moved proximally 1149 to actuate the device, pulling and inverting the swab sleeve 1144 so that the free end (cuff 1163) of the device is drawn distally. Once the draw length of the slider is reached, so that the swab sleeve 1144 may be fully (or partially) inverted, the device may be removed from the body and reset, as illustrated in FIG. 12C. In this example the slider is pushed forward to reverse the rolling motion of the inverting conveyor tube and therefore re-inverting the swab sleeve back to the initial position, as shown. This may remove material collected by the swab sleeve and may reset the swab sleeve if is to be reused; alternatively the swab sleeve assembly may be removed from the swab actuator 1142.

Figure 13:
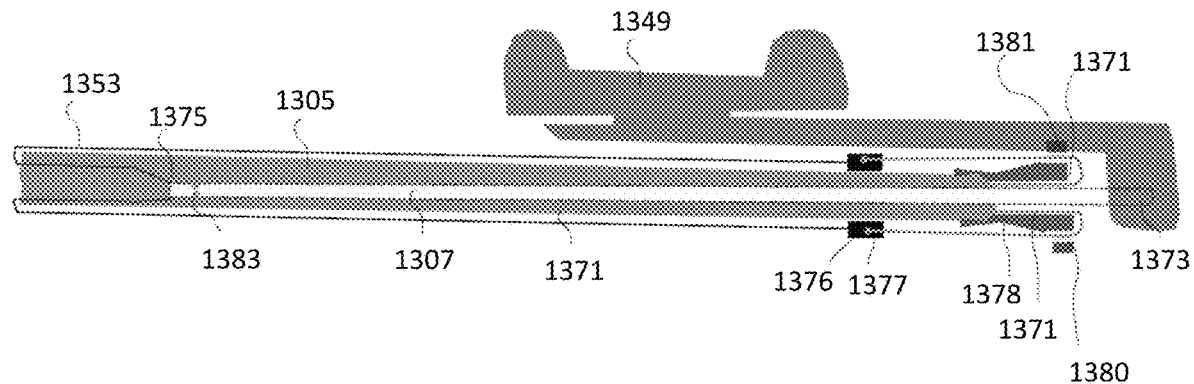
FIG. 13 schematically illustrates a portion of an inverting swab system.
Figure 14:
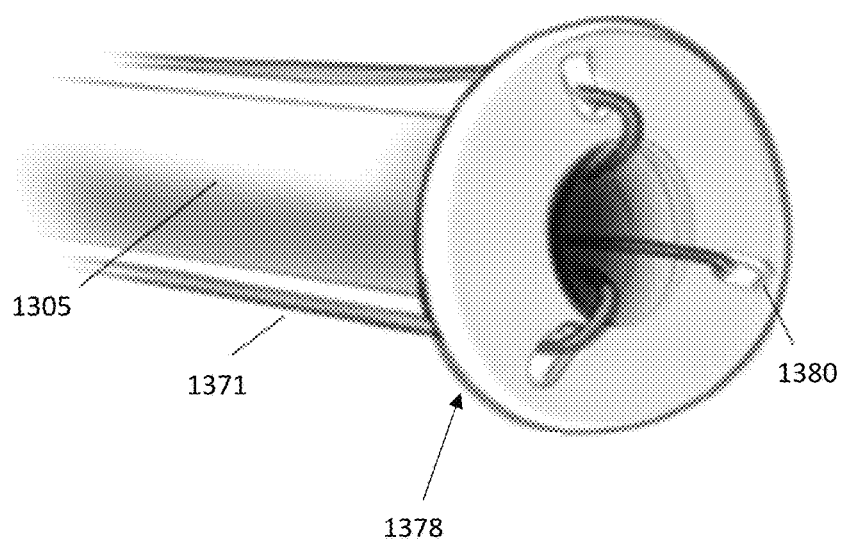
FIG. 14 shows enlarged detail for an elongate tubular shaft of an inverting swab system similar to that partially shown in FIG. 13.
Figure 15:
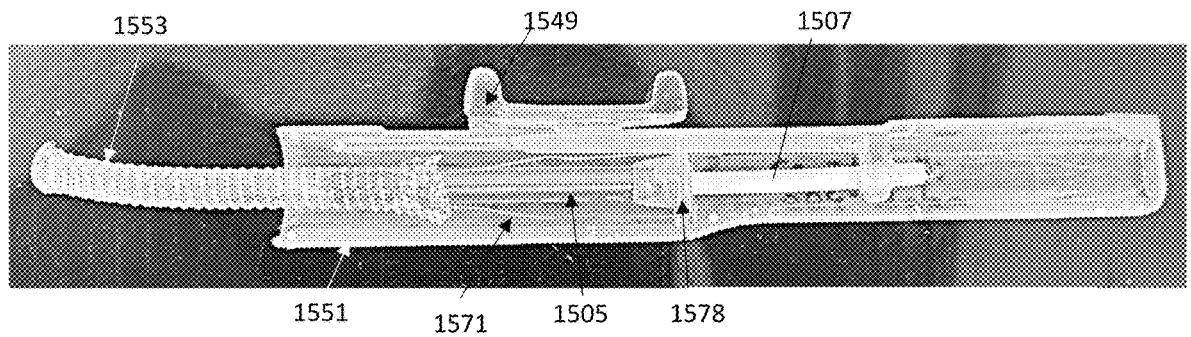
FIG. 15 is a section through an example of an inverting swab system.

FIGS. 13-15 illustrate the operating of the inverting conveyor tube of the swab actuator. The inverting conveyor tube may be configured to engage with the disposable swab sleeve assembly, and may be formed of a material that is particularly well suited to grip or engage with the swab sleeve of the disposable swab sleeve assembly.

In addition, the inverting conveyor tube may be configured so that it can be reciprocated by activation of the control (e.g., slider in the example shown above in FIGS. 9, 10A-10B, 11A-11D and 12A-12C). For example, the inverting conveyor tube may be configured to roll and invert over the elongate tubular shaft as the reciprocating shaft is moved and the swab actuator may include one or more tethers coupling a first end of the inverting conveyor tube to a first end region of the reciprocating shaft of the driver. The second end of the inverting conveyor tube may be coupled to the first end region. This configuration is illustrated in FIGS. 13 and 14. For example, FIG. 13 shows a section through a portion of one example of a swab actuator including the control (slider 1349), driver (e.g., reciprocating shaft 1307), elongate tubular shaft 1305, inverting conveyor tube 1353, and tethers 1371.

In FIG. 13 the slider 1349 is coupled to the proximal end 1373 of the reciprocating shaft 1307. The distal end of the reciprocating shaft is coupled to one end of the inverting conveyor tube at a conveyor tube cuff 1375. The conveyor tube cuff at the first end (e.g., the end coupled to the reciprocating shaft of the driver) may be optional, and instead the inverting conveyor tube cuff may be any attachment interface (similar to the attachment interface for the swab sleeve described in FIGS. 1A-1B and 2). For example, this first end of the inverting conveyor tube may be adhesive and/or mechanically attached to the reciprocating shaft of the driver 1307. The inverting conveyor tube extend over and inverted into an elongate tubular shaft 1307 (e.g., inversion tube). The elongate tubular shaft may be coupled at a proximal end to a base portion of the swab actuator, providing a stable ground reference against which the inverting conveyor tube may roll. In FIG. 13 the proximal end of the elongate tubular shaft 1307 (e.g., inversion tube) is coupled to a flange 1378 that may couple the elongate tubular shaft to the housing of the swab actuator while providing sufficient space to allow reciprocating (back and forth) movement of the driver (e.g., the reciprocating shaft 1307 of the driver). The flange may also provide one or more passages 1380 or channels for passing the tether(s) that conned the ends of the inverting conveyor tube, allowing the tether(s) to move through the flange as the inverting conveyor tube is actuated. The flange may also include space 1381 (e.g., a cut-our region) to allow movement of the control (e.g., slider 1349). This space may be part of a flange interface for the slider, permitting the slider to move back and forth along the housing inside a groove (space) within the flange 1378.

In FIG. 13, the end of the inverting conveyor tube 1353 that is opposite from the end attached to the reciprocating shaft 1307 is coupled to a second conveyor tube cuff 1376 that connects the tether(s) 1371 to the inverting conveyor tube. The tether(s) may connect to the second cuff or directly to the inverting conveyor tube at a proximal tether attachment 1377. The second conveyor tube cuff may also be optional, as the tether(s) may be directly coupled to the second end or end region of the inverting conveyor tube.

The one or more tethers 1371 may be formed of any appropriate material so that they may provide sufficient strength and flexibility to functionally connect the ends of the inverting conveyor tube and allow it to reciprocate as the first end region of the inverting conveyor tube 1353, which is coupled to the reciprocating shaft 1307 of the driver (e.g., at the first optional cuff 1375). In some examples the tethers may couple to the distal end region of the reciprocating shaft of the driver; optionally the tethers may couple directly to the inverting conveyor tube and/or to the first cuff 1375. In FIG. 13, the tether(s) are shown coupled to a distal region of the reciprocating shaft at a distal tether attachment site 1383 that may be one the reciprocating shaft 1307. The second end of the tethers may couple directly or indirectly to the second end of the inverting conveyor tube, e.g., at the second cuff 1376.

FIG. 14 illustrates an enlarged example of a flange 1378 that may be included to provide a channel or passage through the elongate tubular shaft 1305 and allow functional connection of the ends of the tether(s) to the ends of the inverting conveyor tube 1353. The flange is an optional element; alternatively the elongate tubular shaft 1305 may itself include one or more openings or channels for passage of the tether, and may directly or indirectly couple to the rest of the swab actuator. In FIG. 14, the flange 1378 (or flange region of the elongate tubular shaft) is at a distal end region of the elongate tubular shaft 1305 and include openings 1380 for passage of each of the tethers 1371. The openings may be rounded or otherwise configured to prevent damage to the tethers.

FIG. 15 shows an example of a section through a swab actuator, showing the housing enclosing the handle body 1551, inverting conveyor tube 1553, control (slider) 1549, reciprocating shaft of the driver 1507 and a flange 1578 at a distal end of the tubular shaft 1505. Tethers 1571 extend from the first end of the inverting conveyor tube 1553, though the flange 1578 and therefor through the elongate tubular shaft 1505 and adjacent to a portion of the reciprocating shaft of the driver 1507 to couple with either with the proximal region of the reciprocating shaft and/or the second end of the inverting conveyor tube 1553.

Figure 16:
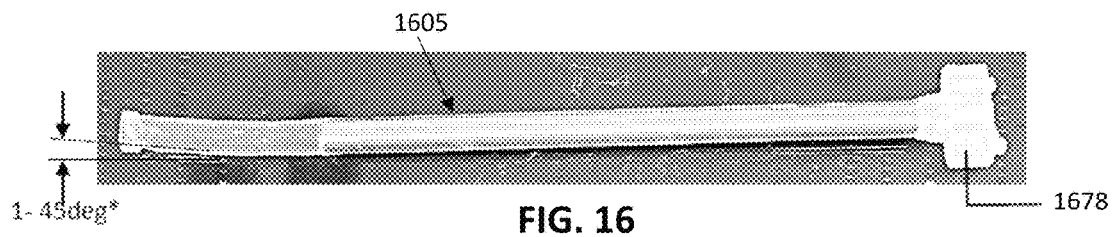
FIG. 16 shows a portion, including the elongate tubular shaft, of an inverting swab system.

FIG. 16 shows an example of a sub-assembly including the elongate tubular shaft 1605 and flange 1678. In this example the elongate tubular shaft ("inversion tube") 1605 is shown curved (e.g., between about 1-45 degrees), at the distal end region. This curvature may enhance the ability of the device to be inserted into body region, such as the ear, having canals that are curved. The elongate tubular shaft shown in FIG. 16 includes a polymeric covering or coating (e.g., PTFE tube) that may reduce friction and may provide for a smoother passage of the inverting conveyor tube. In any of these examples, the elongated tubular shaft can be straight or bent and may have one or more sections of high, medium and/or low stiffness sections along its length, which may help the tube track safely into the patients (potentially curved or bent) target anatomy (e.g., ear canal, nose, etc.). In one example, the distal end region and/or a middle region near may have a lower bending stiffness as compared with the rest of the elongated tubular shaft.

Figures 17A, 17B:
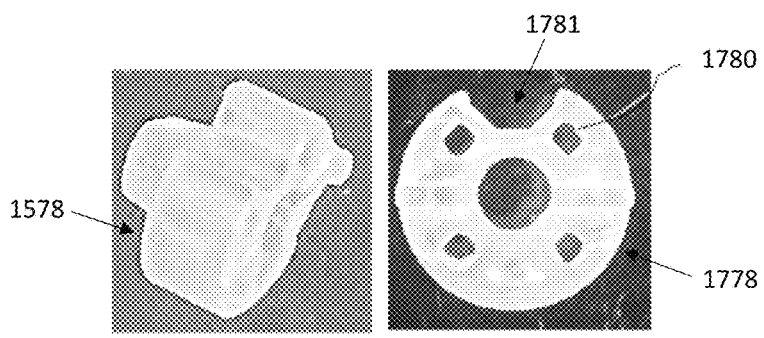
FIGS. 17A-17B illustrate an example of a flange of an elongate tubular shaft for an inverting swab system.

FIGS. 17A and 17B illustrates examples of a flange 1778 including a cut-our region 1781 for passage of the control (e.g., slider) assembly and holes 1780 (which may alternatively be channels) for passage of the tethers. The flange may be secured within the housing of the swab actuator. FIG. 17A shows a side perspective view of the flange and FIG. 17B shows a back view.

Figure 18:
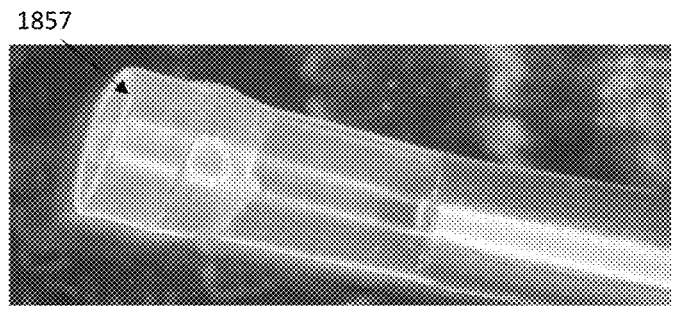
FIG. 18 is another view of a portion of an elongate tubular shaft of an inverting swab system comprising a PTFE tubing over a stainless steel tube.

FIG. 18 illustrates an example of a proximal end of the elongate tubular shaft 1605 shown in FIG. 16, showing that the distal end region of the elongate tubular shaft 1857, formed of the PTFE material has been reinforced (e.g., by flipping it over itself) to create a smooth and supportive surface (e.g., having a larger radius on tip) that the inverting conveyor tube may roll over. In FIGS. 16 and 18 the elongate tubular shaft is formed of a metal material that is covered with an EPTFE material. Other materials may be used, including just a metal material or polymeric material that is sufficiently strong and lubricious. The elongate tubular shaft may be coated with a lubricious material. Alternatively or additionally, a lubricious tubing (e.g., PTFE tubing) can be slid or shrunk onto a metal, e.g., thin wall tubing (such as, but not limited to stainless steel tubing).

Figure 19A:
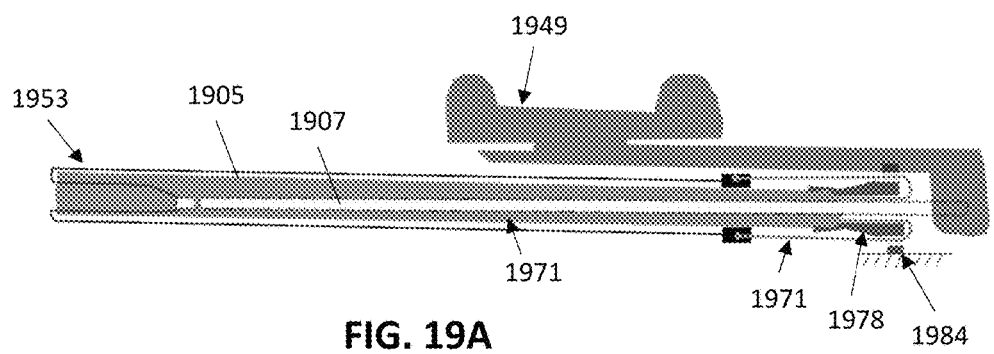
FIGS. 19A-19C schematically illustrate an example of a portion of an inverting swab system.
Figure 19B:
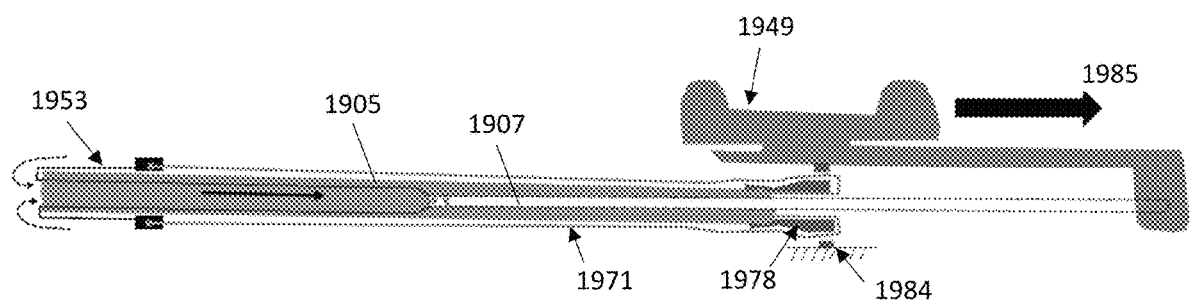
Figure 19C:
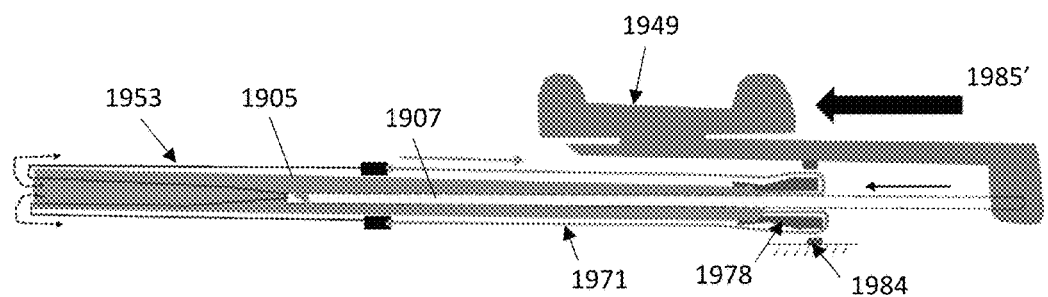

FIGS. 19A-19C illustrate operating of the inverting conveyor tube for a swab actuator such as that shown in FIG. 15. FIGS. 19A-19B show the sub-assembly of FIG. 15, including the inverting conveyor tube 1953, control 1949 (configured as a slider), a drive including a reciprocating shaft 1907, tethers 1971 functionally linking the ends of the inverting conveyor tube, an elongate tubular shaft 1905, and a flange 1978 at the proximal end of the elongate tubular shaft. The flange is schematically shown connected to the reference 'ground' 1984, e.g., the body of the swab actuator. In FIG. 19A the sub-assembly is shown with the inverting conveyor tube in a neutral ("loading") position, with the majority of the inverting conveyor tube extending over the elongate tubular shaft, and the reciprocating shaft of the driver fully extended distally. In FIG. 19B the control (slider 1949) is shown pulled proximally back, arrow 1985, which in turn pulls the reciprocating shaft proximally, and this in turn pulls the first end of the inverting conveyor tube 1953 proximally, inverting the inverting conveyor tube so that it rolls over itself and into the lumen of the elongate tubular shaft 1905. The tethers 1971 attached at the first end of the inverting conveyor tube 1953 are also pulled proximally, while the second end of the tethers are pulled distally. In operation, this may also pull a swab sleeve of an inverting swab sleeve assembly that is coupled to the inverting conveyor tube into the lumen of the elongate tubular shaft 1905 to actuate the device.

FIG. 19C illustrates resetting of the inverting conveyor tube 1953 by pushing the control (slider 1949) distally, as shown by the arrow 1985'. Pushing the slider 1949 distally pushes the driver (e.g., reciprocating shaft 1907) distally. Since the driver is coupled to the first end of the inverting conveyor tube 1953 and to the tethers 1971 coupled to both ends of the inverting conveyor tube 1953, movement of the reciprocating shaft 1907 distally pulls the tethers attached to the second end of the inverting conveyor tube (applying tension to the tethers) which in turn pulls the inverting conveyor tube so that it rolls back over itself and out of the lumen of the elongate tubular shaft 1905. This movement may also re-invert a swab sleeve if one is coupled to the inverting swab sleeve assembly.

Figure 20A:
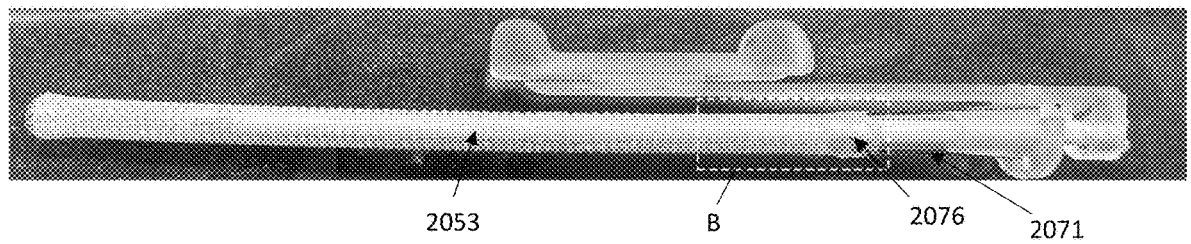
FIGS. 20A-20B illustrate a portion of an inverting conveyor tube of an inverting swab system.
Figure 20B:
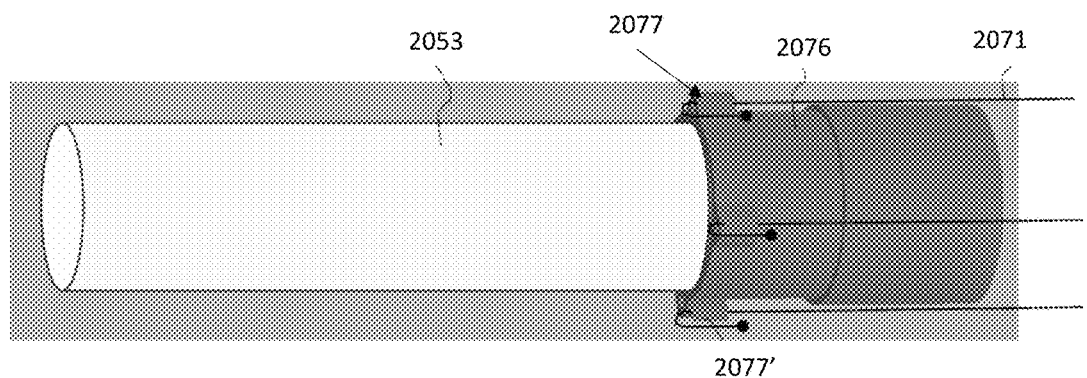

FIGS. 20A and 20B illustrate additional detail on one example of the attachment of a tethers to an inverting conveyor tube in an example device similar to that shown in FIG. 15. In this example a portion (e.g., sub-assembly) of a swab actuator similar to that shown in FIG. 15 is shown, including the inverting conveyor tube 2053 and the second cuff 2076 (also referred to herein as a conveyor tube cuff) through which the tethers 2071 are coupled to the inverting conveyor tube. FIG. 20B shows an enlarged view (of region B) of the sub-assembly shown in FIG. 20A. In FIG. 20B the schematic of the inverting conveyor tube is should connected to the conveyor tube cuff 2076. A plurality of tethers 2071 are connected to the conveyor tube cuff. In this example, the conveyor tube cuff includes attachments, shown as openings or channels 2077, 2077' in the conveyor tube cuff through which the tethers may be attached (e.g., tied, bonded, crimped, etc.). The tethers may be attached at equally-spaced regions around the perimeter of the cuff. The cuff 2076 may be configured to slide over the elongate tubular shaft.

Figure 21A:
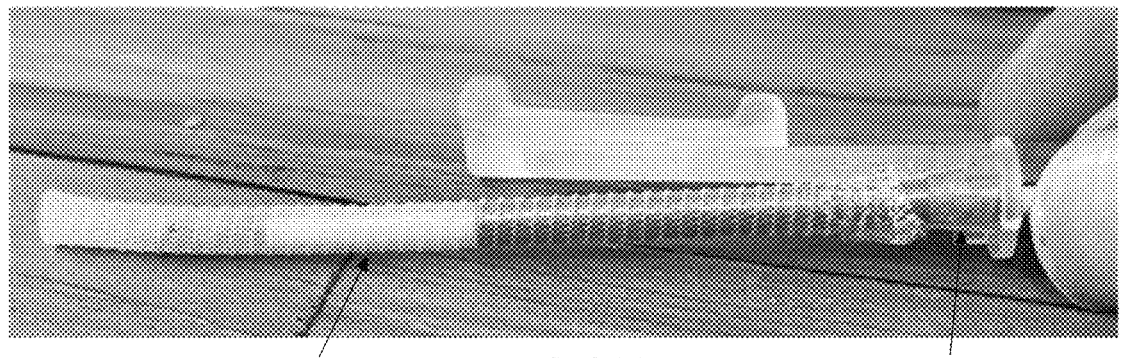
FIGS. 21A-21C illustrate operation of a portion of an inverting swab system.
Figure 21B:
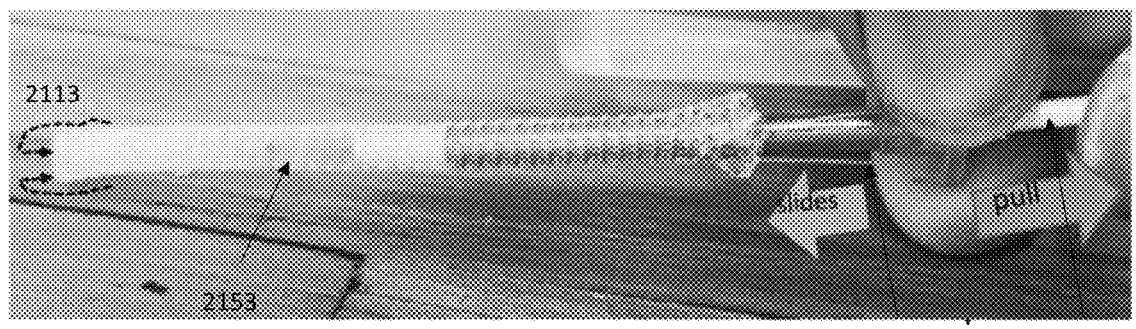
Figure 21C:
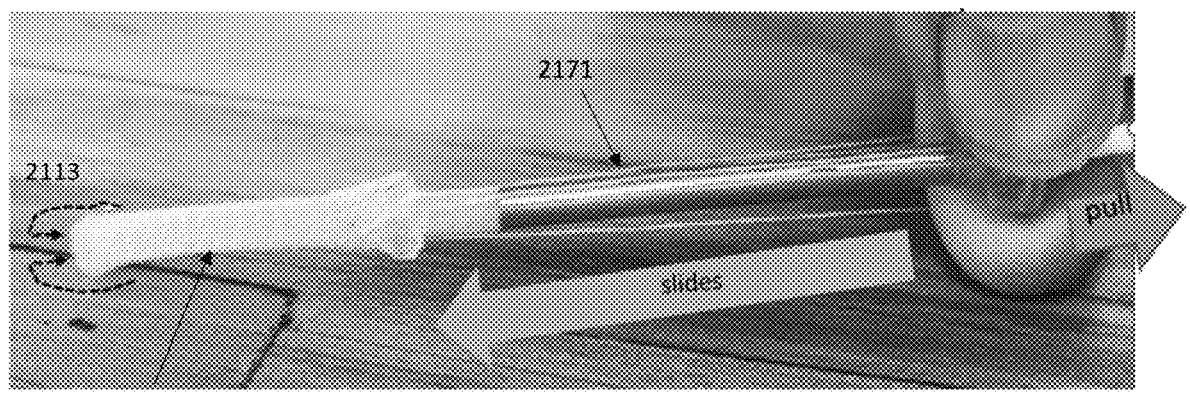

FIGS. 21A-21C illustrate one example of the operation of a reciprocating inverting conveyor tube. In FIG. 21A the inverting conveyor tube is coupled to tethers 2171 at either end of the inverting conveyor tube, as described above. In the neutral position (FIG. 21A), the inverting conveyor tube 2153 is coupled to the tethers 2171 and pulling the driver (e.g., the reciprocating shaft 2107 of the driver) proximally causes the inverting conveyor tube to invert 2113 over the distal end of the device, e.g., the distal end of the elongate tubular shaft, as shown in FIGS. 21B and 21C. Because the tethers 2171 are attached to the inverting conveyor tube and to the reciprocating shaft of the driver, the tube may be restored to the original position by moving the reciprocating shaft in the opposite direction.

Note that in this first example the inverting conveyor tube is configured to be coupled with a disposable swab sleeve assembly that is used to dry and remove material, in some examples the inverting conveyor tube may be configured for use as an inverting swab sleeve that can itself absorb and/or remove material, without the need for an additional disposable swab sleeve assembly. In these cases the swab actuator may be configured for limited use, or may be configured to be reused. In some examples the inverting conveyor tube (e.g., operating as the swab sleeve) may be washed and/or dried between uses.

Figure 22:
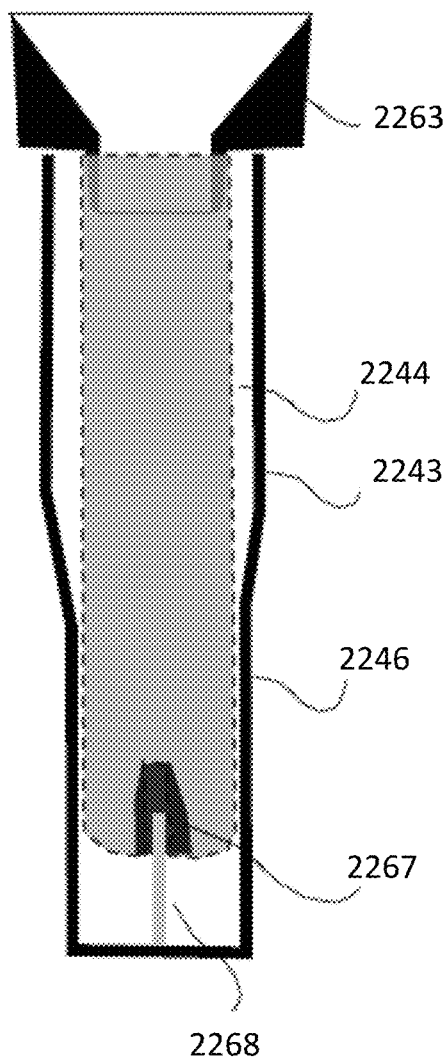
FIG. 22 schematically illustrates an example of an inverting swab sleeve assembly.

In variations in which an inverting swab sleeve assembly is used with the reusable swab actuator, the inverting swab sleeve may be coupled to a swab actuator. The inverting swab sleeve assembly may be adapted so that it may be reliably and easily coupled to the swab actuator. For example, the inverting swab sleeve assembly may be configured to couple to the inverting conveyor tube of the swab actuator. FIG. 22 illustrates one example of an inverting swab sleeve assembly that is configured to more easily engage with an inverting conveyor tube of the swab actuator, such as the swab actuator shown schematically in FIG. 23. In this example the inverting swab sleeve assembly includes a sleeve cuff 2263 that is attached to one end (the outer end) of the inverting swab sleeve 2244. The second end of the inverting swab sleeve (at the distal end) is connected to an engagement cap 2261 that is configured to engage with the inverting conveyer tube of a swab actuator. The inverting swab sleeve assembly may be held within a cover (e.g., loading cover or loading tube) 2243. The cover 2243 shown in this example is tapered 2246. The loading tube may also include an (optional) centering pin 2268 that may hold the engagement cap 2261 centered relative to the inverting conveyor tube of the swab actuator.

Figure 23:
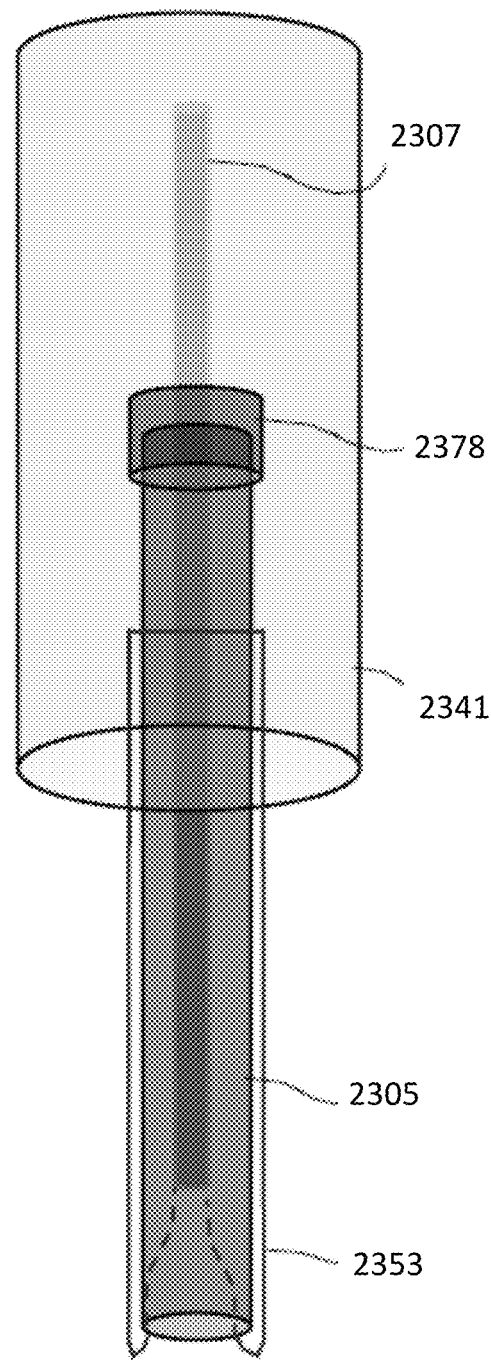
FIG. 23 schematically illustrates an example of a distal end of a swab actuator that may be used with an inverting swab sleeve assembly as shown in FIG. 22.

FIG. 23 schematically illustrates an example of a distal end portion of swab actuator that may engage with an inverting swab sleeve assembly similar to that shown in FIG. 22. The swab actuator includes an inverting conveyor tube 2353 that is configured to reciprocally invert and un-invert around an inversion tube (e.g., an elongate tubular shaft) 2305 by pulling a reciprocating shaft 2307 of a driver. The inversion tube may include a flange 2378 at the proximal end that may provide openings or channels for one or more tethers (not shown) coupled to the inverting conveyor tube. The region of the swab actuator extending proximally from the proximal half of the inverting swab sleeve may be at least partially covered by a housing 2341 that may be part of the handle housing of the swab actuator.

FIGS. 24A-24C illustrate engagement of the inverting swab sleeve assembly shown in FIG. 22 with the swab actuator example shown in FIG. 23. In this example the distal end of the inverting conveyor tube is inserted 2491 through the cuff 2463 of the inverting swab sleeve assembly, and into the lumen of the inverting swab sleeve 2444. FIG. 24B show an intermediate position, prior to fully engaging with the inverting swab sleeve assembly. In FIG. 24C the inverting conveyor tube 2453 has been inserted 2491' fully into the inverting swab sleeve 2444 so that the engagement cap 2467 of the inverting swab sleeve assembly is at least partially inserted into the lumen of the inverting conveyor tube 2453, as shown. The inverting swab sleeve may be fully engaged by actuating the inverting conveyor tube slightly so that the inverting conveyor tube grabs the engagement cap 2467 and draws it fully into the lumen of the inverting conveyor tube, within the elongate tubular shaft of the swab actuator.

FIG. 25 schematically illustrates an example of an inverting swab sleeve that is engaged with a swab actuator. In this example, the swab actuator includes an outer elongate tubular shaft 2505 (including flange 2578) over which an inverting conveyor tube 2567 extends; the inverting conveyor tube is coupled to an inner driver including a reciprocating shaft 2507 to reciprocate the inverting conveyor tube by actuating a control (not shown). An inverting swab sleeve 2544 is coupled to the inverting conveyor tube 2567 of the swab actuator so that the inverting conveyor tube is inserted into the lumen of the inverting swab sleeve 2544. The inverting conveyor tube 2563 has grabbed the engagement cap 2567 at one end of the inverting swab sleeve 2544.

In general, the inverting swab sleeve may be configured to securely, but removably, engage with the swab actuator. In some examples, one or more friction connections between the inverting swab sleeve and the swab actuator may be present. In the example system shown in FIG. 25, two friction points help secure the inverting swab sleeve to the swab actuator. A first friction interface is present between the inner diameter of the cuff 2563 of the inverting swab sleeve and the outer diameter of the inverting conveyor tube 2567. The second friction point is between the engagement cap 2567 and the inner diameter of the inverting conveyor tube 2567. In general, when loading the inverting swab sleeve 2544 onto the conveyor tube 2567, the first and second friction points may have a sufficiently low friction allow relatively easy and repeatable loading/sliding. The engagement cap 2567 on the disposable sleeve may be aligned with the center of the inverting tube to enable reliable and repeatable insertion; in some examples an aligner (e.g., centering pin, centering guide, alignment guide, etc.) may be present on the engagement cap, inverting swab sleeve assembly, and/or cover. Thus, alignment of the nipple to the tip of the inverting tube can be achieved through a variety of structures. In some examples, the cover (e.g., loading tube) may include a tapered inner diameter (as shown in FIG. 22) and/or may include a centering pin that is attached to the distal end of the loading tube.

When operating the apparatus, e.g., by operating the control to invert the inverting conveyor tube and therefore the inverting swab sleeve, the apparatus may be configured so that there is sufficient friction to ensure that the disposable inverting swab sleeve is in tension during pulling, and also when pushing of the control (e.g., in some examples a slider) to roll the inverting conveyor tube in or out of the elongate tubular shaft, particularly when the removable inverting swab sleeve is contacting a body surface (e.g., inside of the ear, nose or other part of the body) during use. If the contact friction between the cuff and the inverting conveyor tube is too low, the cuff may work its way down the conveyor tube during pull/push cycles. If the friction between the inverting conveyor tube and the engagement cap is not sufficient, the engagement cap may be ejected from the end of the inverting conveyor tube during operation, or may not be pulled inside the inverting conveyor tube during the pull cycle.

Thus, the methods and apparatuses described herein may tune the friction between the cuff and the inverting conveyor tube, e.g., by adjusting the inner diameter (ID) of the cuff and/or the outer diameter of the inverting conveyor tube. Optionally, the material forming the inverting conveyor tube, the cuff and/or the inverting swab sleeve can be made of compressible or elastic material. Example of compressible or elastic materials that may be used include foam, santoprene, nitrile, neoprene, pvcpaint, pvcfoam, an open cell foam, and/or a closed cell foam. Alternately the ID/OD of the two interfacing parts (e.g., the inverting conveyor tube and/or the cuff or inverting swab sleeve can be the same similar; in some examples one of the interfacing materials is tacky (e.g., silicone, urethane) to adjust the friction between the two.

The friction between the engagement cap and the inverting conveyor tube can be adjusted or set by determining the ID of the inverting conveyor tube so that it is slightly smaller than the OD of the engagement cap. Optionally, the inverting conveyor tube material, inverting tube and/or engagement cap can be compressed of compressible or elastic material. Example of compressible or elastic materials that may be used may include (but are not limited to) foam, santoprene, nitrile, neoprene, polyvinyl chloride (PVC, e.g., foam, pain, etc.), open cell foams, and/or closed cell foams. Alternately the ID/OD of the two interfacing parts can be the same or similar, but another portion of the interfacing materials may be formed of a material that is 'tacky' (e.g., silicone, urethane, etc.) to achieve some friction.

FIG. 26 illustrates examples of engagement caps that may be used with any of the systems (e.g., any of the inverting swab sleeve assemblies) described herein. FIG. 26 schematically illustrates an example of distal end of an inverting swab sleeve including an engagement cap. In this example the inverting swab sleeve 2644 is a cellulose material (e.g., cellulose sleeve); at one end of the inverting swab sleeve the sleeve material is coupled to an engagement cap 2667. In some example, the one end of the inverting swab sleeve may be formed into a plug or other structure that is bonded within the engagement cap 2667. For example, the end of the inverting swab sleeve may be glued or otherwise adhesively or mechanically coupled to the engagement cap.

FIGS. 27A-27C illustrate examples of engagement caps having different cross-sectional shapes. FIG. 27A shows an example of an engagement cap having a generally bullet-shaped cross-section in which the lateral walls of the engagement cap are uniform in thickness. FIG. 27B shows another example of an engagement cap having a bullet (e.g., tapered) shape that includes non-uniform lateral wall thickness. In this example the non-uniform wall thickness may make some region more easily compressible than other regions. FIG. 27C shows another example of an engagement cap having a bullet (e.g., tapered) shape similar to that shown in FIG. 27B but with different cross-sectional thickness along the length.

FIGS. 28A-28C and 29A-29G show examples of alternative examples of engagement caps. For example, FIG. 28A shows an engagement cap that may be formed by setting the hardness of different regions of the distal end region of the inverting swab sleeve. In this example the proximal region 2826 is somewhat spongy and soft compared with the more distal region 2827 that is harder. FIG. 28B shows an example in which a capture region 2829 (e.g., O-ring, shown in this example as a latex O-ring) is coupled with the distal end of the inverting swab sleeve. The distal end may also be harder 2827 than the more proximal region. FIG. 28C shows another example in which a foam material 2833 is attached at the proximal end of the engagement cap. In this example the foam material flares out, which may help center the engagement cap.

In any of the engagement caps described, the outer surface of the engagement cap may be shaped or textured. For example, FIGS. 29A-29D show engagement caps having different surface patterns/textures. FIGS. 29A-29B include dimples, including small dimples (FIG. 29A) and large dimples (FIG. 29B). FIGS. 29C-29D show examples having ridges, including small (FIG. 29C) and large (FIG. 29D) ridges. FIGS. 29E and 29F shows engagement caps having smooth outer surfaces, that include regions of different outer diameter (e.g., narrower distal and large proximal diameters. FIG. 29G shows an example of an engagement cap similar to that shown in FIG. 29F coupled (e.g., glued) to an inverting swab sleeve.

Figure 30A:
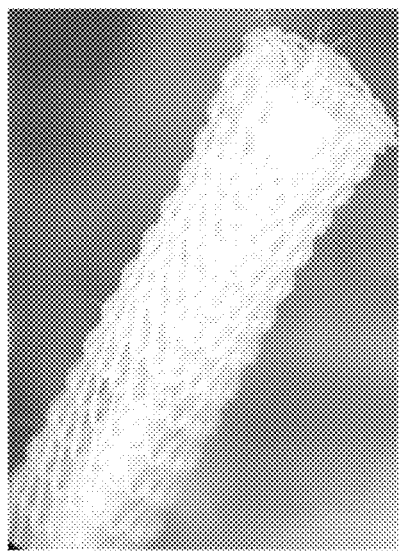
FIGS. 30A-30E illustrate examples of inverting conveyor tubes for use with a swab actuator of an inverting swab system.
Figure 30B:
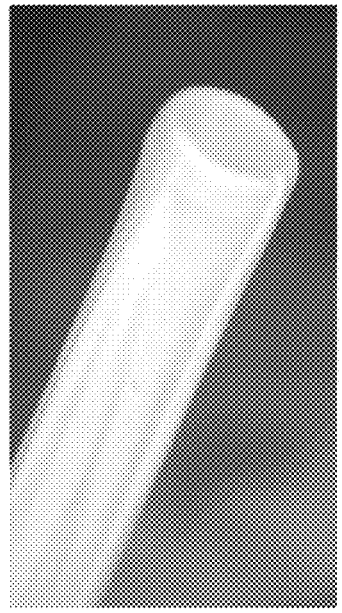
Figure 30C:
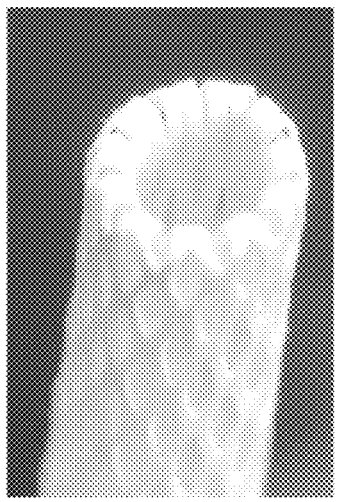
Figure 30D:
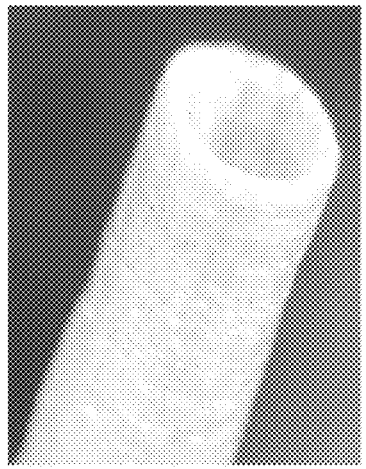
Figure 30E:
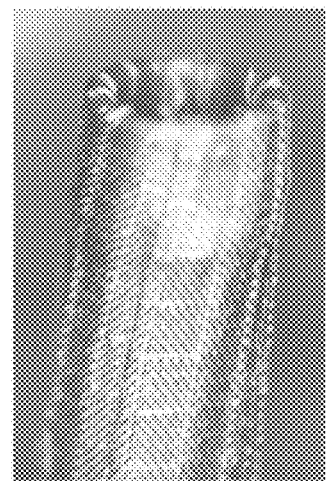

In addition to the texture and material forming the engagement cap, any of the inverting conveyor tubes described herein may be configured to have a desired grip (e.g., friction) property for both engaging with the engagement cap (when included) and/or for engaging with the inverting swab sleeve. For example, FIGS. 30A-30E illustrate examples of inverting swab sleeves as described herein. In FIG. 30A the inverting swab sleeve is formed of a nylon filament that is knit into a tube (e.g., with 20 needles using 0.003" nylon). FIG. 30B shows an inverting swab sleeve formed from expanded polytetrafluoroethylene (ePTFE) into a tube (using 0.004" diameter ePTFE). FIG. 30C shows an example of a laser-cut ePTFE tube (using 0.006" CO2 laser cut ePTFE). FIG. 30D shows an example of a 0.001" dynema film fused to form a tube. FIG. 30E shows an example of a 0.001" nylon membrane film fused to form a tube.

As mentioned, in general the inverting conveyor tube may be formed in a similar manner to the inverting swab sleeve (and vice versa). For example, the inverting conveyor tube may be formed as a tubular knit, a tubular braid, a thin film material that is formed into a tube (e.g., including rolling from a flat sheet and sealing or forming directly as a tube), and/or as thin flexible extruded material (e.g., ePTFE, santoprene, other rubbers, etc.). For example, the inverting conveyor tube may be formed of a tubular materials that can be subsequently laser cut and/or die punched to form a flexible structure that will roll around an elongate tubular member as described. In some cases the inverting conveyor tube may be formed as one or more ribbons having a flat or round cross section that is pulled into at tubular shape.

Figure 31A:
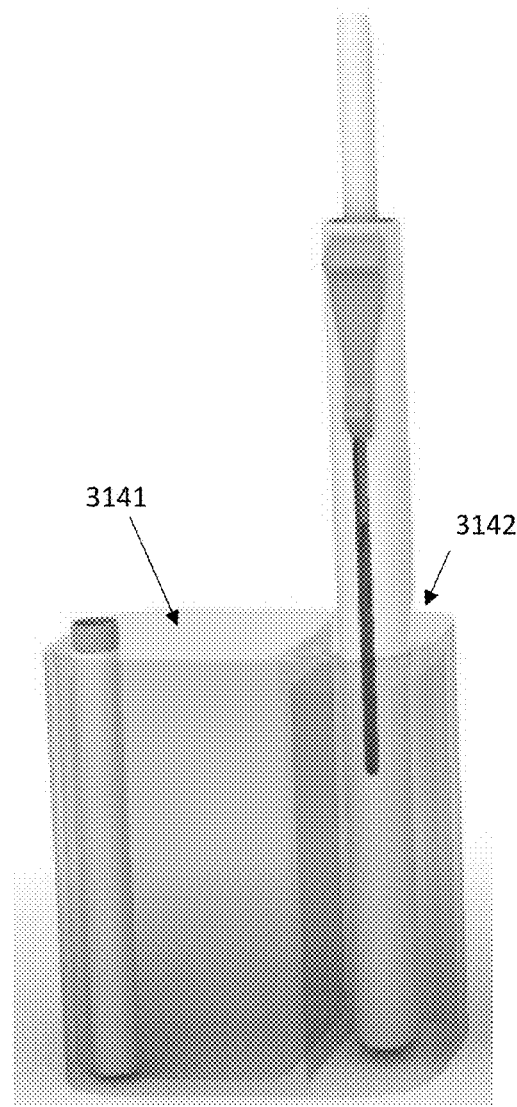
FIGS. 31A-31B schematically illustrate examples of dispensing systems for inverting swab systems.
Figure 31B:
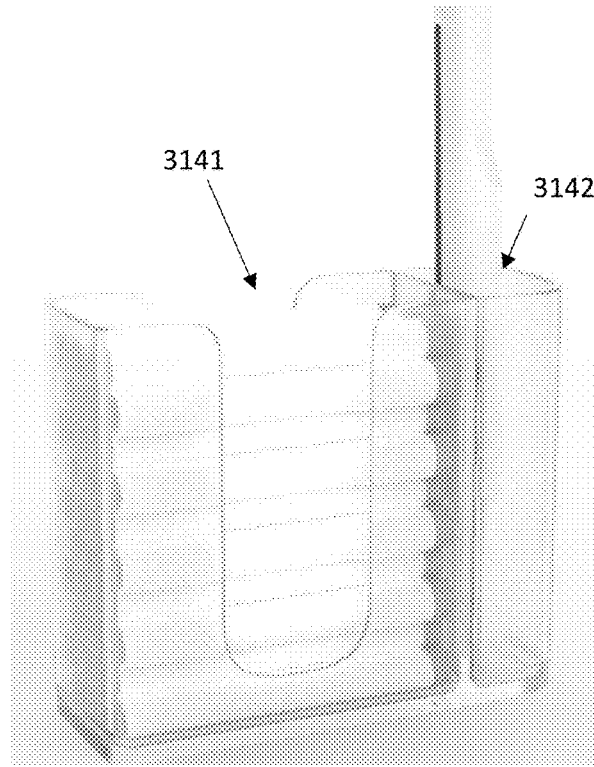

In general, the inverting conveyor tube may be formed from a variety of different structures and materials, such as a flat woven, flat laminated, flat braided and/or flat knitted structure that is rolled and sewn/fused into a tubular shape by a tubular braid or knit structure. Materials used in the woven, laminated or knitted structure can include one or more materials, for example: cellulose fibers (e.g., Rayon, Lyocell, Tencel); cellulose yarn (e.g., 50-500 denier); cotton (e.g., bulk cotton, cotton yarns, cotton plied yarns, including 2-10 yarn filaments twisted together, and/or yarns having sizes between 2-90 Ne). The inverting conveyor tube may be formed of a monofilament and/or multifilament plastics like PET, nylon, Poly propylene. In some examples the inverting conveyor tube may be formed of a metallic material (e.g., Nitinol, stainless steel, etc.). The size may range from 0.0005" to 0.010" diameter. In general, the materials may be hydrophilic materials, e.g., cellulose nanofibril hydrogels. In some cases the material may formed of fibers that can be first plied or twisted, e.g., around a nylon or PET monofilament. Dispending Also described herein are dispensing systems for inverting swab systems. In general, a dispensing system may include a chamber for holding one or more inverting swab sleeve assemblies and a chamber or holder for holding the swab actuator. Any of these dispensing systems may also include one or more disposal (or recycling) chambers for capturing used inverting swab sleeve assemblies. FIGS. 31A-31B shows a first example including a first chamber 3141 for holding inverting swab sleeve assemblies and a second chamber for holding the swab actuator 3142. FIG. 31B shows another example of a dispensing system.

Figure 32A:
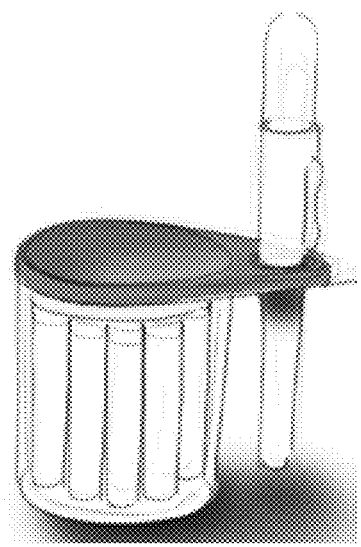
FIGS. 32A-32C schematically illustrate examples of dispensing systems for inverting swab systems.
Figure 32B:
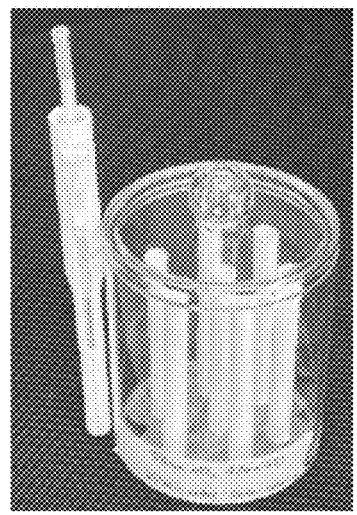
Figure 32C:
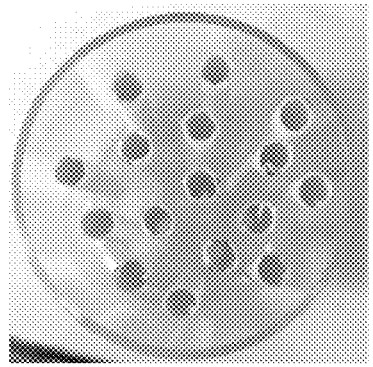
Figure 33A:
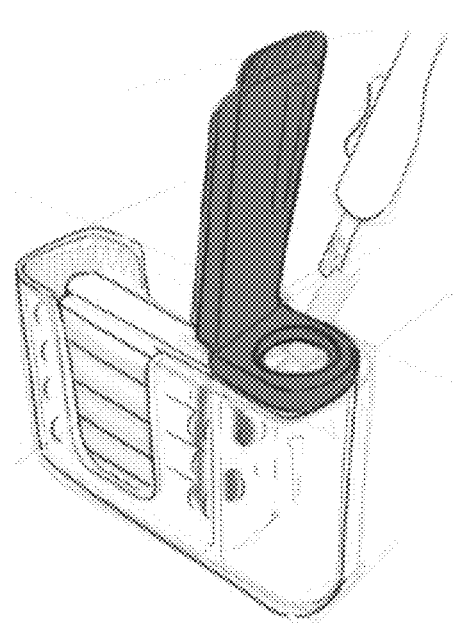
FIGS. 33A-33D schematically illustrate examples of dispensing systems for inverting swab systems.
Figure 33B:
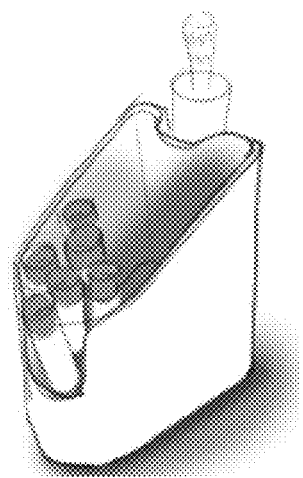
Figure 33C:
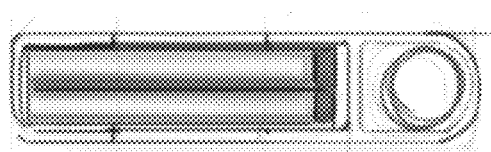
Figure 33D:
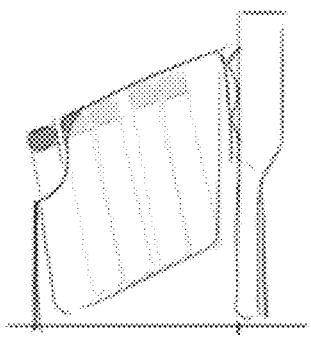

FIGS. 32A-32C illustrate examples of dispensing systems including a chamber for holding inverting swab sleeve assemblies and a holder (e.g., mount) for holding the swab actuator that may be used with the inverting swab sleeve assemblies. In any of these examples the chamber may be configured to hold the inverting swab sleeve assembly so that the swab actuator can easily engage with the inverting swab sleeve assembly. For example, the dispensing system may secure the inverting swab sleeve assembly in a stable position with the opening into the lumen of the inverting swab sleeve exposed for insertion of the swab actuator. For example, in some cases, the dispensing system may be configured for loading tubes to press fit into a bottom tray to align the sleeve vertically. A reusable handle may be inserted into the loading tube in order to load the inverting swab sleeve; the loading tube may stay at the bottom of bin after grabbing the inverting swab sleeve with the swab actuator.

FIGS. 33A-33D schematically illustrate another example of a dispensing system. In this example, the system includes a first chamber for holding the inverting swab sleeve assemblies and a holder or chamber for holding either the used inverting swab sleeve (FIG. 33A) or for holding the swab actuator (FIGS. 33A-33D).

Figure 34:
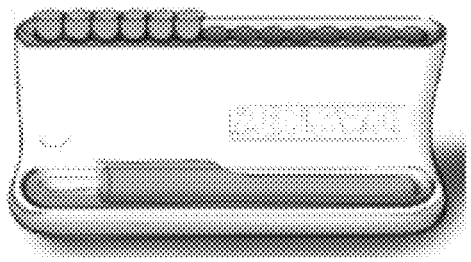
FIG. 34 schematically illustrates an examples of a dispensing system for an inverting swab system.
Figure 35:
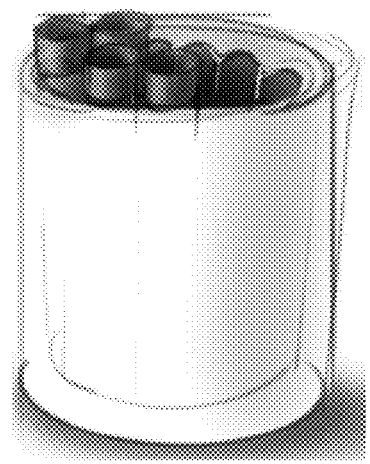
FIG. 35 schematically illustrates an example of a dispensing system for an inverting swab system.

FIG. 34 shows another example of a dispensing system including a tray for holding the swab actuator and loading chamber for holding (and aligning) the inverting swab sleeve assemblies in an orientation that makes them easy to load onto the swab actuator (e.g., with the cuff facing up, exposing the lumen for insertion of the swab actuator. FIG. 35 shows another example of a dispensing system including a loading chamber that is configured to allow easy loading of the inverting swab sleeve.

Controls

In some examples the control for operating the driver to reciprocate the reciprocating shaft relative to the elongate tubular shaft to roll and invert the inverting conveyer tube (and/or the inverting swab sleeve) may be a slider, as shown above. Other control may be used. For example, FIGS. 36A-36D illustrate an example in which the control is configured as a roller wheel that may be operated similarly to the slider. FIG. 36A shows a perspective view of the swab actuator including controller 3649 that may be rolled to invert/re-invert the inverting conveyor tube 3653, as illustrated in FIG. 36B. FIGS. 36C and 36D show sections through the device of FIG. 36A, which is similar to the variation shown in FIGS. 9 and 10A-10B described above, except that the controller (roller) may engage with a tread sub-system to drive the driver (e.g., the reciprocating shaft) distally or proximally by converting the rotational movement of the roller into an in/out linear movement of the reciprocating shaft. Thus, this variation includes a mechanical linear actuator drive reciprocating movement of the reciprocating shaft. In this example one or more pulleys may be used to transform the rotational movement into linear movement.

FIGS. 37A-37D illustrate operation of an apparatus similar to that shown in FIGS. 36A-36D including a roller that may drive movement of the inverting conveyor tube. In this example, the inverting swab sleeve 3701 is partially ingested by rolling the inverting conveyor tube 3753 (FIGS. 37B-37C) and the cuff on the end of the inverting swab sleeve is snapped onto the device (as shown in FIG. 37C) so that the device may loaded and primed for use (FIG. 37D), e.g., by rolling the control to extend the inverting swab sleeve to the start (initial) position.

Figure 38A:
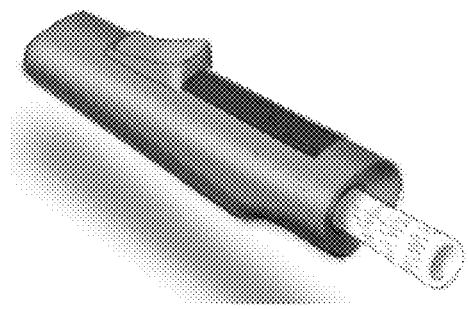
FIGS. 38A-38C show another example of an inverting swab system.
Figure 38B:
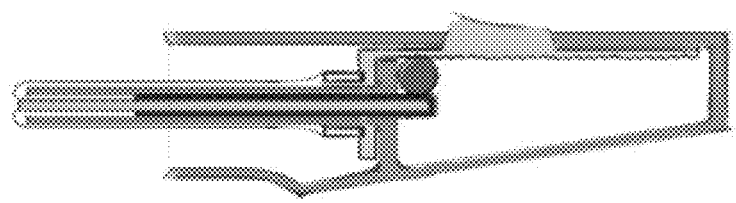
Figure 38C:
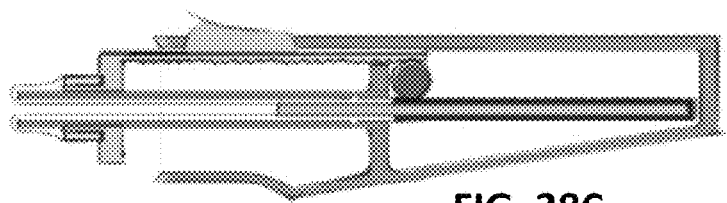
Figure 40A:
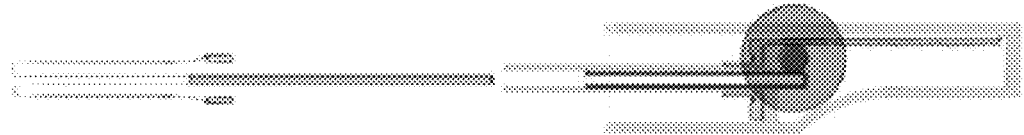
FIGS. 40A-40D illustrate one example of operation of an inverting swab system similar to that shown in FIGS. 38A-38C and 39.
Figure 40B:
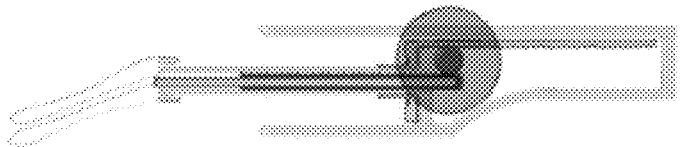
Figure 39:
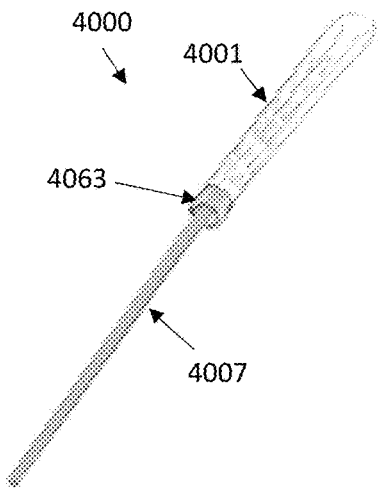
FIG. 39 illustrates an example of an inverting swab sleeve assembly including a reciprocating shaft integrated therewith.
Figure 40C:
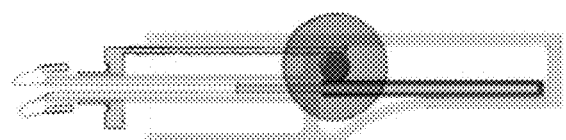

FIGS. 38A-38C, 39 and 40A-40D illustrate another example of an inverting swab system as described herein. In this example, the inverting swab sleeve assembly is configured to include a portion of the reciprocating shaft that is included as part of the swab actuator in other examples. For example, FIG. 40 shows the example of the inverting swab sleeve 4000 in which the inverting swab sleeve 4001 is connected at one end to a cuff 4063 and at the other end to a reciprocating shaft 4007. FIGS. 38A-38C illustrate examples of swab actuators that may be used with these inverting swab sleeve assemblies. In this example, the driver includes a puller that engages with the reciprocating shaft of the inverting swab sleeve. The driver may clamp onto the reciprocating shaft and the controller may include a slider that translates proximal movement of the control into distal movement of the clamp and therefore the reciprocating shaft, as illustrated between FIGS. 38B and 38C. With the clamp region fully extended, it may open to receive the reciprocating shaft, as shown in FIG. 38B. The device may then be loaded into the swab actuator. The outer shaft may pull and invert the swab over the outer tube shaft, a as shown in FIG. 38C. FIG. 40A illustrates loading of the inverting swab sleeve assembly onto the swab actuator.

Figure 40D:
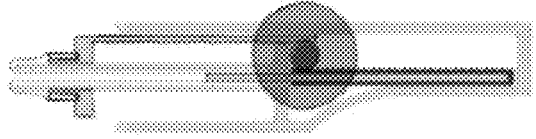

In some examples the driver includes a conveyor tube and inverting tube/shaft that is engaged with the swab sleeve and pulls it into the convey belt shaft (e.g., inverting the tube). In the example shown in FIGS. 38A-38C, 39 and 40A-40D, the driver include the rack and pinon mechanism that translations movement of the control (e.g., slider, roller, etc.) into linear movement of the clamp that grips to the reciprocating shaft of the inverting swab sleeve assembly and pulls on the reciprocating shaft attached to the inverting swab sleeve to invert the swab sleeve. In this example, the cuff 4063 may be manually attached to the swab actuator when loading the device, as shown in FIG. 40D.

Figure 41A:
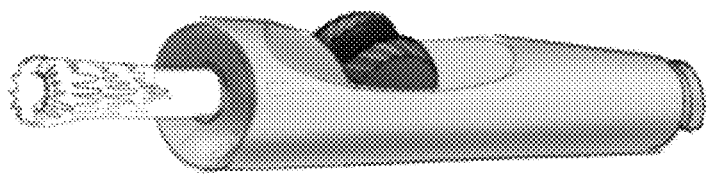
FIGS. 41A-41C illustrate an example of a dispensing system for an inverting swab system.
Figure 41B:
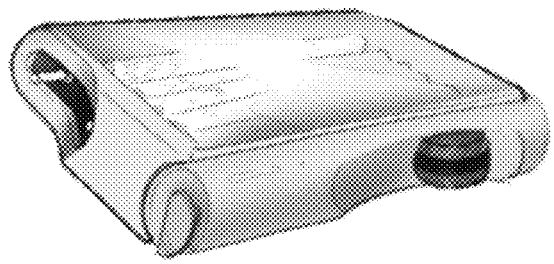
Figure 41C:
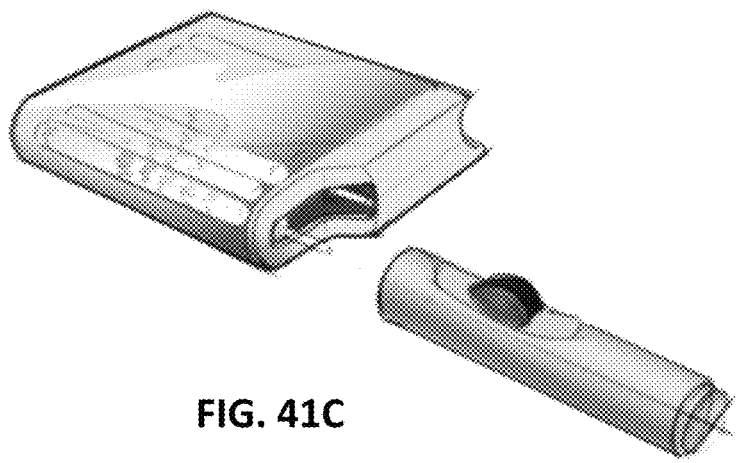

FIGS. 41A-41C illustrate examples of dispensing systems for use with an apparatus as shown in FIGS. 38A-38C, 39 and 40A-40D. The dispensing system include an attachment for coupling to the swab actuator and a chamber for holding the inverting swab sleeve assemblies with the reciprocating shafts exposed for loading into the swab actuator.

Figure 42A:
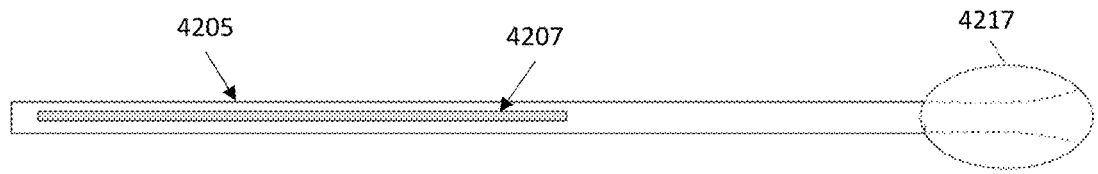
FIGS. 42A-42B schematically illustrate an example of an inverting swab apparatus.
Figure 42B:
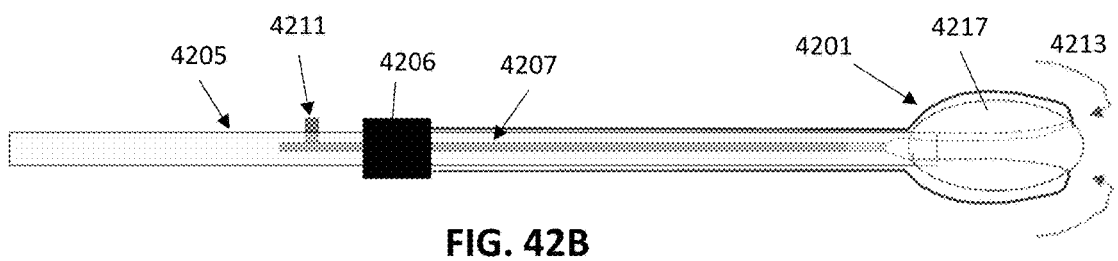

FIGS. 42A-42B, 43 and 44A-B4 illustrate another example of an inverting swab apparatus that may be operated with a single hand. In this example, the entire apparatus may be configured as a disposable or limited-use apparatus in a single, integrated device. For example, FIG. 42A shows a top view of the device of FIG. 42B (the inverting swab sleeve and control are not shown in FIG. 42A). In this example, the device includes an elongate tubular shaft 4205 and an inverting swab sleeve 4201 that is connected at one end (the outer end) to a cuff 4206 and at the other end to a driver (e.g., reciprocating shaft 4207). The drive is connected to or includes a finger control 4211. The finger control extends proud of the elongate tubular shaft in this example. An optional bulb region 4217 is included at the distal end (and/or is part of the distal end) of the elongate tubular shaft. The device may be actuated by sliding the controller proximally to pull the inverting swab sleeve into the elongate tubular shaft so that it rolls 4213 over and inverted into the lumen of the elongate tubular shaft, as illustrated in FIG. 42B.

Figure 43:
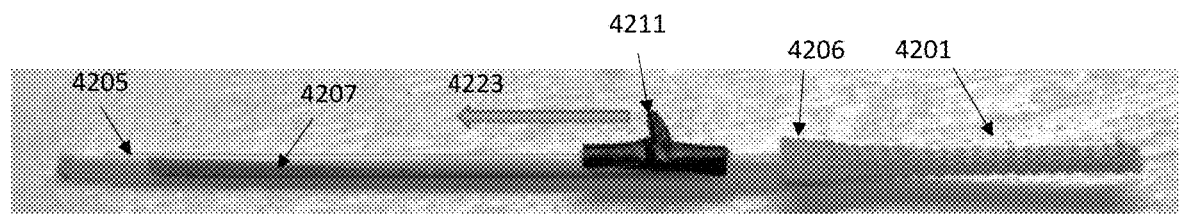
FIG. 43 shows an example of an inverting swab apparatus similar to that shown in FIGS. 42A-42B.
Figure 44A:
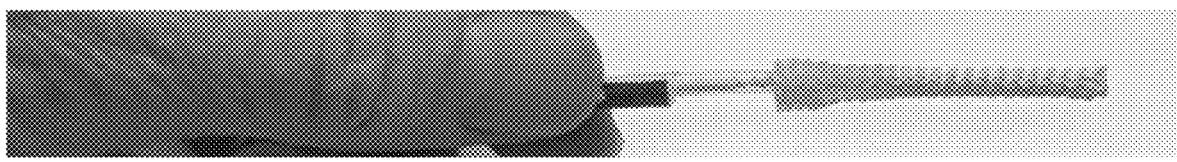
FIGS. 44A-44B illustrate operation of an example of an inverting swab apparatus.
Figure 44B:
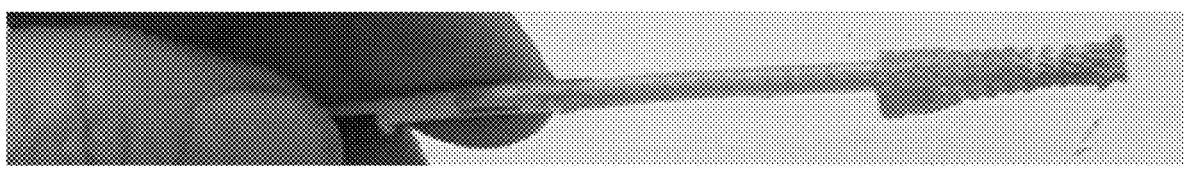

FIG. 43 shows another example of the device of FIGS. 42A-42B including the finger control 4211 (configured as a slider in this example). Sliding the control proximally 4223 rolls the inverting swab sleeve 4201 over the distal end of the elongate tubular shaft 4205 by pulling the reciprocating shaft 4207 of the driver proximally. This is illustrated in FIGS. 44A, showing the device prior to actuation, and FIG. 44B, after partially actuated.

Figure 45:
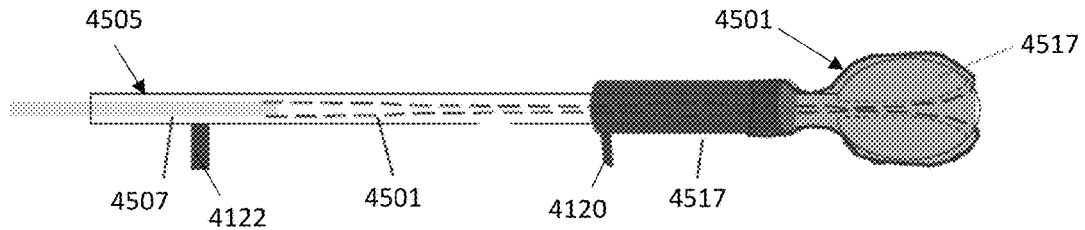
FIG. 45 illustrates an example of an inverting swab apparatus.
Figure 46A:
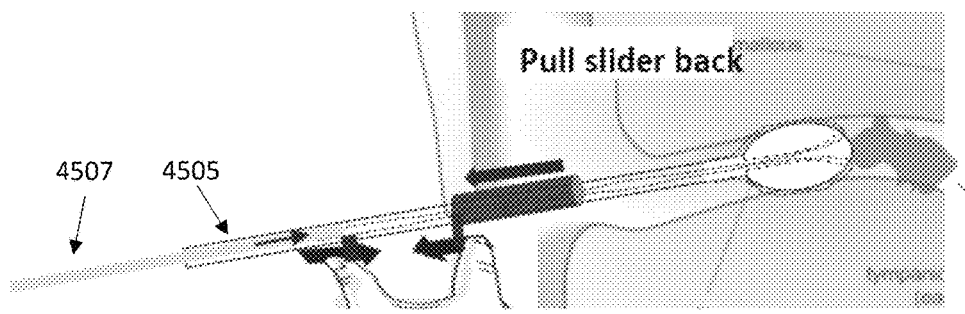
FIGS. 46A-46C show one example of a method of operating an inverting swab apparatus similar to that shown in FIG. 45.
Figure 46B:
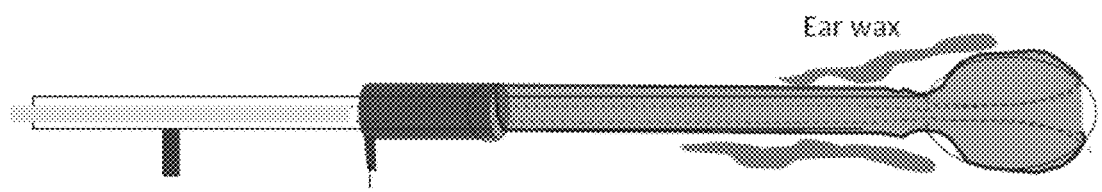
Figure 46C:
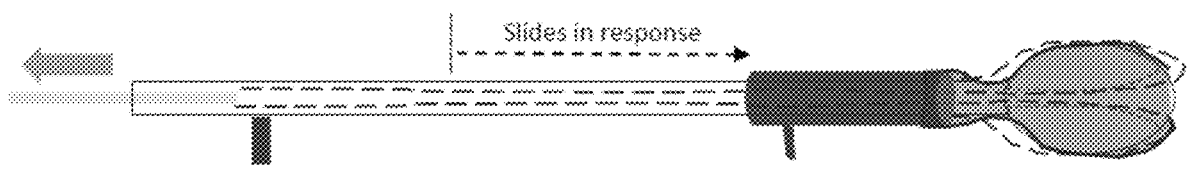

FIGS. 45 and 46A-46C illustrate another example of an inverting swab apparatus. In this example, unlike the examples described above, the apparatus may be actuated by pulling (un-inverting) and rolling the inverting swab sleeve out of lumen of the elongate tubular shaft, rather than rolling an inverting into the lumen of the elongate tubular shaft. For example, in FIG. 45 the inverting swab apparatus includes an elongate tubular shaft 4505 that includes a distal end region with a bulb region 4517 over and across which the inverting swab sleeve 4501 may be moved. The finger control in FIG. 45 is attached to the first end of the inverting swab sleeve (e.g., at the cuff region) and is configured as a slider 4517 having a first grip projection 4520. A second, fixed, grip projection 4522 is on the outer surface of the elongate tubular shaft. The device has an initial (start) configuration in which the inverting swab sleeve is mostly inverted and held within the lumen of the elongate tubular shaft, as shown. The device may be actuated as shown in FIG. 46A, showing the device inserted into an ear canal. Pulling back on the slider to reduce the distance between the first 4520 and second 4522 grip projections as shown may roll the inverting swab sleeve out of the elongate tubular member so that it may gently rub against the canal of the ear and remove wax material and/or dry the canal, as shown. Once completed, the device may be removed from the ear canal and cleaned, as shown in FIG. 46B. The device may be reset by pulling the reciprocating shaft 4507 proximally to pull the inverting swab sleeve back into the elongate tubular shaft 4505, as shown in FIG. 46C.

Figure 47A:
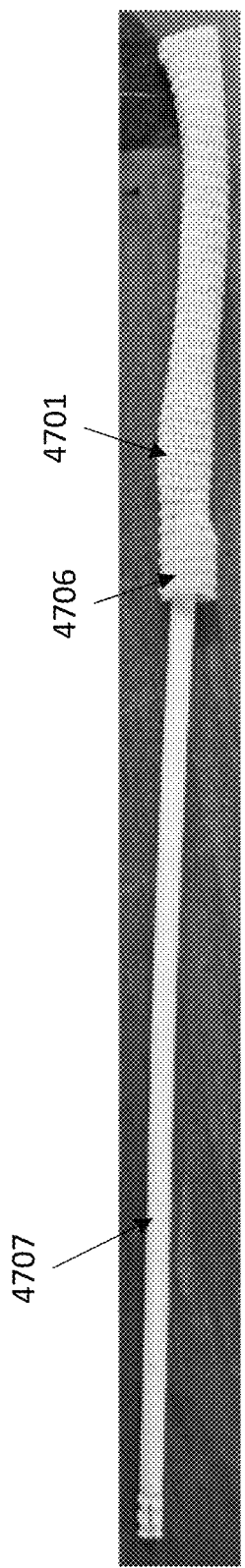
FIGS. 47A-47B show an inverting swab apparatus.
Figure 47B:
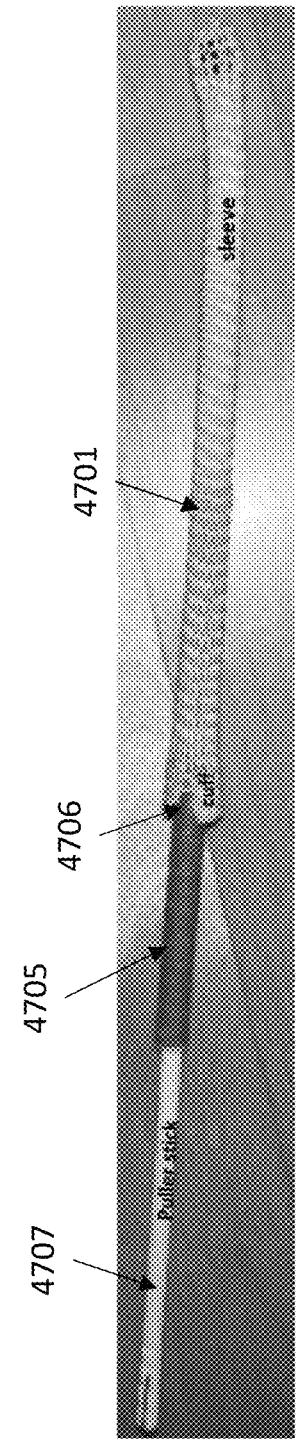

FIGS. 47A-74B illustrate another example of an inverting swab apparatus as described herein. In this example the device includes an elongate tubular shaft 4705 and an inverting swab sleeve 4701 that is coupled at one end to a reciprocating shaft (driver) 4707. FIG. 47A shows just the reciprocating shaft and the inverted inverting swab sleeve. FIG. 47B shows the inverting swab sleeve 4701 extending over the elongate tubular shaft 4705 with the reciprocating shaft 4707 extending through the lumen of the elongate tubular shaft. The second end of the inverting swab sleeve include a cuff 4706. The device is shown in the initial (starting) configuration in FIG. 47B, and may be inserted into the body and actuated by pulling the reciprocating shaft 4707 proximally relative to the elongate tubular shaft 4705 (e.g., while holding the elongate tubular shaft).

Figure 48A:
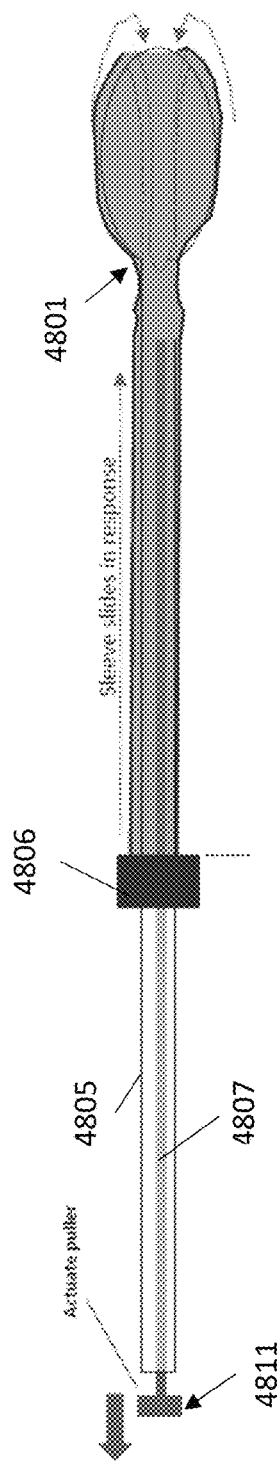
FIGS. 48A-48C illustrate an inverting swab apparatus.
Figure 48B:
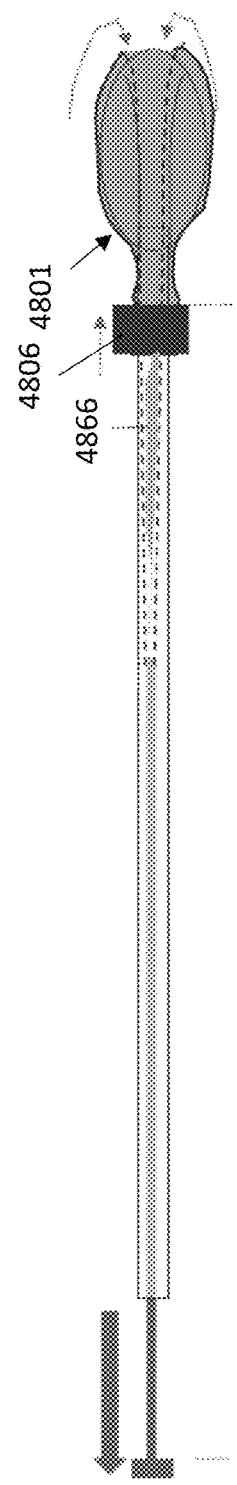
Figure 48C:
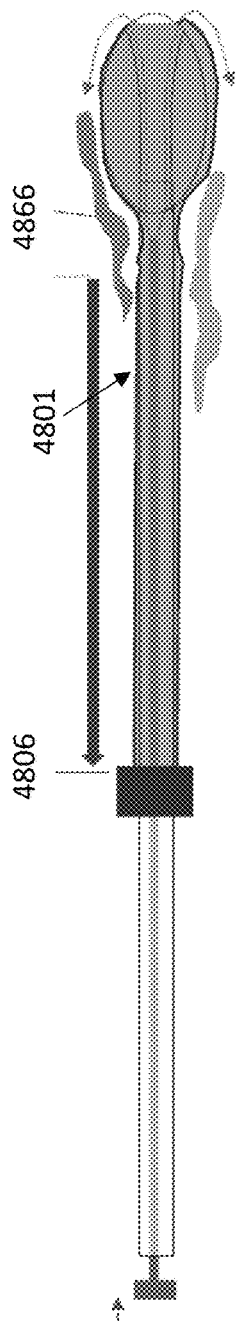

FIGS. 48A-48C illustrate another example of a device similar to that shown in FIGS. 47A-47B. in this example, the inverting swab apparatus includes an elongate tubular shaft 4805, an inverting swab sleeve 4801 comprising an inverted tube that is inverted over the outside of the elongate tubular shaft, and a driver for driving inversion of the inverting swab sleeve over the elongate tubular shaft, wherein the driver comprises a reciprocating shaft 4807. The proximal end of the reciprocating shaft may be a control 4811. One end of the inverting swab sleeve includes a cuff 4806. The second end of the inverting swab sleeve is coupled to the reciprocating shaft. FIG. 58B shows the device of FIG. 48A being actuated by pulling the control proximally to invert and roll the inverting swab sleeve into the elongate tubular shaft, allowing it to collect material (e.g., wax 4866) in the lumen of the elongate tubular shaft. After removing the device from the body, it may be cleaned (if desired) and/or reset by pulling the sleeve 4806 proximally, as shown in FIG. 48C.

Figure 49A:
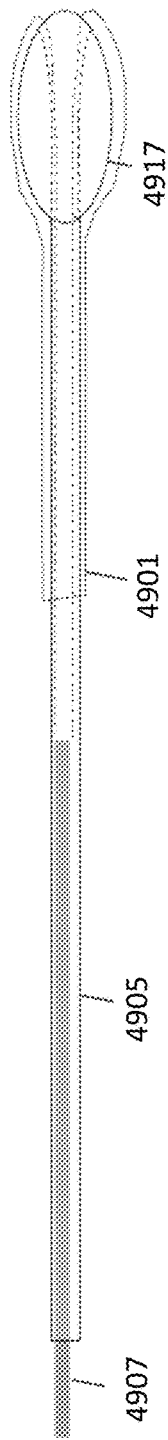
FIGS. 49A-49E show examples of inverting swab apparatuses having different bulb regions.
Figure 49B:
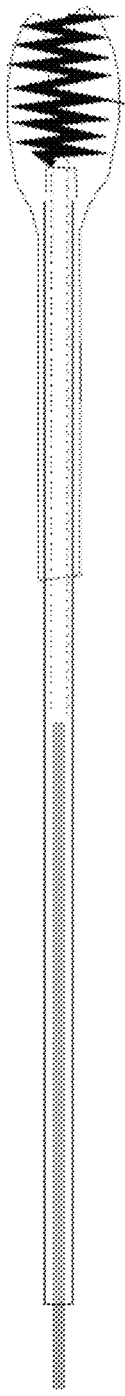
Figure 49C:
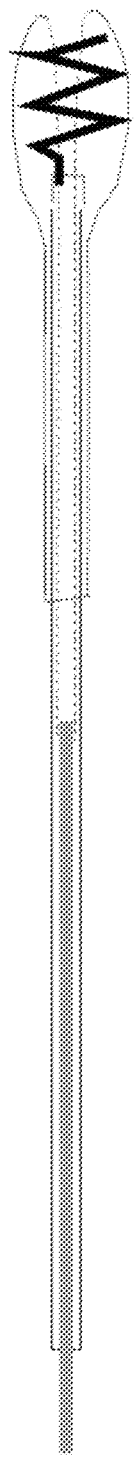
Figure 49D:
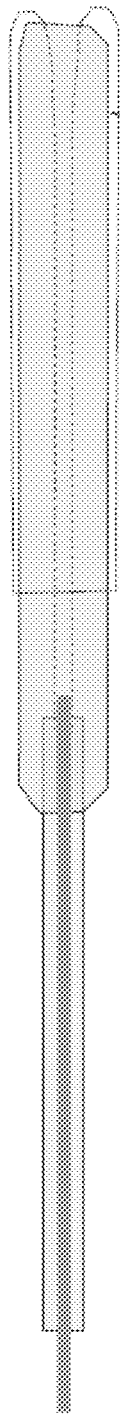
Figure 49E:

Any of these apparatus may include an optional bulb region at or near the distal end. FIGS. 49A-49E show examples of variations of bulb regions that may be included in any of these apparatus. FIG. 49A shows an inverting tube apparatus with an elongate tubular shaft 4905, an inverting swab sleeve 4901 comprising an inverted tube that is inverted over the outside of the elongate tubular shaft, and a driver for driving inversion of the inverting swab sleeve over the elongate tubular shaft, wherein the driver comprises a reciprocating shaft 4907. The distal end of the elongate shaft includes a bulb region 4917. The bulb may be attached to the elongate shaft or formed integrally with it. In some examples the bulb is formed of a material such as a plastic (e.g., PET, HDPE, nylon, etc.). In FIG. 49B the bulb 4917' is shown formed of a wire or ribbon that is coiled to assume a football-shape that may be atraumatic, e.g., when inserted into the ear canal. FIG. 49C shows an example in which the bulb 4917" is similar to that shown in FIG. 49B, but the wire or ribbon is wound with a more open pitch. FIG. 49D shows an example in which the bulb region 4917''' is longer, forming an elongate cylindrical region. Finally FIG. 49E illustrates an example of a bulb region 4917'''' that may be formed by any appropriate material, such as cotton or other absorbent material, over which the inverting swab sleeve 4901. This may separate, somewhat, the absorbency and capture functions of the apparatus.

Figure 50A:
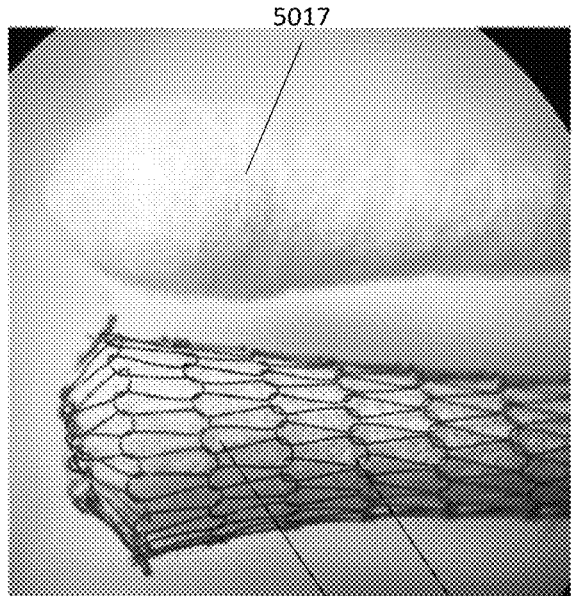
FIGS. 50A-50C illustrate an example of an inverting swab apparatus.
Figure 50B:
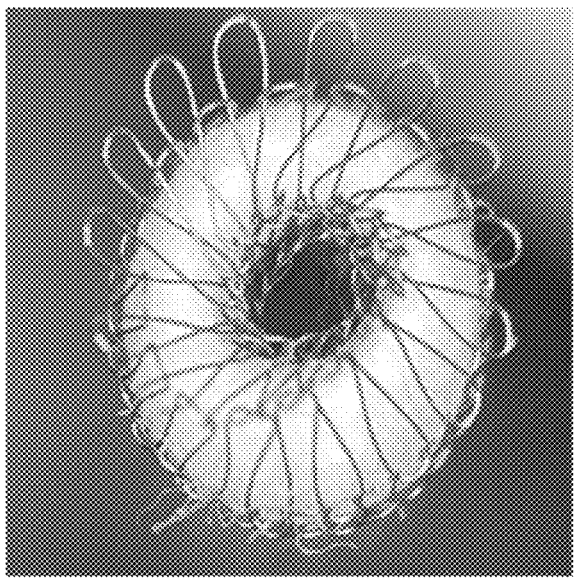
Figure 50C:
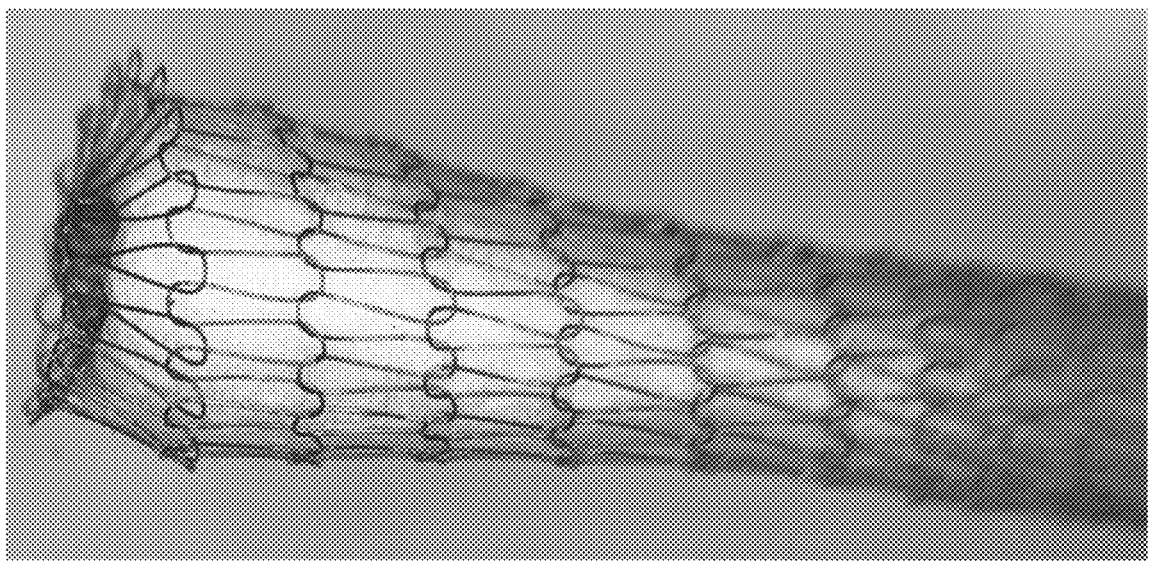

FIGS. 50A-50C illustrate another example similar to that shown in FIG. 49E, in which the distal end of the device includes a bulb formed of a cotton material. The bulb region 5017 is formed of a cotton material similar to a traditional swab (shown in FIG. 50A above the distal end of the inverting swab apparatus). The inverting swab apparatus includes an inverting swab sleeve 5001 that extends over the bulb and inverts into the inner lumen of the elongate tubular shaft, as shown in FIGS. 50B, and 50C.

Figure 51C:
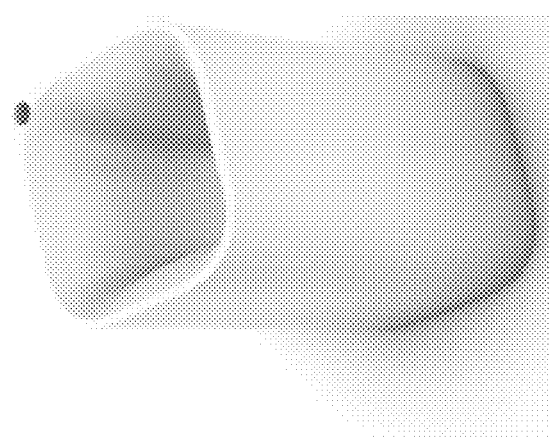
FIGS. 51A-51C illustrate examples of dispensing systems for an inverting swab apparatus.
Figure 51B:
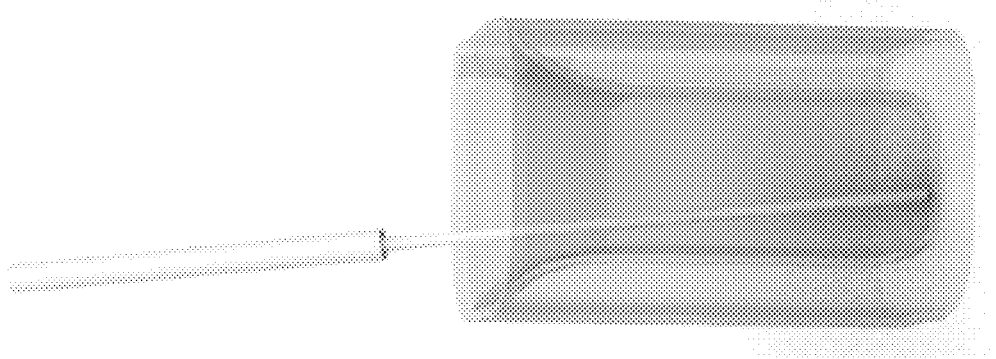
Figure 51A:
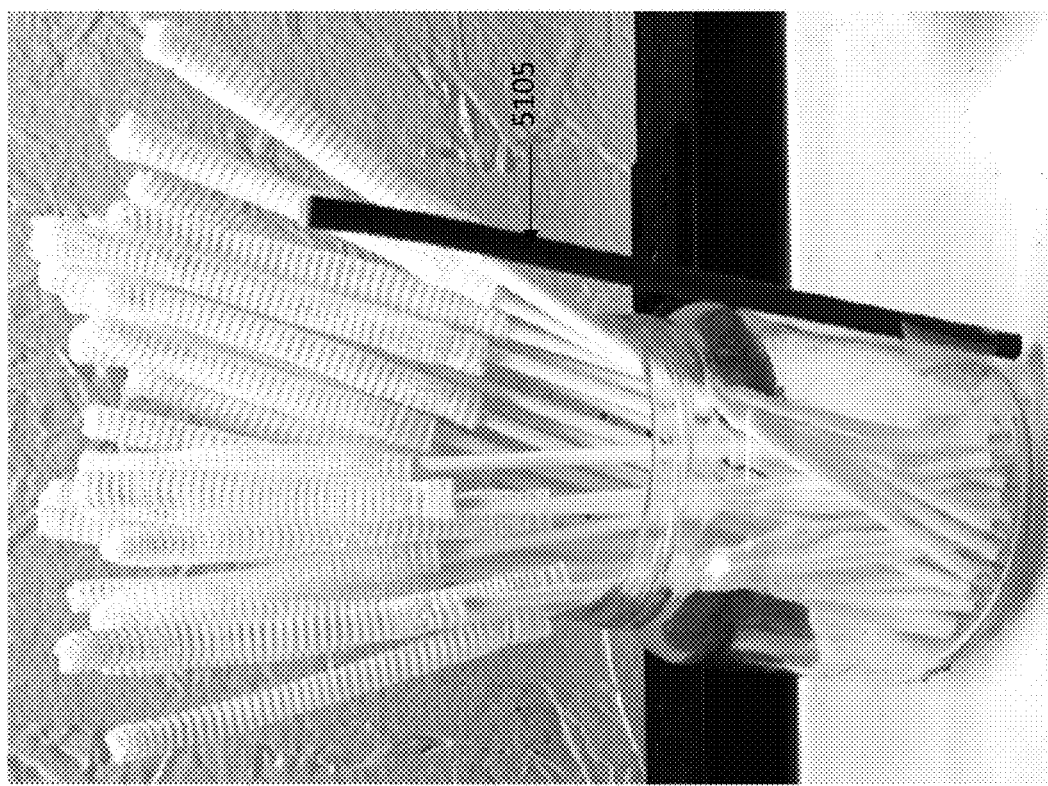

FIGS. 51A-51C show another example of a dispensing system for an inverting swab apparatus. In this example, the dispensing system may include a container for the elongate tubular shaft portion 5105, which may be separable from the rest of the apparatus, and useable with a plurality of reciprocating shafts coupled to the inverting swab sleeve. A separate container may be used to hold the inverting swab sleeves, as shown in FIGS. 51A-51C.

Figure 52A:
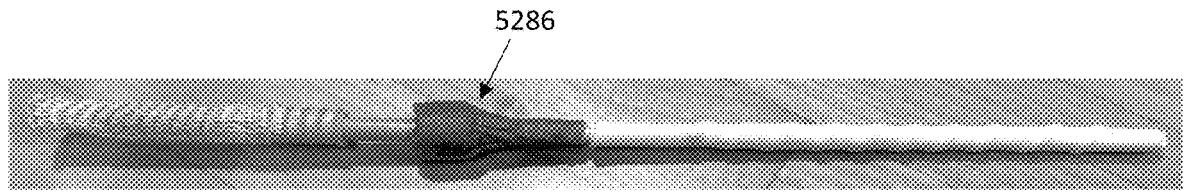
FIGS. 52A-52B show examples of inverting swab apparatuses having a finger guard region.
Figure 52B:
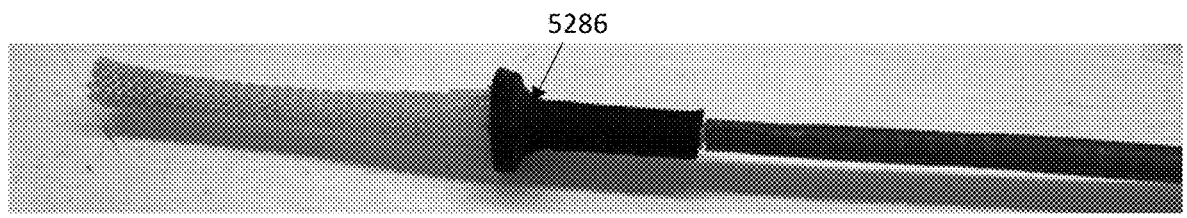

FIGS. 52A-52B illustrate alternative examples of inverting swab apparatuses including a stop finger grip/shield region 5286. The device may be similar to that shown in FIGS. 47B and 48A-48C, but may include a flanged, shield region 5286 to provide a grip that may prevent the user from inadvertently gasping the inverting swab sleeve during use.

In some example the apparatus may include a bulb or stop region that prevents or limits insertion of the apparatus too deep into the body. For example, FIGS. 53A-53B may include a stop or bulb 5317 that is offset from the distal end of the device by a predetermined distance 5317. For example, the offset distance (x) may be between 3-20 mm (e.g., between 5-15 mm, etc.). The stop/bulb may be larger than those described above, and may have a diameter of, e.g., between 5-10 mm (as compared to those in the figures before FIG. 53A, which may be less than 5 mm, e.g., between 1 mm and 5 mm, between 1 mm and 4.5 mm, between 1 mm and 4 mm, between 1 mm and 3.5 mm, between 1 mm and 3 mm, etc.). The device may otherwise function as described herein. FIG. 53B shows a comparison between a traditional swab, and the example shown in FIG. 53A with, and without, the stop/bulb 5317. FIG. 53C illustrates the operation of the apparatus of FIG. 53A to limit or prevent insertion to deeply into the ear canal, protecting the ear drum.

Figure 53A:
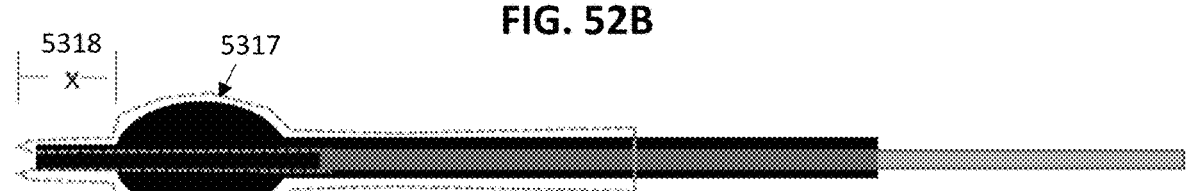
FIGS. 53A-53C show an example of an inverting swab apparatus including a safety stop limiting the depth of insertion.
Figure 53B:
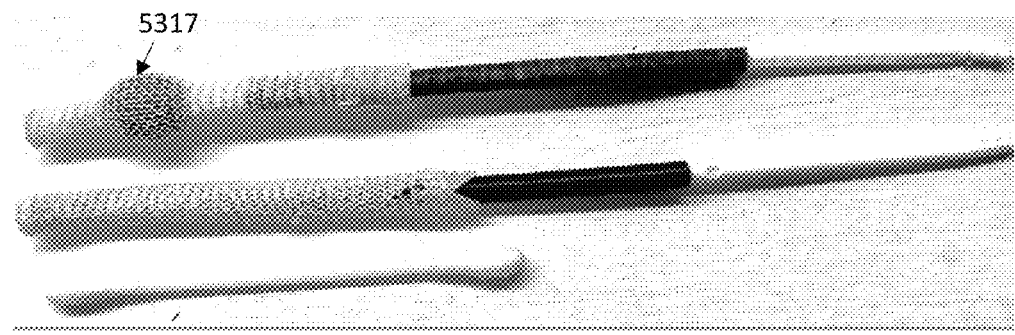
Figure 53C:
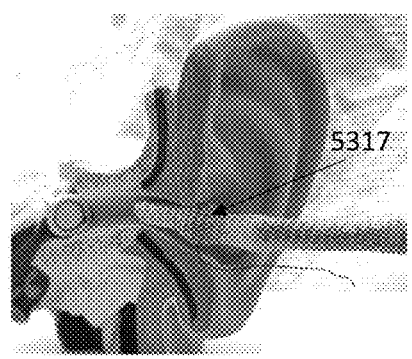
Figure 54A:
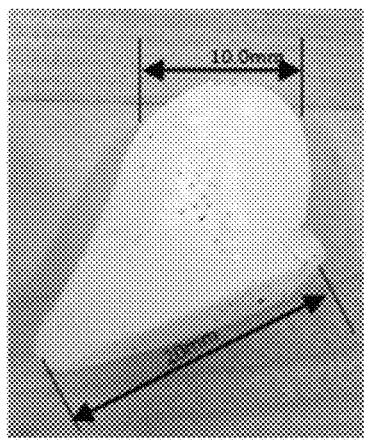
FIGS. 54A-54I illustrate examples of safety stops for an inverting swab apparatus.
Figure 54B:
Figure 54C:
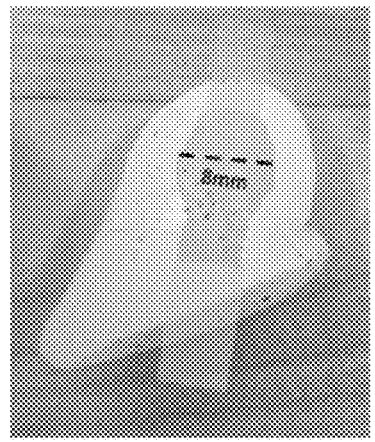
Figure 54D:
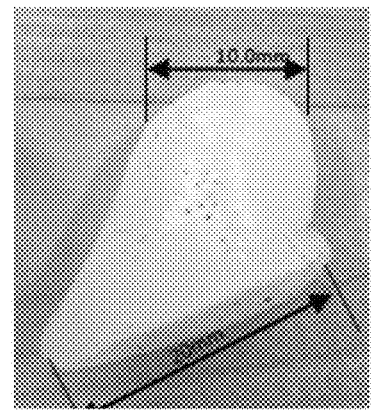
Figure 54E:
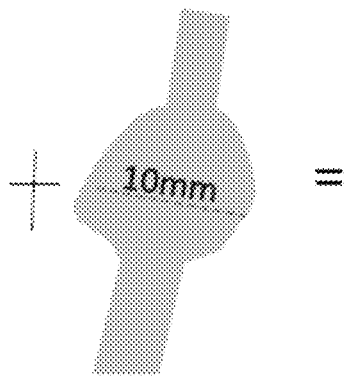
Figure 54F:
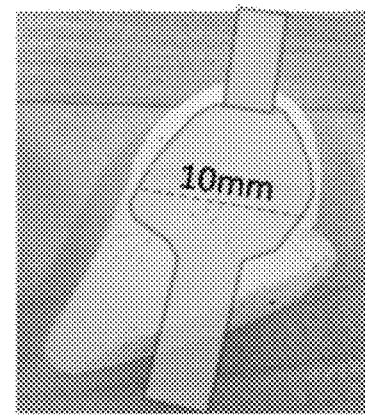
Figure 54G:
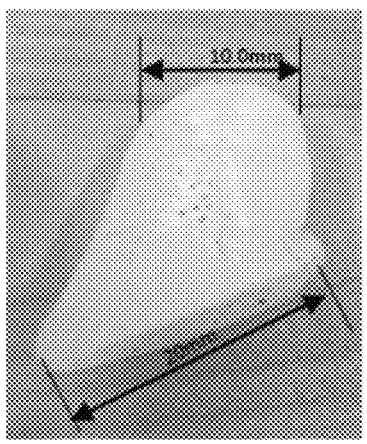
Figure 54H:
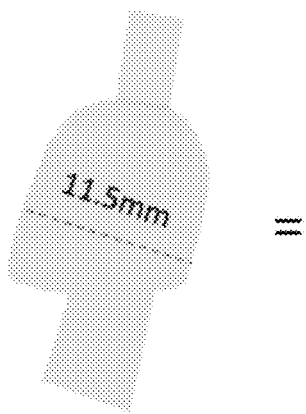
Figure 54I:
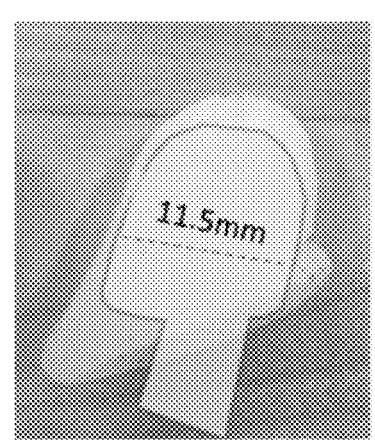

The bulb shown in FIGS. 53A-53C may be referred to as a safety stop or safety bulb and may be any appropriate shape or dimension. FIGS. 54B, 54E and 54H illustrate examples of exemplary shapes and dimensions (note that these dimensions are examples only and may be +/−2%, 5%, 7%, 8%, 10%, 15%, 20%, 25%, etc.). FIGS. 54A, 54D and 54G illustrate a model of an ear concha region, showing exemplary dimensions. The safety bumps shown are shown in FIGS. 54B, 54E and 54H are overlaid with the ear concha models and shown for comparison in FIGS. 54C, 54F and 54I.

Figure 55A:
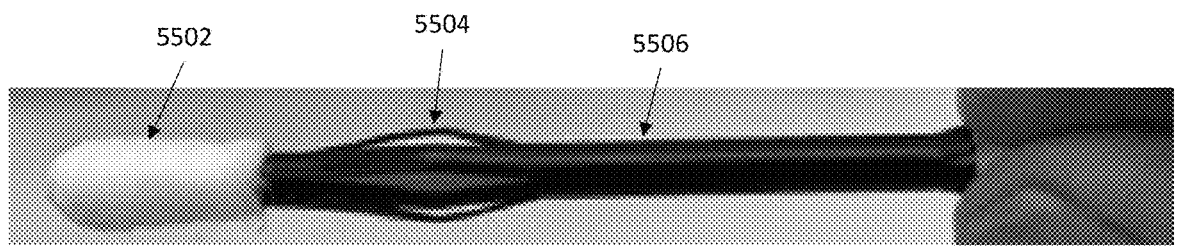
FIGS. 55A-55B show an example of a swab device including an expandable scraper.
Figure 55B:
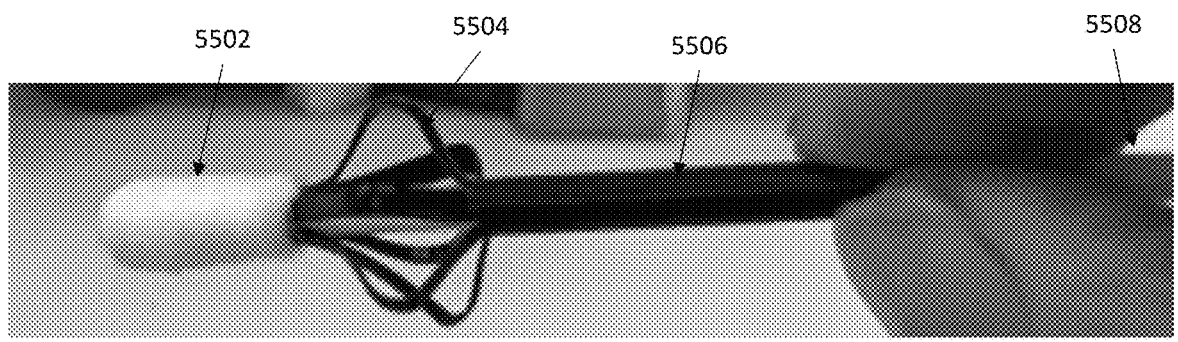

Also described herein are swab devices that may include an expandable scraper adjacent to an absorption portion. For example, FIGS. 55A-55B illustrate an example of an apparatus including a distal absorbent portion 5502 that is adjacent and distal to a radially expandable scraper 5504 that is configured to expand radially outward and collapse radially down by controlling an outer sliding member 5506 at the proximal end of the device. FIG. 55A shows the scraper in the collapsed (partially collapsed configuration, with the sliding member 5506 extended proximally. FIG. 55B shows the scraper in the expanded configuration 5504 with the sliding member 5506 in a more distal position. The sliding member may be slid distally or proximally relative to an inner elongate member 5508 that may be used as a handle. The device may include a lock or latch to hold the scraper in an expanded and/or collapsed configuration.

In FIGS. 55A-55B, the absorbent distal region 5502 may be, e.g., a cotton tip (for water absorption) and may be attached to the inner elongate member 5508. The scraper may be flared outwards and may be a serrated or braided section that, when compressed by advancing the sliding outer member 5506 distally, can expand. This expanded area can aid in scraping/rubbing of target tissue (e.g., ear wax) or limiting depth of tip insertion.

Alternatively, the apparatus may not include a cotton swab tip, but may instead include a water absorbent sleeve that can slide over the expanded section and into the inner lumen of the inner member.

Any of these apparatuses may be adapted for use in the nose.

In some examples the apparatus may be configured to include a bias for automatic deployment of the inverting swab sleeve. For example, a bias, e.g., spring, may be compressed to load the inverting swab sleeve over the outer elongate tubular shaft. Once inserted into the body region to be treated (e.g., nose, ear, etc.) the bias may be released, e.g., by releasing a latch or switch, and the reciprocating shaft may be automatically driven by the bias to invert the inverting swab sleeve over the distal end of the device, and into the elongate tubular shaft to rapidly capture a material and/or dry the body region.

FIGS. 56A and 56B illustrate an example of an inverting swab apparatus configured to automatically deploy upon release of a bias. In FIG. 56A the device includes an inverting swab sleeve 5601 that is shown fully inverted into the inner lumen of the elongate tubular shaft 5605. The inverting swab sleeve is coupled to a reciprocating shaft 5607 via a piston head 5658 (that may, in some examples, form a seal within the elongate tubular shaft) at a second end of the inverting swab sleeve. The first end of the inverting swab sleeve may be coupled to a cuff, or sleeve black 5653 that is slideably positioned over the elongate tubular shaft 5605. The reciprocating shaft may be attached at the proximal end to the control 5664, in this example configured as a puller. The reciprocating shaft 5607 may be part of a driver that includes one or more, e.g., a pair of, springs 5657, 5655. In the example shown in FIG. 56A the first spring is shown in a relaxed state and is configured to bias the piston reciprocating shaft and the piston head relative to the elongate tubular shaft 5605. A second bias (e.g., spring) may be coupled to the sleeve block 5653 and to the outer elongate tubular shaft 5605 (e.g., at a stopper that prevents excessive insertion 5659. This second spring may be configured to pull the inverting swab sleeve out of the lumen of the elongate tubular shaft when the reciprocating shaft is advanced distally. In some examples the spring force of the first bias is greater than the spring force of the second bias, thus the second bias will reset the inverting swab sleeve out of the lumen of the elongate tubular shaft and over the elongate tubular shaft only when the first spring is compressed by the user. The outer surface of the elongate tubular shaft 5605 may include a stop 5669 at the distal end region to prevent the inverting swab sleeve from completely inverting and being pulled into the inner lumen of the elongate tubular shaft, particularly when automatically actuated by the first spring.

For example, the first spring 5657 may be engaged by advancing the reciprocating shaft distally to compressing the first spring, allowing the second spring to re-invert the inverting swab sleeve over the outer surface of the elongate tubular shaft, as shown in FIG. 56B. once engaged, the first spring may be held (locked) in the compressed state until released.

The apparatus shown in FIGS. 56A-56B may also include one or more distal ports 5651 for applying aspiration and/or irrigation into the body. In some examples the apparatus may include one or more proximal aspiration/irrigation ports 5660. In FIG. 56A the apparatus may also include an air dampener 5667 around the first spring 5657.

The device in FIGS. 56A-56B includes a spring loaded control (puller 5664) that can be used to compress the spring before inserting into the body, e.g., nose. The stopper 5659 may be configured as a flange or ring that at least partially surrounds the outer elongate tubular shaft 5605 and preventing the user from inserting the device too far into the body (e.g., nose). When inserted, the optional ports 5651 at the tip may allow for irrigation or aspiration. When the user releases pressure on the control (e.g., puller 5664), the first spring drives the reciprocating shaft proximally, so that the inverting swab sleeve is pulled and inverted inside the elongate tubular shaft, collecting any material from within the body, such as mucus from within the nasal cavity. Optionally, in some examples, when releasing the first bias (first spring 5657), the bias may cause the sealed piston 5658 to pull a vacuum through the sealed piston head. This may allow the device to pull a brief vacuum in addition to the rolling inverting swab sleeve.

In any of these examples and air dampener may be included at a bottom of the device to slow the return of the first spring when the bias is release (e.g., by releasing the force applied to the control (puller 5654) and/or release the lock or latch preventing release. Thus, the air dampening may permit the device to allow for spring 1 (when released from compression) to shoot back at a slower pace. As mentioned, in some examples the apparatus may also include one or more irrigation/aspiration ports 5660, 5651 that may be visible at the distal and proximal ends of the device. Thus, fluid or air may be passed between these ports through one or more channels that run through the device wall that allow the user to apply and/or remove fluid (e.g., to wash and/or aspirate) into the body, such as the nose.

Figure 57B:
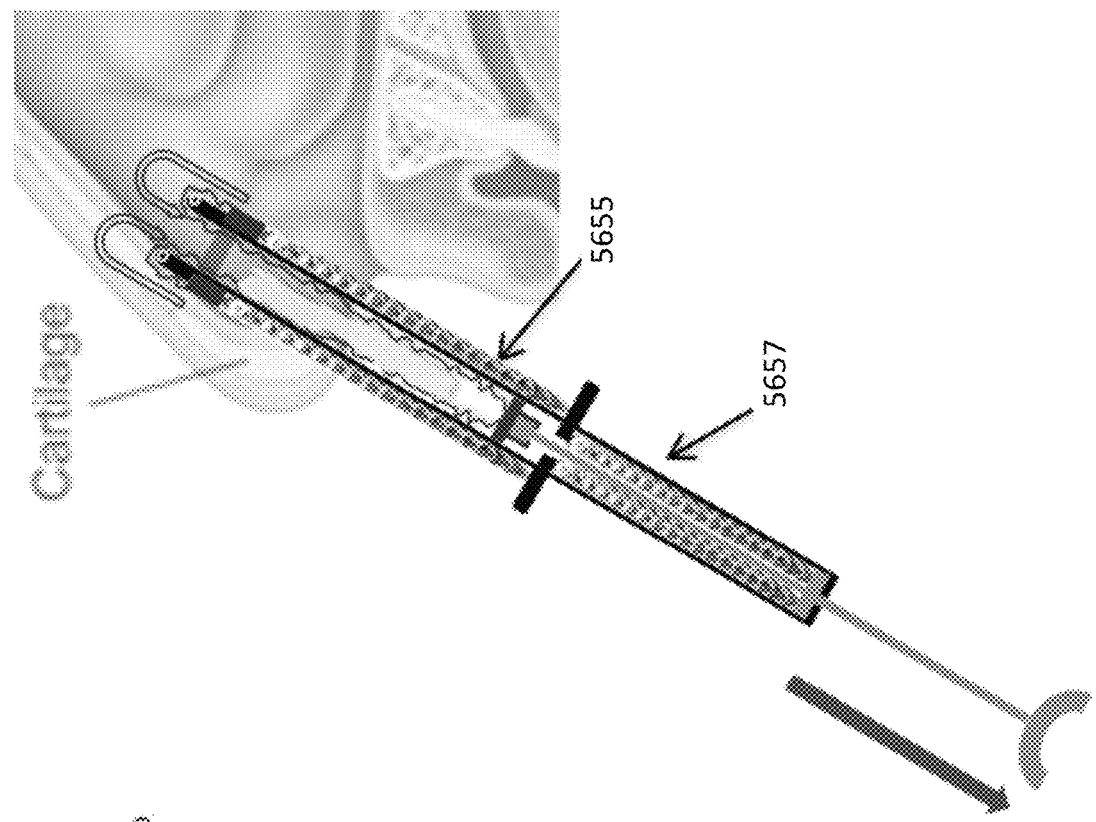
FIGS. 57A-57B illustrate one example of use of an inverting swab apparatus such as the one shown in FIGS. 56A-56B.
Figure 57A:
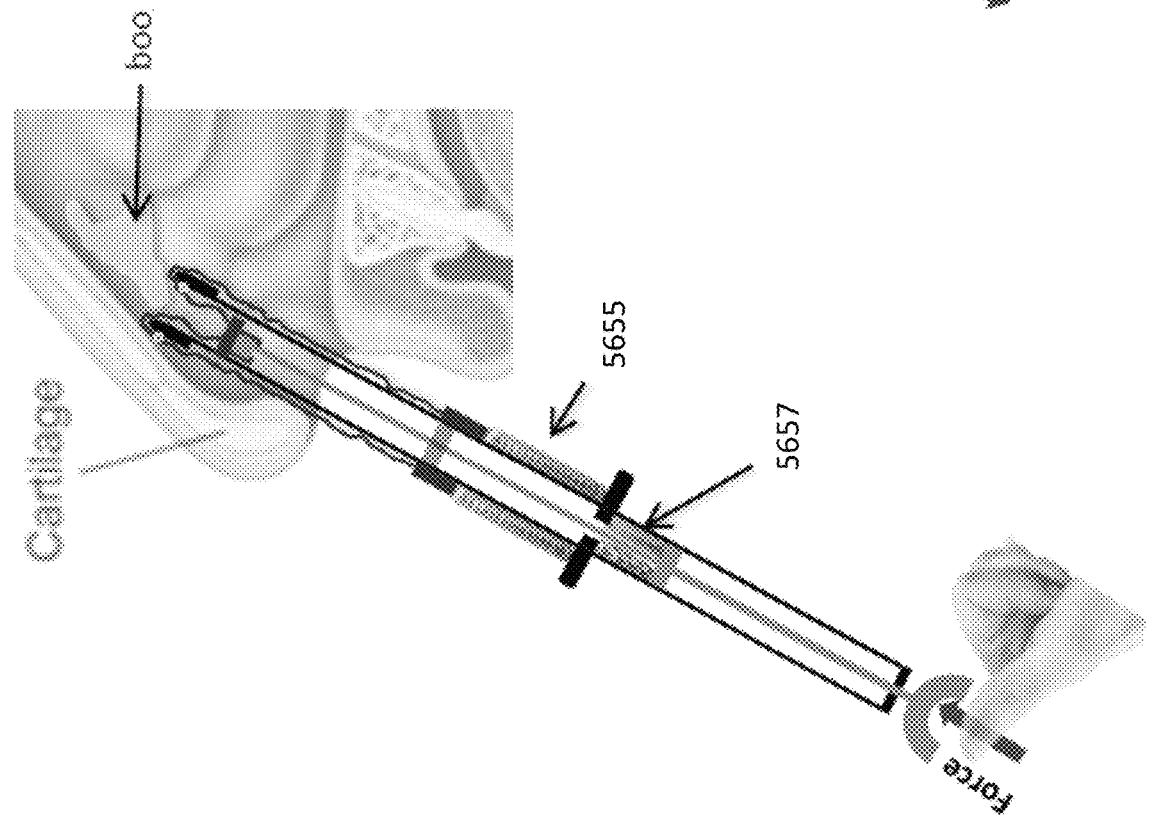

FIGS. 57A and 57B illustrate examples of the operation of an apparatus such as the one shown in FIGS. 56A-56B. For example, in FIG. 57A, the device may be primed by pushing in the control, applying force to compress the first spring, and the device may be inserted into the nose, as shown, or in some examples, into the ear. In FIG. 54A, the device, as shown in FIGS. 56A-56B, includes a spring-loaded puller that is compressed by compressing the first spring 5657 before inserting into the nose. A stop (e.g., ring, flange, etc.) may prevent the device from being inserted too far into the nasal cavity. Once the user has inserted the device into the nose to the desired position, and (optionally) completed any irrigation/aspiration desired, the user may release pressure on the puller, allowing the first spring 5657 to expand and pull the inverting swab sleeve inside the elongate tubular shaft, collecting any material (e.g., mucus) from within the nose, as shown in FIG. 57B. In the example shown in FIG. 57A, a stop 5669 may prevent the inner sleeve from being completely pulled into the elongate tubular shaft. The second bias (second spring 5655) may have a lower spring constant than the first spring, and may help return the inverting swab sleeve to the starting position, e.g., deployed around the outside of the elongate tubular shaft, when the first spring is compressed by applying force to the control.

Figure 58:
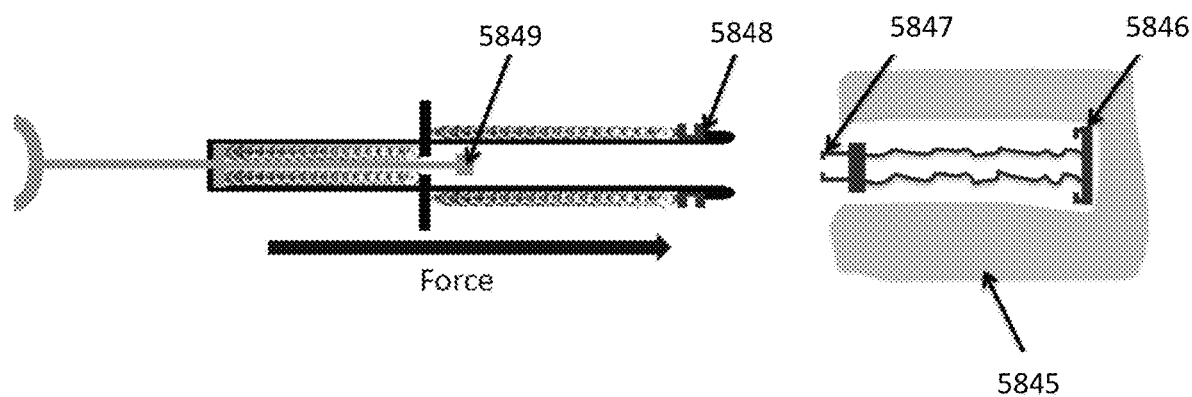
FIG. 58 is an example of an inverting swab apparatus similar to the one shown in FIGS. 56A-56B and 57A-57B including an inverting swab sleeve assembly.

FIG. 58 illustrates an example of an apparatus similar to that shown in FIGS. 56A-56B that include a removable/replaceable inverting swab sleeve assembly. In the example shown in FIG. 58, the replaceable, one-time use inverting swab sleeve assembly may connect to the reusable portion of the device (e.g., the swab actuator). The replaceable element may be held in a holding mechanism 5845. By pushing the swab actuator into the holding mechanism for the inverting swab sleeve assembly, the puller end 5849 may connect to the hooks 5847 and the sleeve snaps 5846 may connect to the sleeve blocks 5848. Then pull the device (with the new inverting swab sleeve assembly attached) may then be operated as described above.

Figure 59:
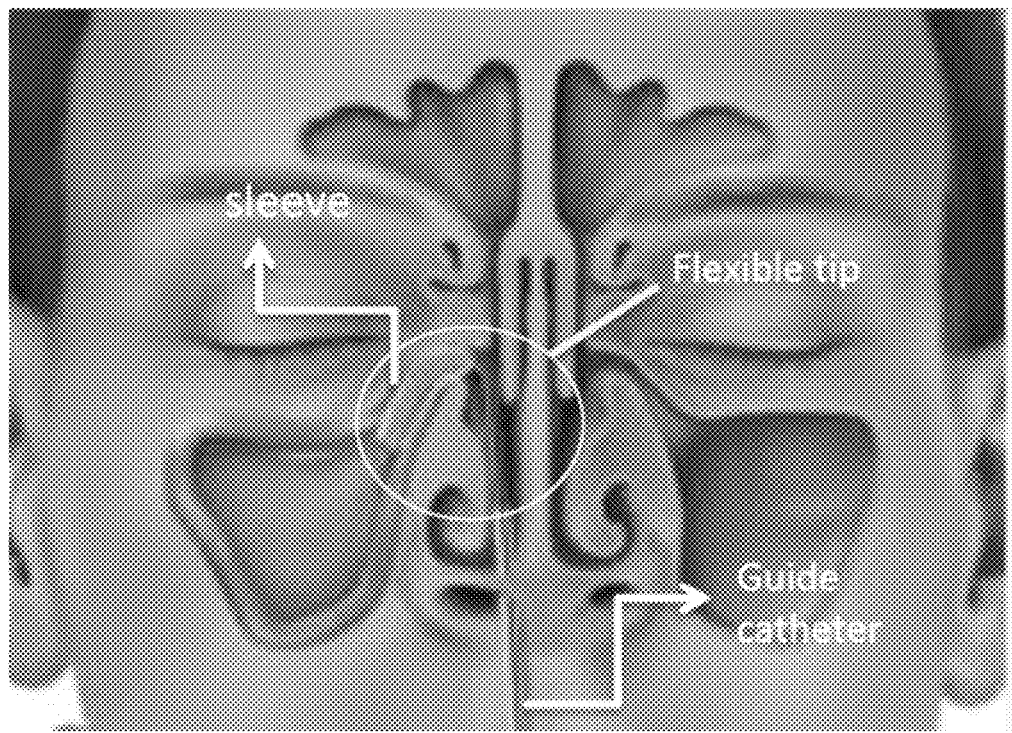
FIG. 59 illustrates the use of an inverting swab apparatus within a patient's sinuses.

In any of the apparatuses described herein the distal end region may be sufficiently flexible so that they may be navigated around turns and bends within the body region, including the nasal sinuses, as shown in FIG. 59. In any of these apparatuses, the end of the device may be guided or steered to a region of the body. For example, any of these apparatuses may be used with a guide catheter, guidewire, or the like. Any of these apparatuses may include one or more channels for guidance and/or for aspiration and/or for irrigation. The device may be lubricated to allow for easy insertion.

Stone Removal Devices

Figure 60A:
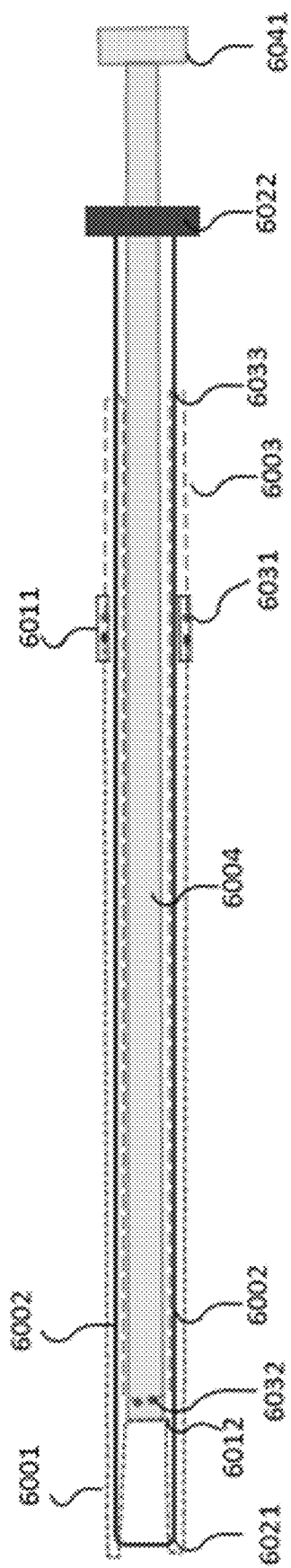
FIG. 60A shows an example of a resetting inverting sleeve apparatus configured to remove a material (e.g., stone) from a body.
Figure 60B:
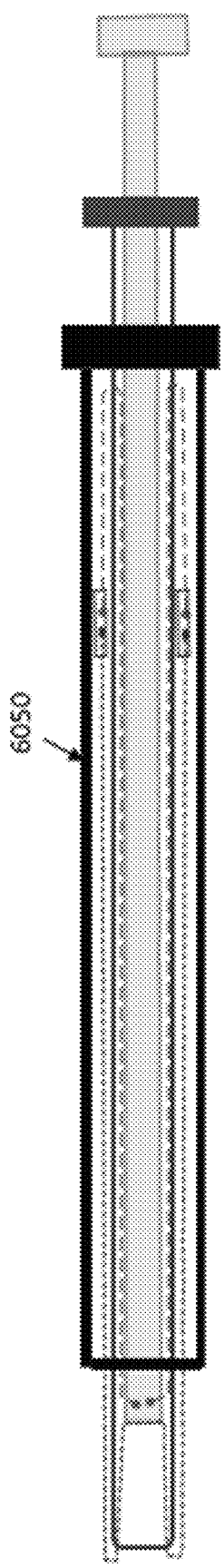
FIG. 60B shows an example of a system including the apparatus of FIG. 60A.

Any of the apparatuses described herein may be configured for use within the body to remove body stones (e.g., kidney stone, gall stone, bladder stone, urinary tract stone, etc.). In particular the swab actuator may be adapted to operate within the body to remove one or more stones, including operating in conjunction with one or more tools to break up and remove stones. For example, FIGS. 60A-60B illustrate an example of an apparatus for removing stones from the body. In general, this apparatus may be configured as a device (e.g., an actuator) comprising: an elongate tubular outer shaft; a reciprocating inner shaft, wherein the reciprocating shaft comprises an inner lumen; an inverting conveyor tube configured to roll and invert over the elongate tubular shaft as the reciprocating shaft is moved; one or more tethers coupling a first end of the inverting conveyor tube to a first end region of the reciprocating shaft and/or to a second end of the inverting conveyor tube; wherein a second end of the inverting conveyor tube is coupled to the first end region of the reciprocating shaft; and a control for operating the reciprocating inner shaft to reciprocate the reciprocating shaft relative to the elongate tubular shaft to roll and invert the inverting conveyer tube. These devices (as with any of the apparatuses described herein) may be referred to as "resettable" inverting devices.

In FIG. 60A, the device includes an inverting conveyor tube 6001 that is configured to be everted around an elongate tubular outer shaft 6002 as the reciprocating inner shaft 6004 is driving proximally and distally (e.g., back and forth). The inverting conveyor tube 6001 may include an optional cuff 6011 at a first end region, to which one or more (and preferably a plurality of) tethers 6003 are attached. Additionally or alternatively, the tethers may be attached directly to the inverting conveyor tube at the first end. The second end(s) of the tether(s) are functionally attached to the second end of inverting conveyor tube 6001, either directly or indirectly, including at or near the distal end region of reciprocating shaft 6004 that is coupled to the inverting conveyor tube 6001. Thus, both end of the inverting conveyor tube 6001 are functionally coupled to each other and movement of reciprocating shaft 6003 drives the rolling (and inverting/re-inverting) of the inverting conveyor tube over the distal end 6021 of the elongate tubular outer shaft 6002.

Thus, the proximal end of the inverting conveyor tube 6001 can terminate in a cuff section, as described above. Alternatively, a separate attachment cuff can be glued/fused to proximal (e.g., the second, inner, end) 6012 of the inverting conveyor tube 6001. In FIG. 60A the tethers 6003 are attached to the distal end region of the reciprocating shaft 6003 at a tether attachment region 6032.

The elongate tubular outer shaft 6002 may be configured as a catheter, and may be flexible or partially flexible (e.g., more flexible at the distal end region than more proximal regions). The elongate tubular outer shaft may include a hub 6022 that may act as a stop, e.g., for movement of the reciprocating inner shaft 6004. In some examples, a handle (not shown) may be included that may include one or more controls (sliders, dials, etc.) for reciprocating the inner shaft. In some cases the handle may include a limiter for limiting axial (e.g. proximal and/or distal) movement of the reciprocating inner shaft to prevent drawing the inverting conveyor tube too far into or out of the lumen of the elongate tubular outer shaft. The reciprocating inner shaft 6004 may include a hub or stop. In any of these apparatuses the reciprocating inner shaft may be hollow and may allow passage of one or more additional devices; in some cases the inverting conveyor tube may also form a passage that is continuous with the lumen of the reciprocating inner shaft. The reciprocating inner shaft may be coupled to a valve to regulate the flow of fluid in or out through the device.

In general, the elongate outer shaft may include one or more channels or openings 6033 through which the tethers 6003 may move as the reciprocating inner shaft drives rolling and inverting/re-inverting of the inverting conveyor tube. In some cases, as described above, the channels or openings are part of a flange. The region of the elongate outer shaft (including a flange region) where the tether passes through may be selectively thickened to reduce friction and/or to reinforce the elongate tubular shaft.

In FIG. 60B, the same device as shown in FIG. 60A is shown inserted through a guide catheter 6050. The inner diameter of the guide catheter may be larger than the outer diameter of the actuator device shown in FIG. 60A, to allow rolling of the inverting conveyor belt. In some examples the guide catheter may be shorter than the actuator, to allow the distal end region (including the inverting conveyor tube and tethers) to extend distally out of the guide catheter when fully deployed. The guide catheter can include one or more features to allow it to be steerable in one or more planes, which may aide in tracking or directing its tip into different anatomical locations including different calyx of the kidney. In general, the guide catheter may have a single lumen of multiple lumens. In any of these apparatuses, the guide catheter can have an integrated camera, light, irrigation port, and/or aspiration port, to enable all these features.

Figure 61A:
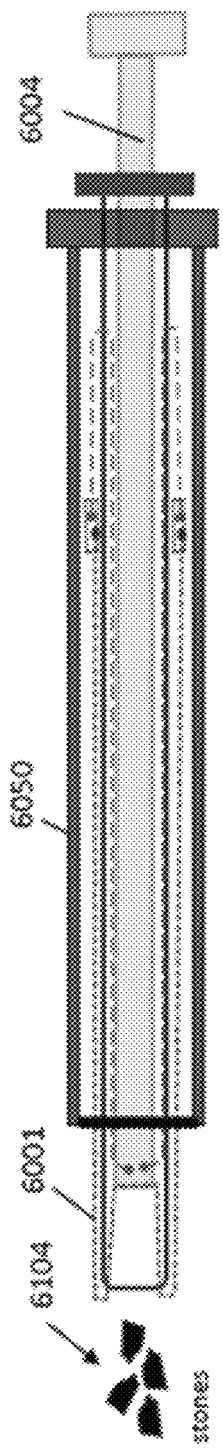
FIGS. 61A-61D illustrate one example of a method of using a device such as that shown in FIG. 60A to remove a stone (e.g., kidney stone) from a body.

FIGS. 61A-61D illustrates one example of a method of operation of an apparatus as shown in FIG. 60A-60B to remove stones from a body. In FIG. 61A the device (as described in 60A) is positioned within a guide catheter and positioned proximate to stoned 6104. The inverting conveyor tube and reciprocating shaft are in the initial "neutral" position, with the reciprocating shaft fully extended distally. The guide catheter 6050 may be used to position the device. The device may be poisoned with the aid or one or more imaging techniques, including the use of direct imaging, e.g., through the guide catheter, through a central lumen of the reciprocating inner shaft, etc., or external imaging (e.g., ultrasound, fluoroscopy, etc.).

Figure 61B:
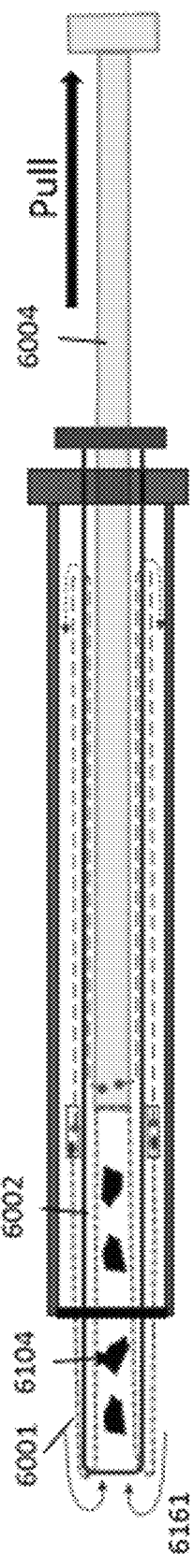
Figure 61C:
Figure 61D:
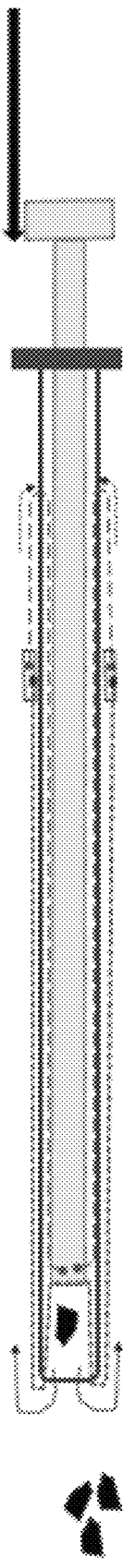

The stones 6104 may be ingested for removal by pulling the reciprocating inner shaft 6004 proximally, as shown in FIG. 61B, to ingest the stones into the inverting conveyor tube 6001 as it is rolled into 6161 and drawn into the lumen of the elongate tubular outer shaft 6002. The device may be removed out of the guide catheter by withdrawing proximally, as shown in FIG. 61C (leaving the guide catheter in position for additional access and removal). The device may then be emptied, to eject the removed stones out of the device (and rest to the initial position), by pushing the reciprocating inner shaft distally, as shown in FIG. 61D, and the process repeated. In general, these method and apparatuses may be used within a body region to remove stones, including the kidney, bladder, urinary tract, etc.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Within the figures and description above, the same features may be indicated in different figures with different numbers, in order to reflect the different figure number that the features corresponds to. In some cases similar or identical features may be shown with similar numbers (e.g., 43, 143, 243, etc.). Features shown in different states or configurations may be indicated by the use of one or more prime marks (e.g., 93, 93', 93", etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An inverting reciprocating system for use in a patient, the system comprising:
   an actuator comprising:
      an elongate tubular shaft having a proximal end and a distal end;
      a driver, the driver comprising:
         a reciprocating shaft within the elongate tubular shaft;
         an inverting conveyor tube configured to roll and invert over the distal end of the elongate tubular shaft as the reciprocating shaft is moved;
         one or more tethers extending proximally from a first end of the inverting conveyor tube along an outside of the elongate tubular shaft, the one or more tethers extending through or around a proximal end region of the elongate tubular shaft, and extending distally within the elongate tubular shaft and coupled to a distal end region of the reciprocating shaft and/or to a second end of the inverting conveyor tube,
         wherein the second end of the inverting conveyor tube is coupled to the distal end region, further wherein the one or more tethers reciprocate the inverting conveyor tube as the reciprocating shaft reciprocates; and
      a control for operating the driver to reciprocate the reciprocating shaft relative to the elongate tubular shaft to roll and invert the inverting conveyer tube.

2. The system of claim 1, wherein the elongated tubular shaft has a greater flexibility along a length of a distal end of elongated tubular shaft as compared to a proximal end region of the elongated tubular shaft.

3. The system of claim 1, wherein the control comprises one or more of: a slider, a knob, a roller, a dial, or a button.

4. The system of claim 1, further comprising an inverting swab sleeve that is configured to removably engage with the inverting conveyer tube of the actuator.

5. The system of claim 4, wherein the inverting swab sleeve is configured to invert over the inverting conveyor tube as it rolls and inverts over the elongate tubular shaft.

6. The system of claim 4, wherein the inverting swab sleeve comprise an engagement cap at a first end that is configured to engage with the inverting conveyer tube.

7. The system of claim 6, wherein the engagement cap comprises a bullet shape.

8. The system of claim 6, wherein the engagement cap comprises a compressible material.

9. The system of claim 6, wherein the engagement cap is configured to load into the inside of the inverting conveyor tube.

10. The system of claim 4, wherein the inverting conveyor tube of the inverting swab sleeve comprises one of: a knit, a weave or a braid.

11. The system of claim 4, wherein the inverting conveyor tube of the inverting swab sleeve comprises an absorbent cellulose fiber.

12. The system of claim 4, wherein the inverting swab sleeve has a diameter of between 3 mm and 10 mm.

13. The system of claim 4, wherein the inverting swab sleeve device is between 1.5 and 15 cm long.

14. The system of claim 4, further comprising a loading tube covering the inverting swab sleeve.

15. The system of claim 14, wherein the loading tube comprises a centering securement configured to releasably hold an engagement cap at a distal end of the inverting conveyor tube in a radially centered region of the loading tube.

16. The system of claim 4, further comprising a cuff at a second end of the inverting conveyor tube of the inverting swab sleeve.

17. The system of claim 16, wherein an inner diameter of the cuff is smaller than an outer diameter of the inverting conveyor tube.

18. The system of claim 17, wherein the cuff comprises a compressible, elastic material.

19. The system of claim 17, wherein the cuff comprises a tacky material.

20. The system of claim 1, wherein the elongated tubular shaft is bent or curved at a distal end region.

21. An inverting reciprocating system for use in a patient, the system comprising:
   an actuator comprising:
      an elongate tubular shaft having a proximal end and a distal end;
      a driver, the driver comprising:
         a reciprocating shaft slidably positioned within the elongate tubular shaft;
         an inverting conveyor tube configured engage with an inverting swab sleeve, wherein the inverting conveyer tube is configured to roll and invert over the distal end of the elongate tubular shaft as the reciprocating shaft is moved;
         one or more tethers extending proximally from a first end of the inverting conveyor tube along an outside of the elongate tubular shaft, the one or more tethers extending through or around a proximal end region of the elongate tubular shaft, and extending distally within the elongate tubular shaft to couple to a distal end region of the reciprocating shaft and/or to a second end of the inverting conveyor tube,
         wherein the second end of the inverting conveyor tube is coupled to the distal end region, further wherein the one or more tethers reciprocate the inverting conveyor tube as the reciprocating shaft reciprocates; and
      a control for operating the driver to reciprocate the reciprocating shaft relative to the elongate tubular shaft to roll and invert the inverting conveyer tube over the elongate tubular shaft.

22. An inverting reciprocating system for use in a patient, the system comprising:

an actuator comprising:

an elongate tubular shaft having a proximal end and a distal end;

a driver, the driver comprising:

a reciprocating shaft;

an inverting conveyor tube configured to roll and invert over the distal end of the elongate tubular shaft as the reciprocating shaft is moved;

one or more tethers extending proximally from a first end of the inverting conveyor tube along an outside of the elongate tubular shaft, the one or more tethers extending through or around a proximal end region of the elongate tubular shaft, and extending distally within the elongate tubular shaft and coupled to a distal end region of the reciprocating shaft and/or to a second end of the inverting conveyor tube, wherein the second end of the inverting conveyor tube is coupled to the distal end region, further wherein the one or more tethers reciprocate the inverting conveyor tube as the reciprocating shaft reciprocates; and a control for operating the driver to reciprocate the reciprocating shaft relative to the elongate tubular shaft to roll and invert the inverting conveyer tube; and an inverting swab sleeve comprising an inverted tube and an engagement cap coupled to first end of the inverted tube, wherein the inverting conveyor tube is configured to removably engage with the engagement cap of the inverting swab sleeve.

* * * * *